(12) United States Patent
Guerry et al.

(10) Patent No.: US 6,995,143 B2
(45) Date of Patent: Feb. 7, 2006

(54) MACROLIDES WITH ANTIBACTERIAL ACTIVITY

(75) Inventors: Philippe Guerry, Binningen (CH); Johannes Laurenz Kellenberger, Basel (CH); Stéphanie Blanchard, Bartenheim (FR)

(73) Assignee: Basilea Pharmaceutica AG, (CH)

( * ) Notice: Subject to any disclaimer, the term of this patent is extended or adjusted under 35 U.S.C. 154(b) by 47 days.

(21) Appl. No.: 10/371,108

(22) Filed: Feb. 20, 2003

(65) Prior Publication Data

US 2003/0212011 A1 Nov. 13, 2003

(30) Foreign Application Priority Data

Feb. 28, 2002 (EP) .................... 02004295

(51) Int. Cl.
*A61K 31/70* (2006.01)
*C07H 17/08* (2006.01)

(52) U.S. Cl. .................... 514/29; 536/7.2; 536/7.3; 536/7.4

(58) Field of Classification Search ............... 536/7.3, 536/7.4, 7.2; 514/29
See application file for complete search history.

(56) References Cited

U.S. PATENT DOCUMENTS 6,740,642 B2 * 5/2004 Angehrn et al. .............. 514/29

FOREIGN PATENT DOCUMENTS

| EP | 680 967 | 11/1995 |
| EP | 994 598 | 4/2000 |
| EP | 1 114 826 A2 * | 7/2001 |
| FR | 2 732 684 | 10/1996 |
| WO | WO 98/09978 | 3/1998 |
| WO | WO 02/16380 | 2/2002 |
| WO | WO 02/50091 | 6/2002 |
| WO | WO 02/50092 | 6/2002 |
| WO | WO 02/060912 | 8/2002 |

OTHER PUBLICATIONS

Denis et al., Bioorg. Med. Chem. Letters, 10, pp. 2019-2022 (2000).
Phan et al., Organic Letters, 2 (19), pp. 2951-2954 (2000).
Denis et al., Bioorg. Med. Chem. Letters, 9, pp. 3075-3080 (1999).
Or et al., J. Med. Chem., 43, pp. 1045-1049 (2000).

* cited by examiner

*Primary Examiner*—Elli Peselev
(74) *Attorney, Agent, or Firm*—Gibbons, Del Deo, Dolon, Griffinger & Vecchione

(57) ABSTRACT

The invention provides new macrolides antibiotics of formula I with improved biological properties and having the formula

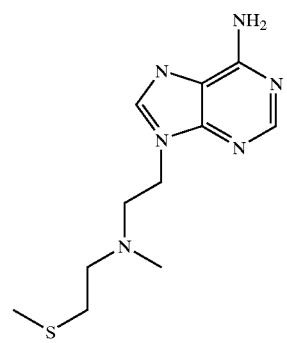

wherein $R^1$, $R^2$ and $R^3$ are as herein described.

57 Claims, No Drawings

MACROLIDES WITH ANTIBACTERIAL ACTIVITY

BACKGROUND OF THE INVENTION

This invention relates to new macrolide antibiotics with improved activity and methods of making them, the use of such antibiotics for the treatment of infectious diseases and compositions containing such macrolides.

The interest in macrolide antibiotics is increasing because these compounds are a very effective and safe class of agents against gram positive pathogens. Extensive spread of erythromycin A resistance among gram positive cocci isolates raised the urgent need for novel derivatives with improved activity, stability and antimicrobial spectra. The two most successful second generation agents derived from erythromycin A (Compound 1) through semisynthesis were its 6-O-methyl derivative clarithromycin (Compound 2) and the 15-membered azalide azithromycin (Compound 3) arising from a Beckman rearrangement. However, while featuring improved pharmacokinetics, none of these agents possessed a significant activity against bacterial isolates showing macrolide-lincosamide-streptogramine B (MLS B) cross resistance.

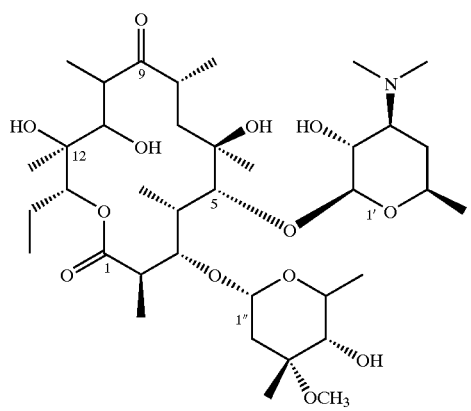

1

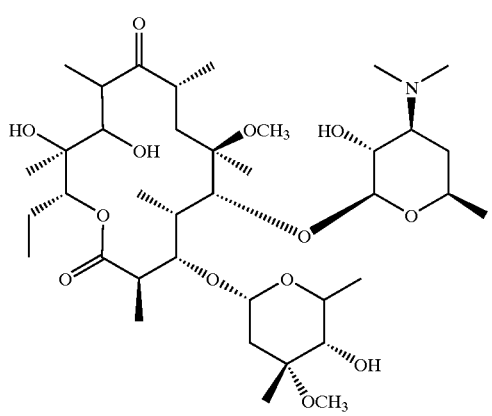

2

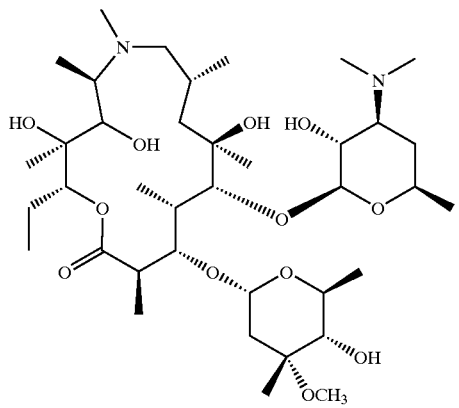

3

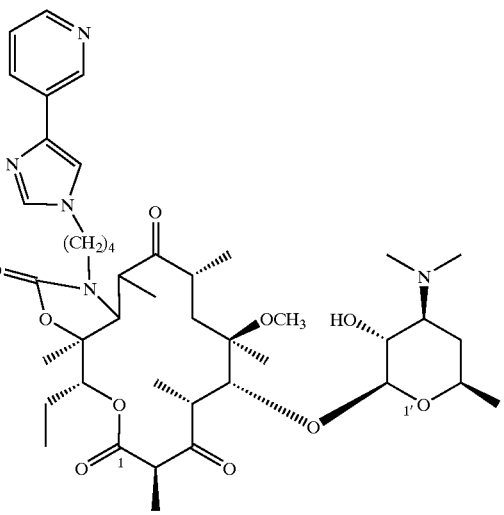

4

Many different semisynthetic third generation derivatives of the ketolide class of macrolide antibiotics have been described, the most potent being HMR 3647 or telithromycin (Compound 4) (EP 680967 A1 (1995); FR 2732684 A1 (1996); Bioorg. Med. Chem. Lett. (1999), 9(21), 3075–3080.) and ABT 773 (WO 9809978 (1998); J. Med. Chem. 2000, 43, 1045). However, none of these agents described thus far have been able to overcome constitutive MLS B resistance in *Staphylococcus aureus*.

SUMMARY OF THE INVENTION

The invention provides new macrolide antibiotics of formula I with improved biological properties, i.e. having the formula

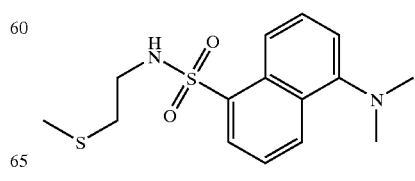

wherein R¹, R² and R³ and as herein described.

The compounds of the present invention are new and possess potent antimicrobial properties against gram positive and selected gram negative organisms. Therefore, they are useful as agents against gram positive pathogens such as *staphylococci, streptococci* and *pneumococci* as well as some gram negative strains such as *H. influenzae* and may be used in human or veterinary medicine for treatment or prevention of infections caused by susceptible organisms.

DETAILED DESCRIPTION OF THE INVENTION

The invention provides new macrolide antibiotics of formula I with improved biological properties, i.e. having the formula

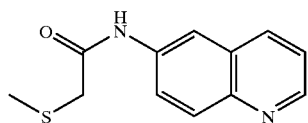

wherein
R¹ is hydrogen, cyano or a residue —Y—X—Q;
Y is S, SO, SO₂, NH, NCH₃, CH₂O, CH₂NH, CH₂NCH₃ or CO;
X is a bond or a linear group with up to 9 atoms consisting of C, N, O and/or S, of which up to 2 atoms can be N, one atom can be O or S, one carbon atom can appear as a CO group, one sulphur atom can appear as an SO₂ group and two adjacent C atoms can be present as —CH═CH— or —C≡C—;
Q is hydrogen, alkyl, heterocyclyl or aryl, which heterocyclyl and aryl groups may be further substituted;
R² is hydrogen or fluorine;
R³ is methyl, —(CH₂)₃—R⁵, —CH₂CH═CH—R⁵ or —CH₂C≡C—R⁵;
R⁵ is heterocyclyl or aryl, which heterocyclyl and aryl groups may be further substituted;
Z is O or NOR⁴;
R⁴ is hydrogen, alkyl, heterocyclyl, aryl, heterocyclylalkyl or aralkyl;
indicates a chiral centre which is in the (R) or (S) form, i.e. including diastereomeric mixtures and separate stereomeric forms,
and pharmaceutically acceptable acid addition salts or in vivo cleavable esters thereof, provided that not simultaneously R² is hydrogen, R³ is methyl and Z is O when simultaneously
R¹ is hydrogen, cyano, —S(L)ₘR⁶, —S(O)(L)ₘR⁶, or —S(O)₂(L)ₘR⁶;
L represents —(CH₂)ₙ— or —(CH₂)ₙZ¹(CH₂)ₙ'—;
m is 0 or 1;
n is 1, 2, 3, or 4;
n' is 0, 1, 2, 3, or 4;
Z¹ is O, S or NH; and
R⁶ is hydrogen, alkyl, heterocyclyl or aryl; which heterocyclyl and aryl groups may be further substituted.

As used herein the term "alkyl" refers to straight or branched chain saturated hydrocarbon group having 1 to 12 carbon atoms, preferably 1 to 6 carbon atoms. Such groups are for example methyl, ethyl, n-propyl, isopropyl, tertiary butyl, pentyl, hexyl, and the like.

The term "halogen" refers to chlorine, bromine or iodine.

The term "aryl" refers to 6-membered, aromatic groups with one or more nuclei from 6 to 14 carbon atoms. Examples are phenyl, naphthyl, anthryl and phenanthryl. These groups may be further substituted with 1,2,3,4 or 5 substituents selected from, for example, phenyl, alkyl, lower alkoxy such as methoxy, ethoxy, propyloxy or n-butoxy, halogen, hydroxy, amino, alkylamino, dialkylamino, nitro or cyano. They can be identical or different from each other. In case more than one substituent is attached to the aryl group, these substituents can be identical or different from each other and are also encompassed by the scope of the present invention. For example dimethoxy-phenyl means that both methoxy substituents may be attached to the phenyl ring in the 2,3-position, the 2,4-position, the 2,5-position, the 2,6-position, the 3,4-position, the 3,5-position and the 3,6-position.

Examples of substituted aryl rings are p-methoxy-phenyl, p-dimethylamino-phenyl, p-cyano-phenyl, 5-(dimethylamino)-1-naphthalenyl, 2,4-dimethoxyphenyl, 2'-methoxy-1,1'-biphenyl, 3,4-dimethylphenyl, As used herein the term "heterocyclyl" refers to an unsaturated or saturated, unsubstituted or substituted 5-, 6-, or 7-membered (mono- or bicyclic) heterocyclic ring system containing at least one hetero atom selected from the group consisting of oxygen, nitrogen, and/or sulfur. Exemplary heterocyclic substituents include, but are not limited to, for example, the following groups:
piperidinyl, morpholinyl, 2-, 3- or 4-pyridyl, pyrrolidinyl, piperazinyl, 1H-pyrazol-1-yl, 1H-imidazol-1-yl, 1H-imidazol-2-yl, pyrazinyl, pyrimidyl, pyridazinyl, pyrazolyl, triazinyl, thiazolyl, thiadiazolyl, oxadiazolyl, triazolyl, e.g. 1H-[1,2,4]-triazol-1-yl, 1H-tetrazolyl, 2H-tetrazolyl; thienyl, furyl (2-furanyl or 3-furanyl), 1H-azepinyl, tetrahydrothiophenyl, 3H-1,2,3-oxathiazolyl, 1,2,3-oxadiazolyl, 1,2,5-oxadithiolyl, isoxazolyl, isothiazolyl, 4H-1,2,4-oxadiazinyl, 1,2,5-oxathiazinyl, 1,2,3,5-oxathiadiazinyl, 1,3,4-thiadiazepinyl, 1,2,5,6-oxatriazepinyl, 1,6,3,4-dioxadithiopanyl, oxazolidinyl, tetrahydrothienyl, and the like, or condensed heterocyclic ring systems such as quinolinyl, e.g. quinolin-8-yl, quinolin-5-yl, quinolin-2-yl, quinolin-6-yl, quinolin-3-yl, isoquinolinyl (6-isoquinolinyl), quinazolinyl, 1H-benztriazolyl, 1H-imidazo[4,5-c]pyridinyl, 5H-imidazo[4,5-c]pyridinyl, 1H-imidazo[4,5-b]pyridin-5-yl, 3H-imidazo[4,5-b]pyridin-3-yl, 1,2,3,4-tetrahydro-quinolinyl, 1,2,3,4-tetrahydro-isoquinolinyl, thieno[2,3-b]pyridinyl, benzothiazolyl (e.g. 2-benzothiazolyl), 1H-benzoimidazolyl, 1H-indolyl, 1,2,3,4-tetrahydroquinolinyl, purinyl, e.g. 9H-purin-9-yl, 6-amino-9H-purin-9-yl, 1H-purin-6-yl, 1H-2,3-dihydroindol-1-yl, 2,1,3-benzoxadiazol-5-yl, 2,1,3-benzoxadiazol-4-yl, 1,3-benzodioxol-5-yl, 2-benzo[b]thien-3-yl, 3,4-dihydro-1H-2-oxo-quinolin-6-yl.

The aryl or heterocyclyl groups may be further substituted by one or more substituents. Such substituents include, for example, alkyl groups such as defined above, alkoxy groups such as methoxy, ethoxy, propyloxy or butyloxy, halogen such as fluorine, chlorine, bromine or iodine, halogen substituted alkyl groups such as trifluoromethyl, trichlroethyl, nitro, amino, alkylamino, dialkylamino, alkylthio, mercapto, hydroxy, carbamoyl, a carboxyl group, an oxo group; or unsubstituted or substituted aryl as defined above; or heterocyclyl.

In case more than one substituent is attached to the heterocyclyl group, these substituents can be identical or different from each other and are also encompassed by the scope of the present invention. For example dimethylpyridyl means that both methyl substituents may be attached to the pyridyl in the chemically possible positions. For example both methyl substituents may be attached to the 2-pyridyl in the 3,4-position, the 4,5-position, the 5,6-position, the 3,5-position, the 3,6-position, the and the 4,6-position. Both methyl substituents may be attached to the 3-pyridyl in the 2,4-position, the 2,5-position, the 2,6-position, the 4,5-position, the 4,6-position, the and the 5,6-position. Both methyl substituents may be attached to the 4-pyridyl in the 2,3-position, the 2,5-position, the 2,6-position, and the 3,5-position.

Examples of substituted heterocyclyl groups are 5-(2-pyridinyl)thien-2-yl, 5-methyl-3-isoxazolyl, 5-cyanopyridin-2-yl; 6-(1H-imidazol-1-yl)-3-pyridinyl, 6-(1H-pyrazol-1-yl)-3-pyridinyl, 6-bromo-2-methyl-quinazolin-4-yl.

Especially preferred substituents for the heterocyclyl groups are alkyl, alkoxy, oxo, amino, alkylamino, dialkylamino or unsubstituted or substituted aryl. Examples of preferred substituted heterocyclic rings are 1H-pyrimidin-2,4-dione-1-yl, 1H,3H-pyrimidin-2,4-dione-5-methyl-1-yl, 1H-pyrimidin-4-amino-2-one-1-yl, 6-amino-9H-purin-9-yl, 6-dimethylamino-9H-purine-9-yl, 4-phenyl-1H-pyrazol-1-yl, 3-(pyridin-3-yl)-1H-pyrazol-1-yl, 3-(pyridin-4-yl)-1H-pyrazol-1-yl, 3-(pyridin-3-yl)-1H-imidazol-1-yl, 3-(pyridin-4-yl)-1H-imidazol-1-yl, 3-(pyridin-3-yl)-1H-[1,2,4]triazol-1-yl, 3-(pyridin-4-yl)-1H-[,1,2,4]triazol-1-yl and 2-oxo-1,2,3,4-tetrahydro-quinolin-6-yl.

In the combinations "heterocyclylalkyl" and "aralkyl" the components "hetero-cyclyl", "ar" (aryl) and "alkyl" have the meanings indicated above.

Preferred groups Q are:

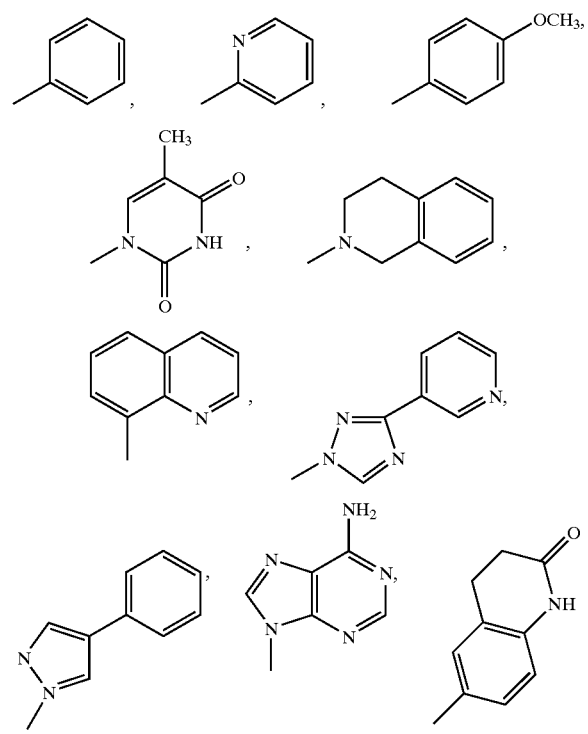

Another preferred group Q is

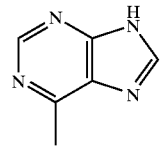

Further preferred groups Q are:

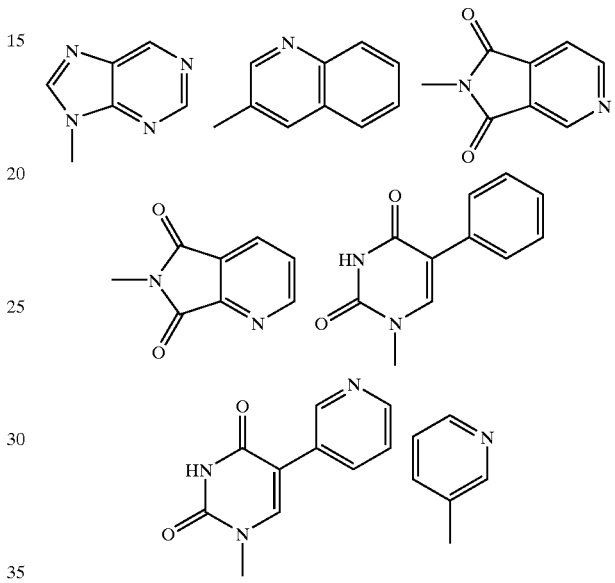

The symbol X represent a bond; i.e. is "absent" or a spacer which is a linear group with up to 9 atoms and defined as above. The linear group with up to 9 atoms may carry additional hydrogen atoms, to saturate a C atom being a methylen group or to saturate a N atom being an amino group. Preferably, this spacer consists of 2 to 5 atoms.

Preferred groups X are:
$(CH_2)_n$, $(CH_2)_mOCH_2$, $(CH_2)_2NCH_3(CH_2)_2$, and $(CH_2)_pCOW$, where n and p are 1–3, m is 0–3 and W is absent or O or NH.

Further preferred groups X are:
$(CH_2)_n$, $(CH_2)_mOCH_2$, $(CH_2)_2NCH_3(CH_2)_2$, $CH_2CH_2NH$ and $(CH_2)_pCOW$, where n and p are 1–3, m is 0–3 and W is absent or O or NH.

Preferred groups Y are:
$S$, $SO_2$ and CO; particularly S.

Further interesting groups Y are:
$CH_2O$, NH and $CH_2NH$.

Combinations of Y and X are:
For Y=S, X is ethyl, propyl, $CH_2CO$, $CH_2COCH_2$, $CH_2CONR$, $CH_2CONRCH_2$, $CH_2CONRCH_2CH_2$, $CH_2CH_2CONR$, $CH_2CH_2CONRCH_2$, $CH_2CH_2NRCO$, $CH_2CH_2NRSO_2$, $CH_2CH_2NRCOO$, $CH_2CH_2OCH_2$, $CH_2SO_2NR$, $CH_2SO_2NRCH_2$, $CH_2CH_2OCONR$, $CH_2CH=CH$ or $CH_2C\equiv C$;

For Y=CO, X is $NRCH_2$, $NRCH_2CH_2$ or $NRCH_2CH_2CH_2$;

For Y=$CH_2O$, X is CONR, $CONRCH_2$, $CH_2CH=CH$ or $CH_2C\equiv C$;

For Y=NH, $CH_2NH$ or $CH_2NHCH_3$, X is $COCH_2$, $COCH_2CH_2$, $COCH_2CH_2CH_2$, COO or $COOCH_2$;

R in the above expressions being hydrogen or methyl.
Preferred group $R^1$ are
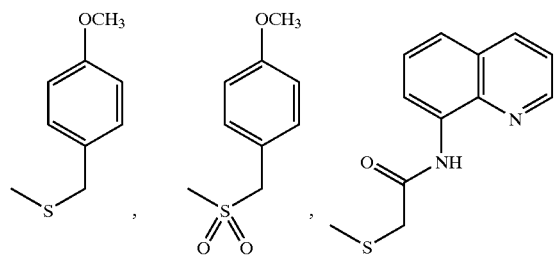
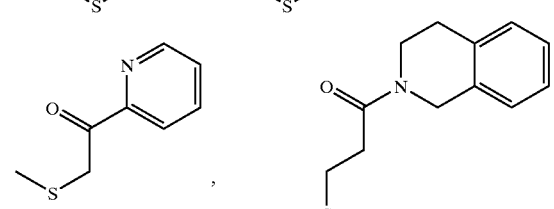
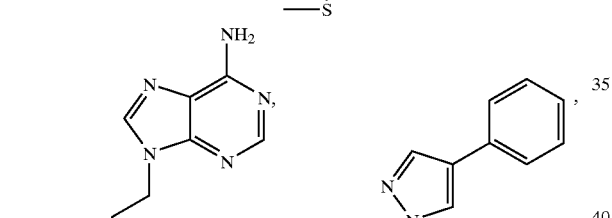
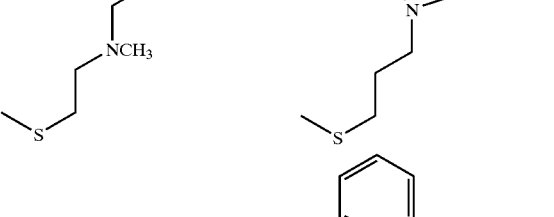
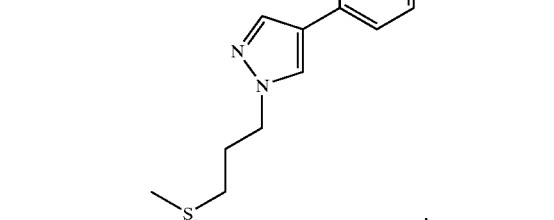
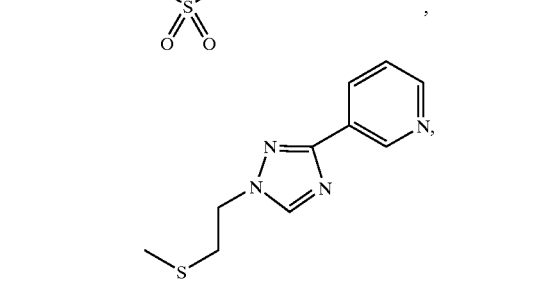
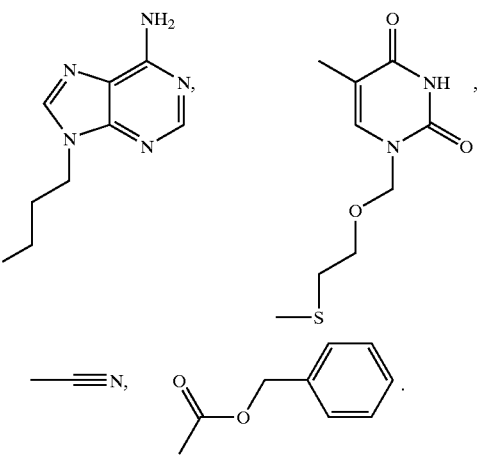
Further preferred groups $R^1$ are
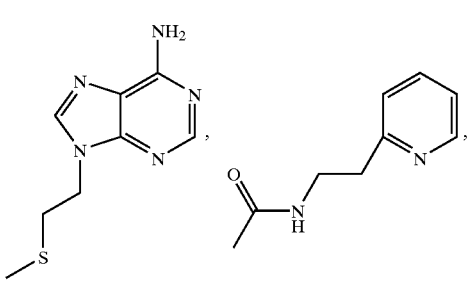
Further interesting group $R^1$ are:
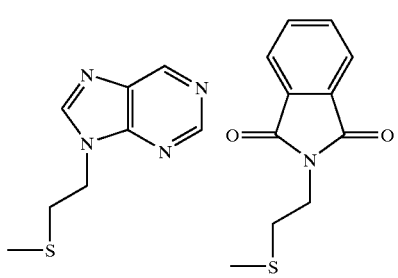

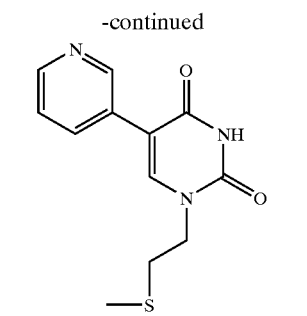
Preferred groups R³ are methyl,
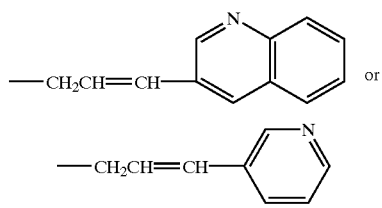
Preferred compounds of formula I are the following:
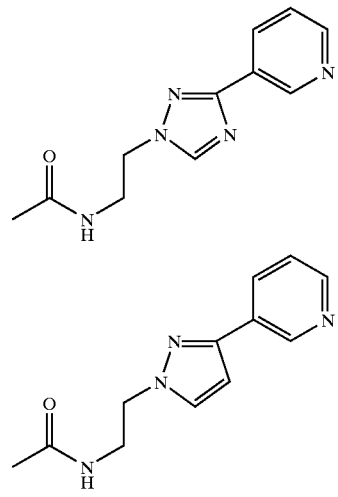
| Example | R¹ | R² | R³ | Z |
|---|---|---|---|---|
| 1 | 4-MeS-CH₂-C₆H₄-OCH₃ | F | Me | O |
| 2 | 4-MeSO₂-CH₂-C₆H₄-OCH₃ | F | Me | O |
| 3 | MeS-S-(3-NO₂-pyridin-2-yl) | H | Me | O |

-continued
| Example | R¹ | R² | R³ | Z |
|---|---|---|---|---|
| 4 | 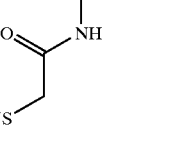 | H | Me | O |
| 5 | 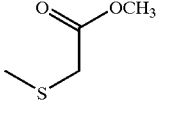 | H | Me | O |
| 6 | 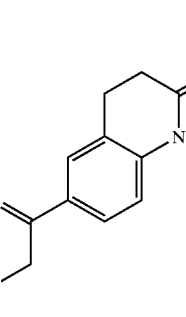 | H | Me | O |
| 7 | 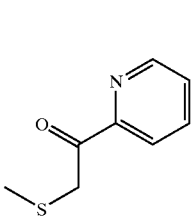 | H | Me | O |
| 8 | 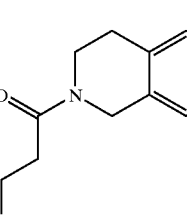 | H | Me | O |
| 9 | 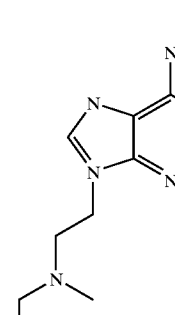 | H | Me | O |

-continued

| Example | R¹ | R² | R³ | Z |
|---|---|---|---|---|
| 10 | 4-phenyl-1H-pyrazol-1-yl with 3-(methylthio)propyl on N | F | Me | O |
| 11 | 4-phenyl-1H-pyrazol-1-yl with 3-(methylsulfonyl)propyl on N | F | Me | O |
| 12 | 3-(pyridin-3-yl)-1H-1,2,4-triazol-1-yl with 2-(methylthio)ethyl on N | F | Me | O |
| 13 | 6-amino-9H-purin-9-yl with 3-(methylthio)propyl on N9 | F | Me | O |
| 14 | thymin-1-yl with (2-(methylthio)ethoxy)methyl on N1 | F | Me | O |

-continued
| Example | R¹ | R² | R³ | Z |
|---------|-----|-----|-----|---|
| 15 |  | H | 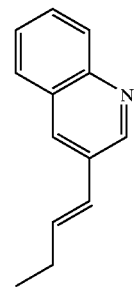 | O |
| 16 | 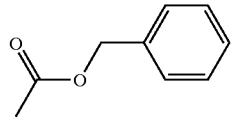 | H | Me | O |
| 17 | 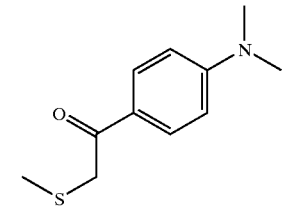 | H | Me | O |
| 18 | 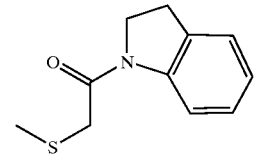 | H | Me | O |
| 19 | 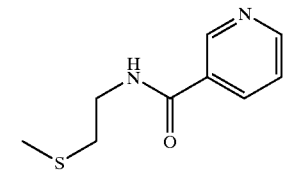 | H | Me | O |
| 20 | 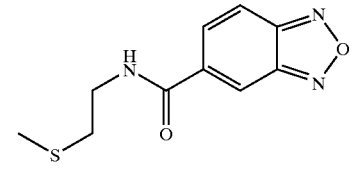 | H | Me | O |
| 21 | 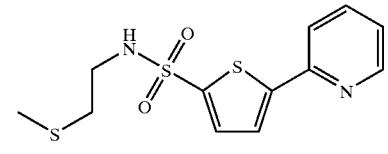 | H | Me | O |
| 22 | 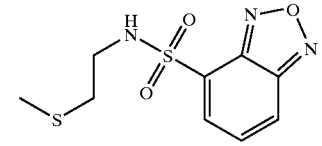 | H | Me | O |

-continued

| Example | R¹ | R² | R³ | Z |
|---|---|---|---|---|
| 23 | 4-cyanophenyl-C≡C-CH₂-S-Me (4-(methylthiomethyl-ethynyl)benzonitrile) | H | Me | O |
| 24 | MeS-CH₂CH₂-S(O)₂-NH-CH₂-Ph (N-benzyl 2-(methylthio)ethanesulfonamide) | H | Me | O |
| 25 | quinolin-8-yl-NH-C(O)-CH₂-SMe | F | Me | O |
| 26 | quinolin-5-yl-NH-C(O)-CH₂-SMe | H | Me | O |
| 27 | quinoline-3-yl-C(O)-NH-CH₂CH₂-SMe | H | Me | O |
| 28 | 5-(dimethylamino)naphthalene-1-sulfonyl-NH-CH₂CH₂-SMe | H | Me | O |
| 29 | quinoline-8-sulfonyl-NH-CH₂CH₂-SMe | H | Me | O |

-continued

| Example | R¹ | R² | R³ | Z |
|---------|----|----|----|----|
| 30 | (methylthio)acetamide-N-CH₂-(benzo[1,3]dioxol-5-yl) | H | Me | O |
| 31 | (methylthio)acetamide-N-CH₂-(furan-2-yl) | H | Me | O |
| 32 | (methylthio)acetamide-N-CH₂-(pyridin-2-yl) | H | Me | O |
| 33 | (methylthio)acetamide-N-(5-methylisoxazol-3-yl) | H | Me | O |
| 34 | (methylthio)acetamide-N-CH₂-(benzothiazol-2-yl) | H | Me | O |
| 35 | (methylthio)acetamide-N-CH₂-(1H-imidazol-2-yl) | H | Me | O |
| 36 | 3-(methylthio)propanamide-N-(quinolin-5-yl) | H | Me | O |
| 37 | (methylthio)acetamide-N-(quinolin-2-yl) | H | Me | O |
| 38 | (methylthio)acetamide-N-(1,5-naphthyridin-6-yl) | H | Me | O |

| Example | R¹ | R² | R³ | Z |
|---|---|---|---|---|
| 39 | (methylthio)acetamide-N-quinolin-3-yl | H | Me | O |
| 40 | (methylthio)acetamide-N-isoquinolin-5-yl | H | Me | O |
| 41 | 3-(methylthio)propanamide-N-quinolin-6-yl | H | Me | O |
| 42 | 3-(methylthio)propanamide-N-quinolin-3-yl | H | Me | O |
| 43 | N-[2-(methylsulfonyl)ethyl]nicotinamide | H | Me | O |
| 44 | N-[2-(methylsulfonyl)ethyl]benzo[1,2,5]oxadiazole-5-carboxamide | H | Me | O |
| 45 | 1-(2,4-dimethoxyphenyl)-2-(methylthio)ethanone | H | Me | O |
| 46 | 6-{[2-(methylthio)ethyl]amino}pyridine-3-carbonitrile | H | Me | O |

-continued

| Example | R¹ | R² | R³ | Z |
|---|---|---|---|---|
| 47 | quinoline-6-carboxamide-N-(2-(methylthio)ethyl) | H | Me | O |
| 48 | 6-(1H-imidazol-1-yl)-N-(2-(methylthio)ethyl)nicotinamide | H | Me | O |
| 49 | quinoline-8-carboxamide-N-(2-(methylthio)ethyl) | H | Me | O |
| 50 | N-(2-(methylthio)ethyl)-6-(1H-pyrazol-1-yl)nicotinamide | H | Me | O |
| 51 | N-(2-(methylthio)ethyl)-9H-purin-6-amine | H | Me | O |
| 52 | 6-bromo-2-methyl-N-(2-(methylthio)ethyl)quinazolin-4-amine | H | Me | O |
| 53 | N-(2'-methoxy-[1,1'-biphenyl]-2-yl)-2-(methylthio)acetamide | H | Me | O |

-continued

| Example | R¹ | R² | R³ | Z |
|---|---|---|---|---|
| 54 | (2-methylthioacetyl)benzothiophene | H | Me | O |
| 55 | N-(3,4-dimethylphenyl)-2-(methylthio)acetamide | H | Me | O |
| 56 | 9-(2-methylthioethyl)adenine | F | Me | O |
| 57 | 9-(3-methylsulfinylpropyl)adenine | F | Me | O |
| 58 | 9-(3-methylsulfonylpropyl)adenine | F | Me | O |
| 59 | N-(2-(pyridin-2-yl)ethyl)acetamide | H | Me | O |

-continued

| Example | R¹ | R² | R³ | Z |
|---------|----|----|----|---|
| 60 | (3-pyridyl-CH₂CH₂-NH-C(=O)-CH₂-) | H | Me | O |

Partcularly preferred are the compounds of Examples 12, 13 and 56.

If desired, compounds of formula I can be converted into a pharmaceutically acceptable acid addition salt. The salt formation is effected at room temperature with methods which are known per se and which are familiar to any person skilled in the art. Not only salts with inorganic acids, but also salts with organic acids come into consideration. Hydrochlorides, hydrobromides, sulfates, nitrates, citrates, acetates, trifluoroacetates, maleates, succinates, methanesulphonates, p-toluenesulphonates and the like are examples of such salts.

Further, the compounds can be converted into in vivo cleavable esters, for example into esters with the 2'-hydroxy group of the sugar moiety, such esters are e.g. acetates, pivaloyl, esters, tartrates, maleates, succinates, and the like. These esters can be prepared according to methods known in the art, for example by reaction with an appropriate anhydride.

The compounds of the present invention and their pharmaceutically acceptable acid addition salts or in vivo cleavable esters thereof are useful as antibacterial therapeutics. Compounds of formula I possess excellent antibacterial activity against selected pathogenic bacteria such as strains of *Staphylococcus aureus* and *Streptococcus pneumoniae*. They can thus be used as medicaments for the treatment of infectious diseases, especially of infections caused by staphylococci such as septicemia, skin and soft tissue infections, deep infections after trauma, surgery, or insertion of foreign material, endocarditis, pneumonia, arthritis, bursitis, and osteomyelitis; or infections caused by streptococci such as septicemia, skin and soft tissue infections, deep infections after trauma, surgery, or insertion of foreign material, endocarditis, tonsillopharyngitis, pneumonia, bronchopneumonia, bronchitis, otitis, sinusitis, and scarlet fever.

Furthermore, the compounds of formula I can be used as medicaments for the treatment of infections caused by germs such as *Moraxella catarrhalis, Haemophiltis*spp., *Neisseria* spp., *Legionella* spp., *Mycoplasma* spp., *Ureaplasma urealyticum, Rickettsia* spp., *Bartonella* spp., *Coxiella burnetti, Chlamydia* spp., or susceptible strains of *Mycobacterium* spp., *Nocardia* spp., and *Actinomyces* spp.

The antibacterial activities of the compounds have been determined by standard microdilution technique (National Committee for Clinical Laboratory Standards. 2000. Methods for Dilution Antimicrobial Susceptibility Tests for Bacteria that Grow Aerobically, $5^{th}$ edition. Approved standard M7-A5. National Committee for Clinical Laboratory Standards, Wayne, Pa.). The activities expressed as the minimum inhibitory concentrations (MICs) (µg/ml) are given in the following Table.

The biological activities of compounds of the present invention against *Haemophilus influenzae* have been determined by standard agar dilution method using HTM medium (National Committee for Clinical Laboratory Standards. 2000. Methods for Dilution Antimicrobial Susceptibility Tests for Bacteria that Grow Aerobically, $5^{th}$ edition. Approved standard M7-A5. National Committee for Clinical Laboratory Standards, Wayne, Pa.). Their MICs along with MICs of selected reference compounds are given in the following Table.

| Microorganism | Code |
|---|---|
| Staphylococcus aureus ATCC 29213 | A |
| Staphylococcus aureus 1086 | B |
| Staphylococcus aureus 745 | C |
| Escherichia coli ATCC 25922 | D |
| Streptococcus pneumoniae 1/1 | E |
| Streptococcus pneumoniae 1/4 | F |
| Streptococcus pneumoniae SL199T | G |
| Streptococcus pneumoniae 12288 | H |
| Haemophilus influenzae QK12/87 | I |
| Haemophilus influenzae 12214 | K |
| Haemophilus influenzae QK50 | L |
| Haemophilus influenzae B1501 | M |

| | Strain | | | | | | | | | | | |
|---|---|---|---|---|---|---|---|---|---|---|---|---|
| Example | A | B | C | D | E | F | G | H | I | K | L | M |
| 1 | 2 | 2 | >32 | >32 | 0.5 | 8 | 32 | >32 | >32 | >32 | 32 | 32 |
| 2 | 2 | 2 | >32 | >32 | <=0.06 | 4 | >32 | >32 | >32 | >32 | 32 | >32 |
| 3 | 2 | 2 | >32 | >32 | <=0.06 | 16 | 32 | >32 | >32 | >32 | >32 | >32 |
| 4 | <=0.06 | <=0.06 | >32 | >32 | <=0.06 | <=0.06 | 1 | 4 | 2 | 2 | 2 | 1 |

-continued

| Example | \multicolumn{12}{c}{Strain} | | | | | | | | | | | |
|---|---|---|---|---|---|---|---|---|---|---|---|---|
| | A | B | C | D | E | F | G | H | I | K | L | M |
| 5 | 1 | 1 | >32 | >32 | 0.125 | >32 | >32 | >32 | 32 | 32 | 32 | 16 |
| 6 | 1 | 1 | >32 | >32 | <=0.06 | >32 | 32 | >32 | >32 | 32 | 32 | 32 |
| 7 | 1 | 0.5 | >32 | >32 | <=0.06 | 32 | 32 | >32 | 32 | 32 | 32 | 32 |
| 9 | 1 | 1 | >32 | >32 | <=0.06 | 0.5 | 8 | 32 | 8 | 16 | 8 | 4 |
| 10 | 0.5 | 0.5 | >32 | >32 | 0.5 | 2 | 8 | 16 | 32 | >32 | 32 | >32 |
| 11 | 0.125 | <=0.06 | >32 | >32 | <=0.06 | 0.25 | 4 | 16 | 8 | 8 | 4 | 4 |
| 12 | <=0.06 | <=0.06 | >32 | >32 | <=0.06 | <=0.06 | 0.25 | 4 | 8 | 4 | 4 | 4 |
| 13 | <=0.06 | <=0.06 | >32 | 32 | <=0.06 | <=0.06 | <=0.06 | 0.25 | 2 | 2 | 2 | 2 |
| 14 | <=0.06 | <=0.06 | >32 | >32 | <=0.06 | 2 | 1 | 16 | 2 | 2 | 2 | 2 |
| 15 | <=0.06 | <=0.06 | 32 | >32 | <=0.06 | 0.25 | 2 | 16 | 4 | 4 | 2 | 2 |
| 16 | nd | nd | nd | Nd | nd | nd | nd | nd | nd | nd | nd | nd |
| 17 | 16 | 8 | >32 | >32 | 1 | >32 | >32 | >32 | >32 | >32 | >32 | >32 |
| 18 | 0.25 | 0.25 | >32 | >32 | <=0.06 | 2 | 16 | >32 | 8 | 8 | 8 | 8 |
| 19 | 0.25 | 0.25 | >32 | >32 | 0.125 | 2 | 32 | >32 | 4 | 4 | 8 | 4 |
| 20 | <=0.06 | <=0.06 | >32 | >32 | <=0.06 | 0.5 | 8 | >32 | 2 | 2 | 4 | 2 |
| 21 | 0.125 | 0.125 | >32 | >32 | <=0.06 | 8 | 16 | 32 | 32 | 16 | 16 | 16 |
| 22 | <=0.06 | <=0.06 | >32 | >32 | <=0.06 | 8 | 8 | >32 | 4 | 4 | 4 | 4 |
| 23 | 16 | 16 | >32 | >32 | 1 | >32 | >32 | >32 | >32 | >32 | >32 | >32 |
| 24 | 2 | 1 | >32 | >32 | <=0.06 | >32 | 32 | >32 | 32 | >32 | >32 | 32 |
| 25 | 0.25 | 0.125 | 32 | >32 | <=0.06 | 0.125 | 2 | 4 | 8 | 4 | 4 | 8 |
| 26 | 0.25 | 0.25 | >32 | >32 | <=0.06 | 0.125 | 1 | 4 | 4 | 2 | 2 | 4 |
| 27 | <=0.06 | <=0.06 | >32 | >32 | <=0.06 | 8 | 8 | >32 | 16 | 16 | 16 | 8 |
| 28 | 1 | 1 | >32 | >32 | <=0.06 | 32 | 16 | >32 | 32 | >32 | 32 | >32 |
| 29 | <=0.06 | <=0.06 | >32 | >32 | <=0.06 | >32 | 2 | >32 | 8 | 8 | 8 | 8 |
| 30 | 0.125 | <=0.06 | >32 | >32 | <=0.06 | 32 | 16 | >32 | 16 | 16 | 16 | 8 |
| 31 | 0.5 | 0.25 | >32 | >32 | <=0.06 | >32 | 32 | >32 | 8 | 8 | 8 | 8 |
| 32 | 1 | 0.5 | >32 | >32 | <=0.06 | >32 | 32 | >32 | 8 | 8 | 8 | 8 |
| 33 | 0.5 | 0.5 | >32 | >32 | <=0.06 | >32 | 32 | >32 | 16 | 8 | 8 | 8 |
| 34 | 0.25 | 0.5 | >32 | >32 | <=0.06 | 8 | >32 | >32 | 32 | >32 | >32 | 32 |
| 35 | 8 | 8 | >32 | >32 | <=0.06 | >32 | 16 | >32 | 16 | 32 | 16 | 16 |
| 36 | 0.125 | 0.125 | >32 | >32 | <=0.06 | 0.125 | 2 | 16 | 8 | 8 | 4 | 4 |
| 37 | 0.125 | <=0.06 | >32 | >32 | <=0.06 | 4 | >32 | >32 | 8 | 16 | 8 | 8 |
| 38 | <=0.06 | <=0.06 | >32 | >32 | <=0.06 | 4 | 8 | 32 | 8 | 16 | 16 | 8 |
| 39 | <=0.06 | <=0.06 | >32 | >32 | <=0.06 | 32 | 8 | 32 | 16 | 16 | 16 | 8 |
| 40 | 0.125 | 0.125 | >32 | >32 | <=0.06 | 0.125 | 0.5 | 4 | 4 | 4 | 4 | 4 |
| 41 | <=0.06 | <=0.06 | >32 | >32 | <=0.06 | 16 | 8 | >32 | 8 | 8 | 16 | 8 |
| 42 | 0.125 | 0.125 | >32 | >32 | <=0.06 | 32 | 32 | >32 | 16 | 16 | 16 | 16 |
| 43 | 2 | 1 | >32 | >32 | nd | nd | 32 | >32 | 16 | 16 | 16 | 8 |
| 44 | 0.5 | 0.125 | >32 | >32 | <=0.06 | <=0.06 | 16 | >32 | 16 | 16 | 16 | 8 |
| 45 | 0.25 | 0.25 | >32 | >32 | <=0.06 | 0.5 | 16 | >32 | 8 | 8 | 8 | 4 |
| 46 | <=0.06 | <=0.06 | >32 | >32 | <=0.06 | <=0.06 | 4 | 32 | 1 | 2 | 4 | 1 |
| 47 | 0.125 | <=0.06 | >32 | >32 | <=0.06 | <=0.06 | 8 | >32 | 4 | 8 | 4 | 2 |
| 48 | 0.25 | 0.25 | >32 | >32 | <=0.06 | >32 | >32 | >32 | 16 | 32 | 16 | 16 |
| 49 | <=0.06 | <=0.06 | >32 | >32 | <=0.06 | <=0.06 | 2 | 16 | 4 | 16 | 4 | 4 |
| 50 | 0.25 | 0.125 | >32 | >32 | <=0.06 | 32 | 32 | >32 | 8 | 16 | 8 | 4 |
| 51 | 1 | 1 | >32 | 32 | <=0.06 | 0.125 | 0.5 | 8 | 1 | 4 | 1 | 2 |
| 52 | 0.125 | <=0.06 | >32 | >32 | <=0.06 | 0.125 | 4 | 8 | 8 | 16 | 8 | 8 |
| 53 | 0.5 | 0.25 | >32 | >32 | <=0.06 | 1 | 16 | >32 | 8 | 16 | 8 | 16 |
| 54 | 1 | 0.5 | >32 | >32 | <=0.06 | 32 | >32 | >32 | 16 | 16 | 32 | 8 |
| 55 | 0.25 | 0.125 | >32 | >32 | <=0.06 | <=0.06 | 0.25 | 2 | 8 | 8 | 16 | 8 |
| 56 | <=0.06 | <=0.06 | >32 | 32 | <=0.06 | <=0.06 | <=0.06 | 1 | 1 | 1 | 0.5 | 0.5 |
| 57 | 2 | 2 | >32 | >32 | <=0.06 | 0.125 | 1 | 32 | 4 | 8 | 8 | 4 |
| 58 | 0.5 | 0.5 | >32 | >32 | <=0.06 | <=0.06 | 0.5 | 8 | 4 | 4 | 4 | 4 |
| 59 | nd | nd | nd | Nd | nd | nd | nd | nd | nd | nd | nd | nd |
| 60 | nd | nd | nd | Nd | nd | nd | nd | nd | nd | nd | nd | nd |
| References | | | | | | | | | | | | |
| Erythromycin | 0.25 | >32 | >32 | >32 | <=0.06 | >32 | >32 | >32 | 4 | 4 | 8 | 4 |
| Clarithromycin | 0.125 | >32 | >32 | >32 | <=0.06 | 32 | >32 | >32 | 4 | 4 | 8 | 4 |

The compounds in accordance with the invention can be used as medicaments. They possess good oral absorption properties. A further embodiment of the present invention are thus medicaments comprising compounds of formula I, their pharmaceutically acceptable acid addition salts or in vivo cleavable esters thereof for the treatment and prevention of infectious diseases, for example, in the form of pharmaceutical preparations for enteral (oral) administration. The products in accordance with the invention can be administered, for example, perorally, such as in the form of tablets, coated tablets, dragees, hard and soft gelatin capsules, solutions, emulsions or suspensions, or rectally, such as in the form of suppositories, or parenterally e.g. by injection, or locally for example by topical administration, preferably the compounds are administered orally.

Pharmaceutical compositions containing these compounds can be prepared using conventional procedures familiar to those skilled in the art, such as by combining the ingredients into a dosage form together with suitable, non-toxic, inert, therapeutically compatible solid or liquid carrier materials and, if desired, the usual pharmaceutical adjuvants.

It is contemplated that the compounds are ultimately embodied into compositions of suitable oral, parenteral or topical dosage forms. The compositions of this invention can contain, as optional ingredients, any of the various adjuvants which are used ordinarily in the production of pharmaceutical preparations. Thus, for example, in formulating the present compositions into the desired oral dosage forms, one may use, as optional ingredients, fillers, such as coprecipitated aluminum hydroxide-calcium carbonate, dicalcium phosphate or lactose; disintegrating agents, such as maize starch; and lubricating agents, such as talc, calcium stearate, and the like. It should be fully understood, however, that the optional ingredients herein named are given by way of example only and that the invention is not restricted to the use hereof. Other such adjuvants, which are well known in the art, can be employed in carrying out this invention.

Suitable as such carrier materials are not only inorganic, but also organic carrier materials. Thus, for tablets, coated tablets, dragees and hard gelatin capsules there can be used, for example, lactose, maize starch or derivatives thereof, talc, stearic acid or its salts. Suitable carriers for soft gelatin capsules are, for example, vegetable oils, waxes, fats and semi-solid and liquid polyols (depending on the nature of the active substance; no carriers are, however, required in the case of soft gelatin capsules). Suitable carrier materials for the preparation of solutions and syrups are, for example, water, polyols, saccharose, invert sugar and glucose. Suitable carrier materials for suppositories are, for example, natural or hardened oils, waxes, fats and semi-liquid or liquid polyols.

As pharmaceutical adjuvants there are contemplated the usual preservatives, solubilizers, stabilizers, wetting agents, emulsifiers, sweeteners, colorants, flavorings, salts for varying the osmotic pressure, buffers, coating agents and antioxidants.

The compounds of formula I and their acid addition salts or in vivo cleavable esters thereof can be used for parenteral administration and for this purpose are preferably made into preparations for injection as lyophilisates or dry powders for dilution with customary agents, such as water or isotonic common salt solution.

The compounds of formula I and their acid addition salts or in vivo cleavable esters thereof can be used for topical administration and for this purpose are preferably made into preparations as ointments, cremes or gels.

For the prevention and treatment of infectious diseases in mammals, human and non-human, a daily dosage of about 10 mg to about 2000 mg, especially about 50 mg to about 1000 mg, is usual, with those of ordinary skill in the art appreciating that the dosage will depend also upon the age, conditions of the mammals, and the kind of diseases being prevented or treated. The daily dosage can be administered in a single dose or can be divided over several doses. An average single dose of about 100 mg, 250 mg, 500 mg and 1000 mg can be contemplated.

The compounds of the present invention can be prepared by deacylating a compound of the general formula

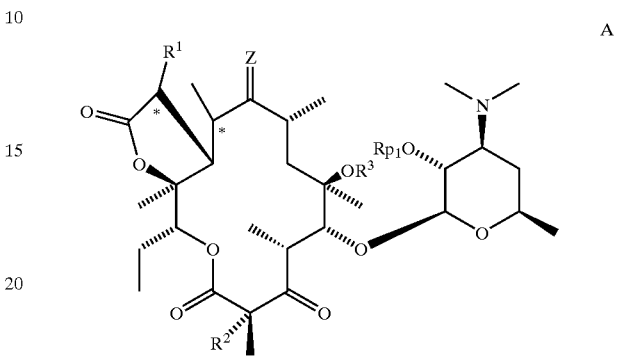

A wherein $R^1$—$R^3$, Z and * are as above and $Rp_1$ is acetyl or benzoyl, and, if desired, converting the compound of formula I obtained into a pharmaceutically acceptable acid addition salt or into an in vivo cleavable ester thereof.

The reaction steps starting from known compounds leading to the starting compounds of formula A and the end products of formula I are carried out according to the following schemes 1–11. In the general discussion and the working examples that follow, certain abbreviations are used; those include:

TLC for thin layer chromatography;
HPLC for high performance liquid chromatography;
DMSO for dimethylsulphoxide;
DBU for 1,8-diazabicyclo[5.4.0]undec-7-ene;
DIPEA for diisopropylethylamine (Huenig's base);
DIAD for diisopropylazadicarboxylate;
DMF for dimethylformamide;
THF for tetrahydrofuran;
DCC for dicyclohexylcarbodiimide;
DMAP for 4-dimethylaminopyridine;
EDC.HCl for N-(3-dimethylaminopropyl)-N'-ethylcarbodiimide hydrochloride;
$R_f$ indicates the retention of the compound on thin layer chromatography;
KO'Bu for potassium tert.-butylate;
MS for mass spectrometry;
NMR for nuclear magnetic resonance;
ISP for ion spray.

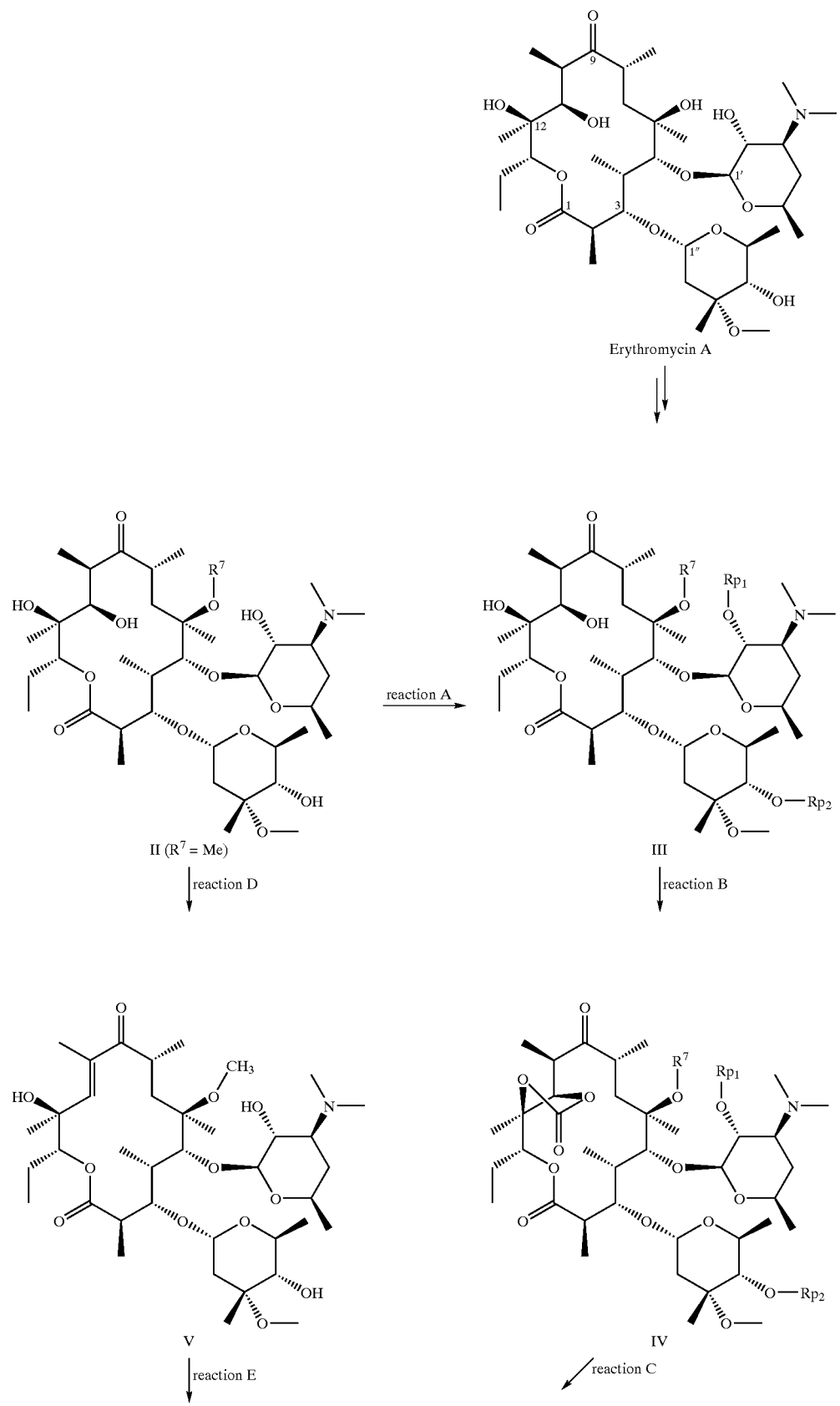

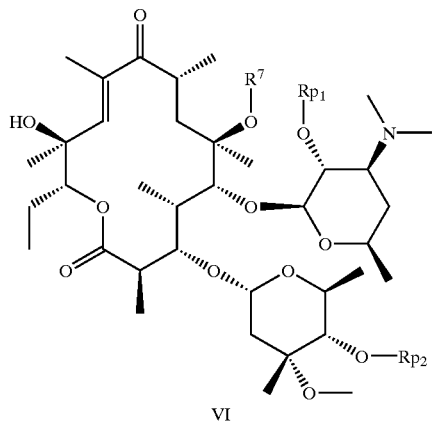

VI

The compounds of the present invention can be prepared by methods well known in the art e.g. by chemical modification of the readily available intermediate of the formula VI (scheme 1) wherein $Rp_1$ can be for example acetyl, benzoyl or the like, $Rp_2$ acetyl, benzoyl, benzyloxycarbonyl or the like and $R^7$ methyl, allyl or propargyl. Compounds of formula VI can be prepared either from erythromycin or from clarithromycin according to published procedures.

Compounds of formula III wherein $R^7$ is allyl or propargyl and $Rp_1$ and $Rp_2$ as defined above can be prepared from erythromycin by methods described in, for example, Clark et al., Bioorg. Med. Chem. Lett. 2000, 10, 815–819 and WO 0078773. To obtain compounds of formula III wherein $R^7$ is methyl and $Rp_1$ and $Rp_2$ as defined above the 2'- and 4"-hydroxyl groups of commercially available clarithromycin can be protected either sequentially or simultaneously by reaction with a suitable acid anhydride or acid chloride (reaction A, scheme 1) as described in, for example, Baker et al., J. Org. Chem. 1988, 53, 2340–2345 and Kashimura et al., J. Antibiotics, 2001, 54, 664–678. Compounds of formula III can then be transformed into compounds of formula VI (reactions B and C) in a similar way as described in Baker et al., J. Org. Chem. 1988, 53, 2340–2345. Alternatively, compounds of formula VI with $R^7=CH_3$ can also be obtained by treating clarithromycin (II, $R^7=CH_3$) with ethylencarbonate in refluxing triethylamine (reaction D) as described for example in Elliott et al., J. Med. Chem., 1998, 41, 1651–1659 or by treating clarithromycin with ethylenecarbonate and a base such as potassium carbonate in hot DMF, preferably at 110° C. and subsequent protection of the 2'- and 4"- hydroxyl groups by reaction with a suitable acid anhydride in an aprotic solvent (reaction E) similar to the procedure described for example in Kashimura et al., J. Antibiotics, 2001, 54, 664–678.

Scheme 2.

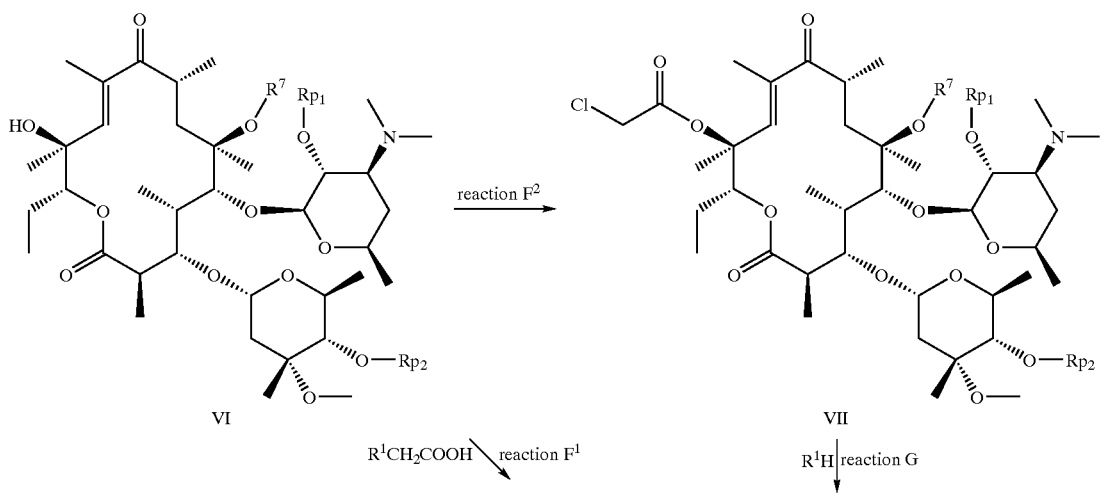

-continued
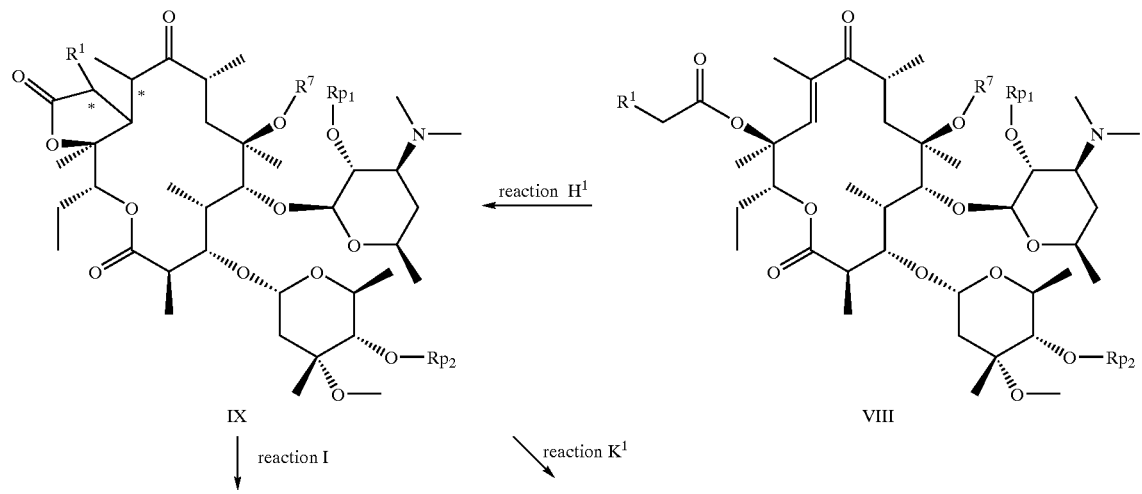
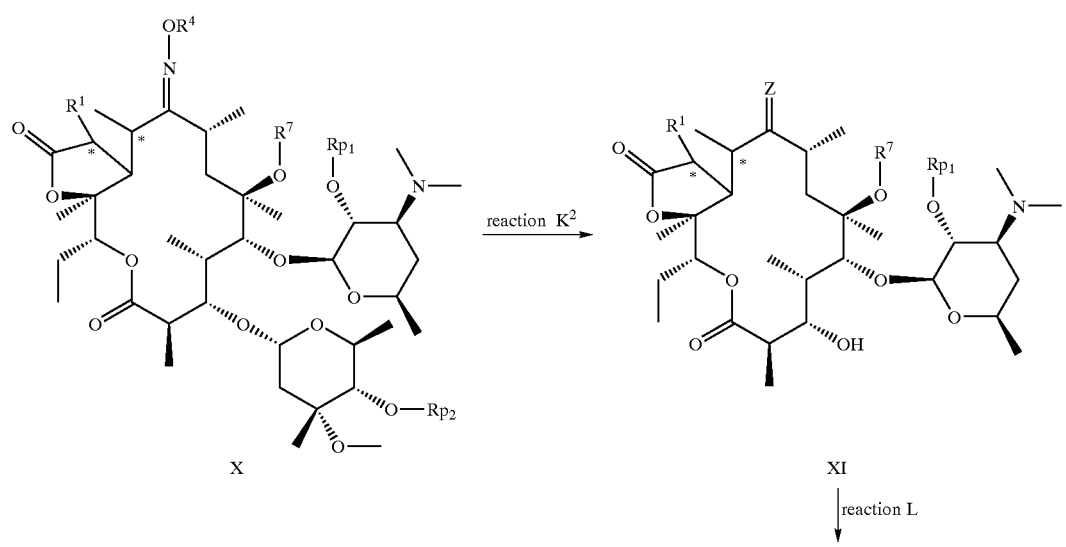
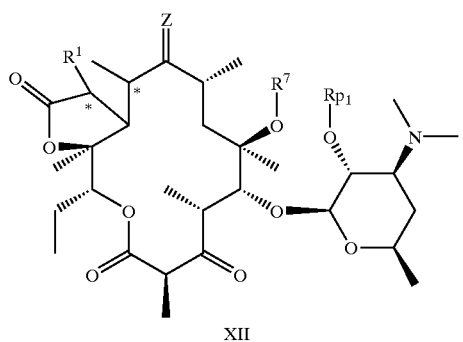

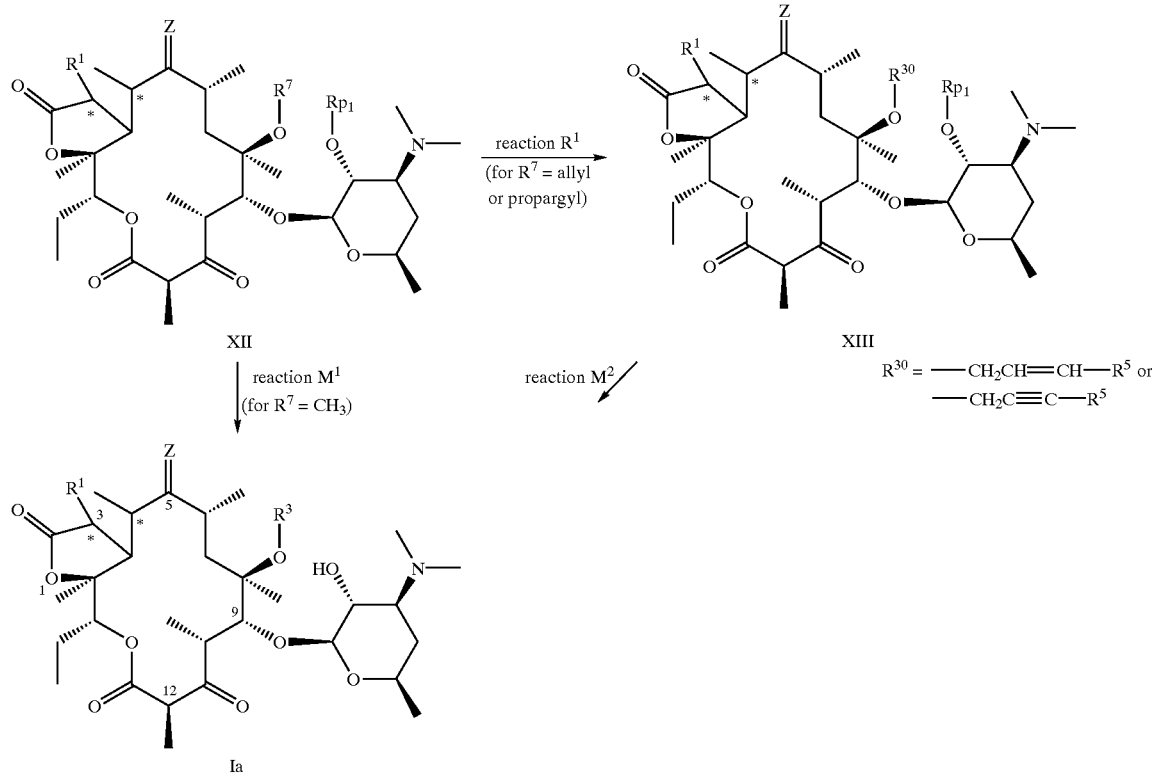

Compounds of formula VI can then be further reacted as summarized in scheme 2:

The hydroxy group at position 12 of compounds of formula VI is esterified by treatment with an appropriate carboxylic acid ($R^1CH_2COOH$), DCC and DMAP in a chlorinated solvent such as methylene chloride (reaction $F^1$, scheme 2). Depending on the nature of $R^1$ compounds of formula VIII can also be synthesised via a two step procedure where the hydroxy group at position 12 is first reacted with 2-chloro acetic acid as described above (reaction $F^2$) to give compounds of formula VII. The intermediate is then treated with the appropriate nucleophile $R^1H$ in acetone in the presence of a base such as DBU (reaction $G^1$) to give compounds of formula VIII. If compounds of formula VII are treated with tetrabutylammonium cyanide, compounds of formula IX wherein $R^1$ is cyano are obtained directly in one step without the addition of any base. Compounds of formula VIII are treated with an alkali metal base such as NaH or potassium tert.-butoxide in a aprotic solvent such as DMF or THF (reaction $H^1$) to give compounds of formula IX as mixture of diastereoisomers in various ratios.

To prepare compounds of formula XI wherein Z=O the intermediate IX is treated with 1% to 5% HCl in an alcoholic solvent e.g. methanol or ethanol, at room temperature (reaction $K^1$). To obtain compounds of formula XI wherein Z=$NOR^4$ compounds IX are first reacted with an appropriate hydroxylamine ($R^4ONH_2$) in a solvent such as ethanol, iso-propanol, butanol or pyridine at temperatures ranging from 80° C. to 120° C. for 12 hours to 72 hours (reaction I) to give compounds of formula X as described for example in EP 1088828 or EP 1132392. These intermediates are subsequently treated as described above (reaction $K^2$) in order to obtain compounds of formula XI wherein Z=$NOR^4$. The oxidation of compounds XI is carried out with EDC*HCl, DMSO and pyridinium trifluoroacetate in a chlorinated solvent such as methylene chloride or using 1,1,1-triacetoxy-1,1-dihydro-1,2-benziodoxol-3-(1H)-one (Dess-Martin reagent) in a chlorinated solvent such as methylene chloride to give compounds of formula XII (reaction $L'$). Compounds of formula XII can then be further reacted according to schemes 3 and 4 if appropriate or deprotected (for $R^7$=$CH_3$) by stirring in an alcoholic solvent such as methanol or ethanol for 12 to 72 hours at temperatures ranging from 20° C. to 80° C. to give free 2'-hydroxy compound of formula I as a single diastereoisomer (reaction $M^1$).

Where $R^7$ is allyl or propargyl the group $R^5$ is introduced in accordance with process variant $R^1$ to yield compounds XIII by means of a so-called "Heck reaction" (for $R^7$=allyl in XII) or a so called "Sonogashira reaction" (for $R^7$=propargyl in XII). In the case of the "Heck reaction" compounds of formula XIII are obtained by reacting a compound XII with compounds Lg-$R^5$, where $R^5$ is defined as before and Lg represents a leaving group, for example bromine, iodine, methanesulphonoxy, trifluoromethanesulphonoxy, benzenesulphonyloxy or p-toluenesulphonyloxy. Preferably, an inert organic solvent, e.g. dioxane, tetrahydrofuran, N,N-dimethylacetamide or N,N-dimethylformamide, is used. The reaction is preferably effected in the presence of a base such as alkali metal carbonate, and/or a tertiary amine, e.g. a tri(lower alkyl)amine such as triethylamine, tri-n-butylamine, diisopropylethylamine or N-ethylpiperidine, and together with a catalyst, preferably a palladium complex, such as palladium(II) acetate, bis(triphenylphosphine) palladium(II)dichloride, bis(triphenyl-phosphine)palladium (II) diacetate, tetrakis (triphenylphosphine)

palladium, and triphenylphosphine or tri-o-tolylphosphine, optionally with the addition of a phase transfer catalyst such as a tetraalkylammonium salt, e.g. tetrabutylammonium bromide. The temperature of the "Heck reaction" preferably lies in the region between about 40° C. and the boiling point of the reaction mixture.

In the case of the "Sonogashira reaction" compounds of formula XIII are obtained by reacting a compound XII with $R^7$=propargyl with compounds Lg-$R^5$, where $R^5$ is defined as before and Lg represents a leaving group, for example bromine, iodine, methanesulphonoxy, trifluoromethanesulphonoxy, benzene-sulphonyloxy or p-toluenesulphonyloxy. Preferably, an inert organic solvent, e.g. dioxane, tetrahydrofuran, N,N-dimethylacetamide or N,N-dimethylformamide, is used. The reaction is preferably effected in the presence of a base such as a secondary amine, e.g. diethylamine or di-isopropylamine, or a tertiary amine, e.g. a tri(lower alkyl)amine such as triethylamine, tri-n-butylamine, düsopropyl-ethylamine or N-ethylpiperidine, and together with a catalyst, preferably a palladium complex, such as palladium(II) acetate, bis(triphenylphosphine) palladium(II)dichloride, bis(triphenylphosphine)palladium (II) diacetate, tetrakis(triphenylphosphine) palladium, copper(I) iodide and triphenylphosphine or tri-o-tolylphosphine, optionally with the addition of a phase transfer catalyst such as a tetraalkylammonium salt, e.g. tetrabutylammonium bromide. The temperature of the "Sonogashira reaction" preferably lies in the region between about 0° C. and the boiling point of the reaction mixture, preferably room temperature.

The so-obtained "Heck" and "Sonogashira" products XIII, viz. where $R^{30}$ is —$CH_2CH$=$CH$—$R^5$ or —$CH_2C$≡$C$—$R^5$, can be saturated to $R^3$=—$(CH_2)_3$—$R^5$ by catalytic hydrogenation with a palladium catalyst in a lower alkanol such as ethanol or in ethyl acetate at a temperature between about 0° C. and 80° C., preferably at room temperature.

Deprotection of compounds XIII (reaction $M^2$) as for reaction $M^1$ above yields free 2'-hydroxy compounds Ia.

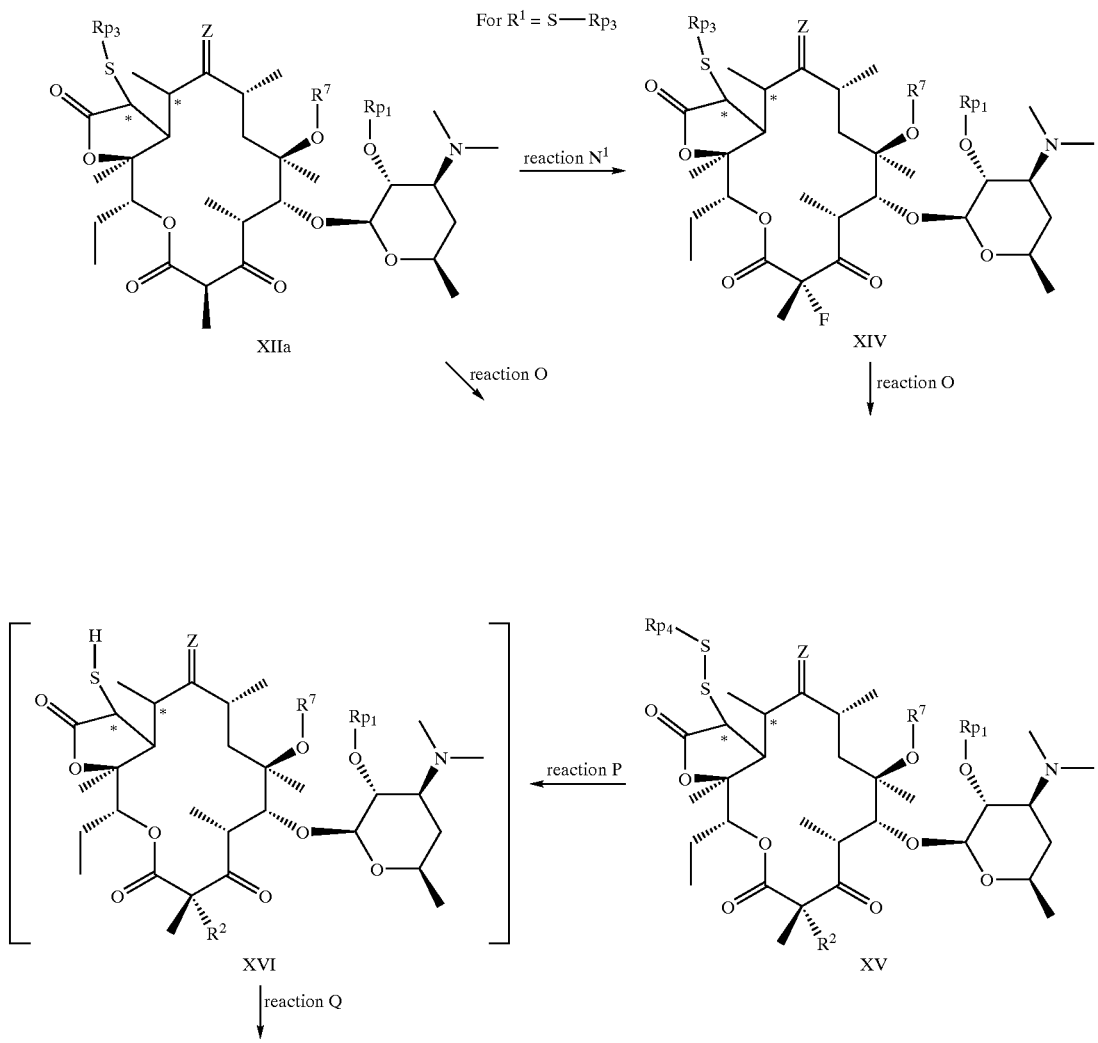

Scheme 3.

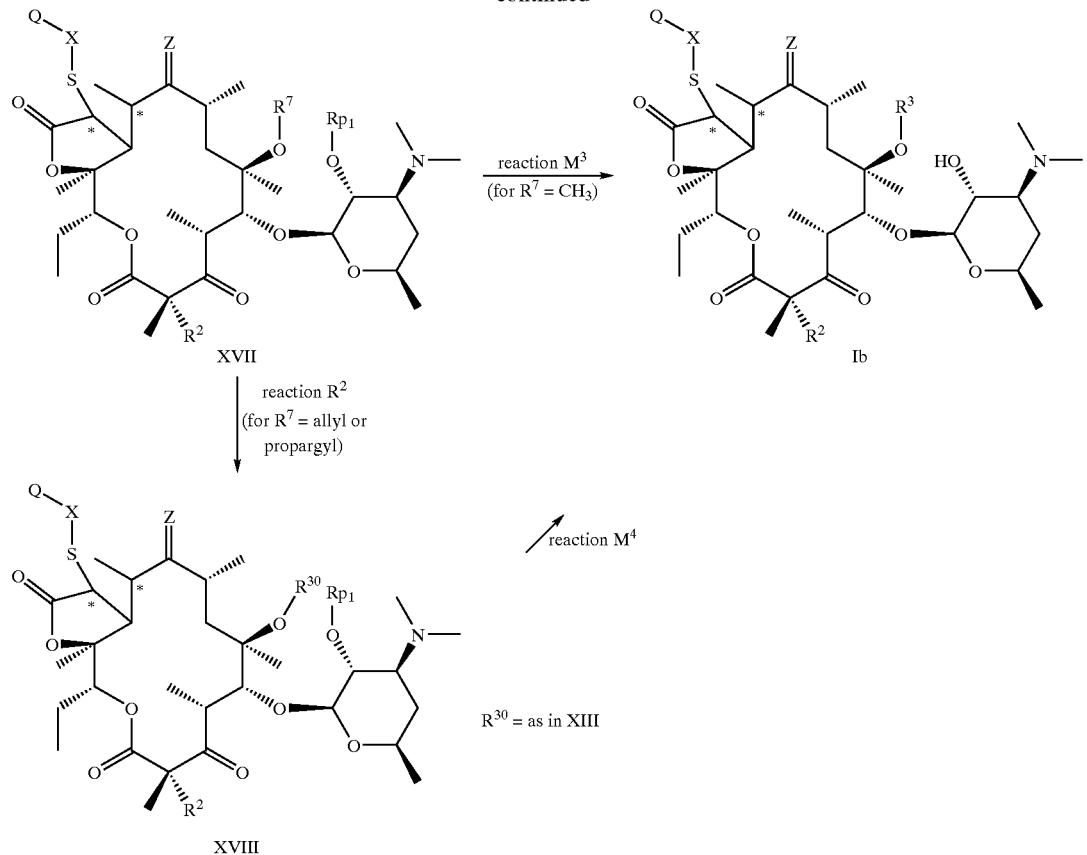

In scheme 3, according to reaction O, compound XII in which $R^1$ is —S—$Rp_3$ and $Rp_3$ is a sulfur protective group, e.g. benzyl, 4-methoxybenzyl, 3,4-dimethoxybenzyl or 4-nitro-benzyl, preferably 4-methoxybenzyl, and Z, $Rp_1$ and $R^7$ are defined as before (compound XIIa) is treated with a sulfur-alkylating agent, preferably 3-nitro-2-pyridylsulfenyl chloride in dichloromethane in the presence of an organic acid, preferably trifluoroacetic acid, at 0° C. to room temperature for 20 min to 24 hours, preferably for 1 hour, to prepare the bisulfide compound XV with $Rp_4$ e.g. 3-nitro-2-pyridinyl. Compound XIIa can also be treated with dimethyl(methylthio)sulfonium tetrafluoroborate in an organic solvent like methanol, dimethylformamid or dichloromethane in the presence of traces of water at 0° C. to room temperature for 1 hour to 24 hours, preferably 6 hours to obtain compound XV where $Rp_4$=methyl. (Analogous treatment applied for other alkyls $Rp_4$).

According to reaction P, a compound of formula XV is treated with a reducing agent such as a trialkyl phosphine, preferably tributyl phosphine, or a triaryl phosphine, preferably triphenyl phosphine in a solvent such as aqueous acetone, aqueous dimethyl formamide, aqueous dioxane or aqueous tetrahydrofuran, preferably aqueous dimethyl formamide, at 0° C. to 60° C., preferably at room temperature for 1 minute to 1 hour, preferably 15 minutes, to give compound XVI.

According to reaction Q, Compound XVI is treated, preferably without isolation, directly in the same solvent system as in reaction P with compounds of the formula Q—X—Lg, in which Q and X are defined as before and Lg is a leaving group, e.g. chloride, bromide, iodide, methanesulfonyloxy, p-tosylsulfonyloxy, trifluorethansulfonyloxy or a vinyl group in the case where X represents a carbonyl or a sulfonyl group. The reaction is preferably effected in the presence of a base such as alkali metal carbonate or hydrogen carbonate, e.g. potassium carbonate, cesium carbonate or sodium hydrogen carbonate, or an organic base, e.g. triethylamine, N-ethyl N,N-diisopropylamine, 1,8-diazabicyclo[5.4.0]undec-7-ene or 1,5-diazabicyclo[4.3.0]non-5-en, preferably 1,8-diazabicylo [5.4.0]undec-7-ene at temperature between 0° C. and 50° C., preferably at 20° C. It can be advantageous to add catalytic amounts of an iodide salt, preferably sodium iodide, to the reaction mixture.

Introduction of fluorine (reaction $N^1$) at position 12 of compound XIIa is carried out by the methods known to the art by treatment of XIIa with strong bases like sodium hydride, potassium hydride, lithium diisopropylamide, lithium hexamethyldisilylamide, sodium hexamethyldisilylamide or potassium tert-butoxide, preferably sodium hydride or potassium t-butoxide, and a fluorinating agent like N-Fluor-bis-(phenylsulfonyl)-amine or 1-chloromethyl-4-fluoro-1,4-diazonia-bicyclo[2.2.2]octane bis-(tetrafluoroborate) (Selectfluor). This reaction is preferably effected in an inert organic solvent like diethylether, tetrahydrofuran, or dimethyl formamide, preferably dimethylformamide at temperature between about −80° C. and +20° C., preferably −20° C. under an inert athmosphere.

Compounds XVII are converted into compounds Ib by deprotection reaction $M^3$ or "Heck"/"Sonogashira" reactions $R^2$ and deprotection reaction $M^4$, this in analogy to the above reactions $M^1$, $R^1$ and $M^2$ in Scheme 2.

for 1 hour to 24 hours preferably 6 hours to obtain compounds of formula XIX as a mixture of diastereoisomers in

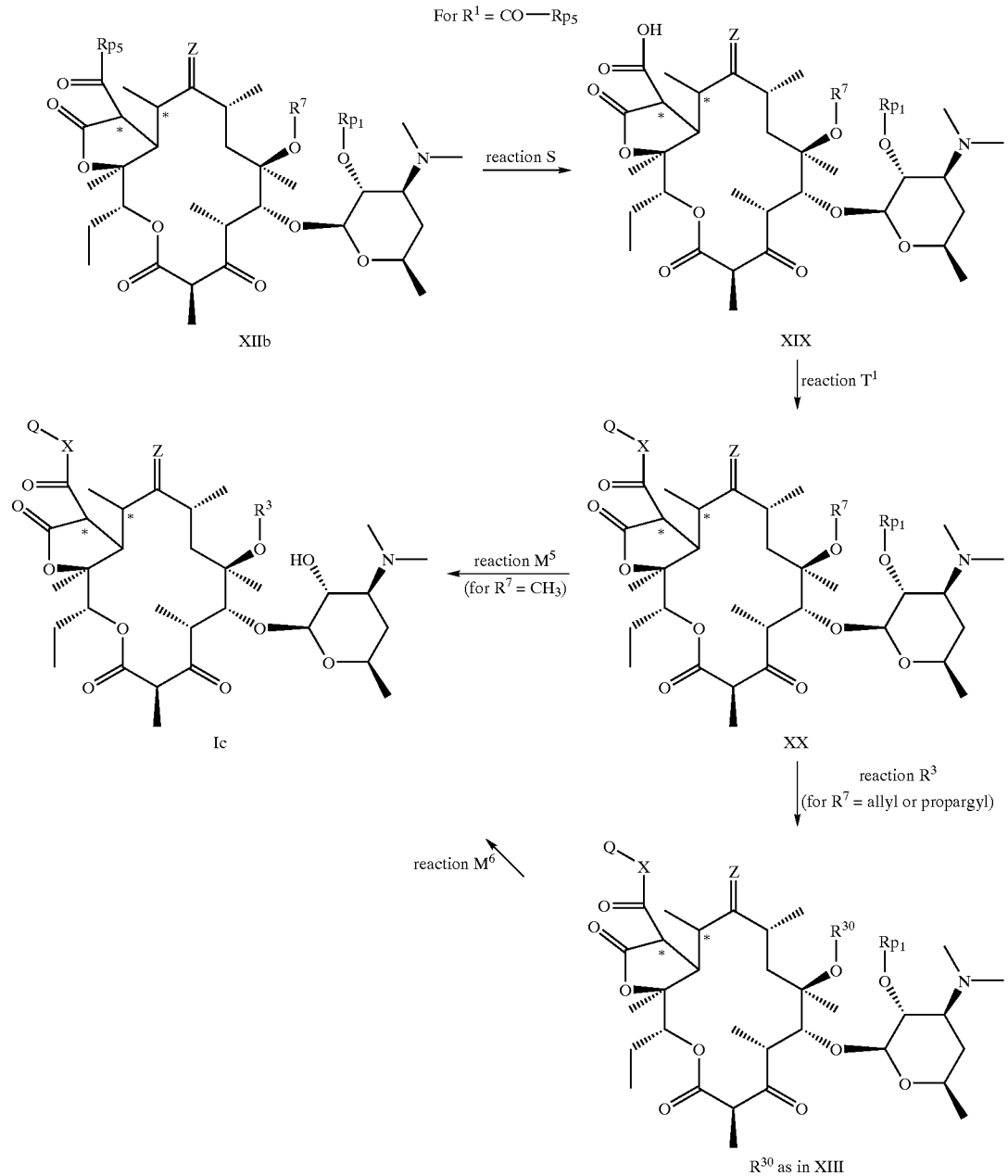

Scheme 4

Compounds of formula XII wherein $R^1$ is CO—$Rp_5$ and $Rp_5$ represents benzyloxy, p-methoxybenzyloxy, methoxy or t-butyloxy and $Rp_1$, $R^7$ and Z are as defined above (compounds XIIb) can be further elaborated as described in scheme 4. In the first step (reaction S) the ester moiety is cleaved in the case of $Rp_5$=benzyloxy and p-methoxybenzyloxy by treating with $H_2$ gas in the presence of a catalyst such as palladium on charcoal or the like in a solvent such as ethanol, methanol, ethyl acetate, or THF at temperatures ranging from 0° C. to 80° C. preferably room temperature various ratios. In the case of $Rp_5$=methoxy the compound is treated with LiOH in a mixture of water and methanol, preferably 3:1 at temperatures ranging from 0° C. to 20° C. preferably 5° C. during 5 to 30 hours preferably 15 hours. In the case of $Rp_5$=t-butyloxy the compound is treated with trifluoroacetic acid in methylene chloride at temperatures ranging from 10 to 40° C. preferably 25 during 30 minutes to 5 hours preferably 2 hours or 1% to 5% HCl in an alcoholic solvent such as methanol or ethanol at room temperature during 1 to 24 hours, preferably 12 hours, to yield compounds of formula XIX as a mixture of diastereoisomers in various ratios (cf. T. W. Green et al., Protective Groups in Organic Synthesis, John Wiley & Sons, 1999.)

Compounds of formula XIX are then coupled with an appropriate compound Q—X—H wherein X has a terminal nitrogen atom using a coupling reagent such as 1,3-dicyclohexylcarbodiimide (DCC), 1-(3-dimethylaminopropyl)-3-ethylcarboduimide (EDC), bis(2-oxo-3-oxazolidinyl)phosphinic chloride (BOP-CI), O-(benzotriazol-1-yl)-N,N,N',N'-bis(tetramethylene)uronium tetrafluoroborate, O-(benzotriazol-1-yl)-N,N,N',N'-tetramethyluronium hexafluorophosphate, benzotriazol-1-yloxytripyrrolidinophosphonium hexafluorophosphate or isobutyl chloroformate in the presence of an organic base such as triethylamine or diisopropyl ethylamine and optionally 4-(dimethylamino) pyridine (DMAP) and/or 1-Hydroxybenzotriazole (HOBT) in a solvent such as methylene chloride, acetonitrile, DMF or THF at temperatures ranging from 0° C. to room temperature during 1 to 24 hours to obtain compounds of formula XX as a mixture of diastereoisomers in various ratios (reaction $T^1$). Compounds of formula XX where $R=CH_3$ can then be deprotected at the 2' position following the procedure described above (reaction $M^5$) to obtain compounds of formula Ic as single diastereoisomers. In the case of $R^7$=allyl or propargyl compounds XX can be submitted to a "Heck" or "Sonogashira" reaction respectively as described above (reaction $R^3$) yielding compounds of formula XXI. These compounds are then deprotected as described above (reaction $M^6$) to obtain compounds of formula Ic as single diastereoisomers.

Scheme 5

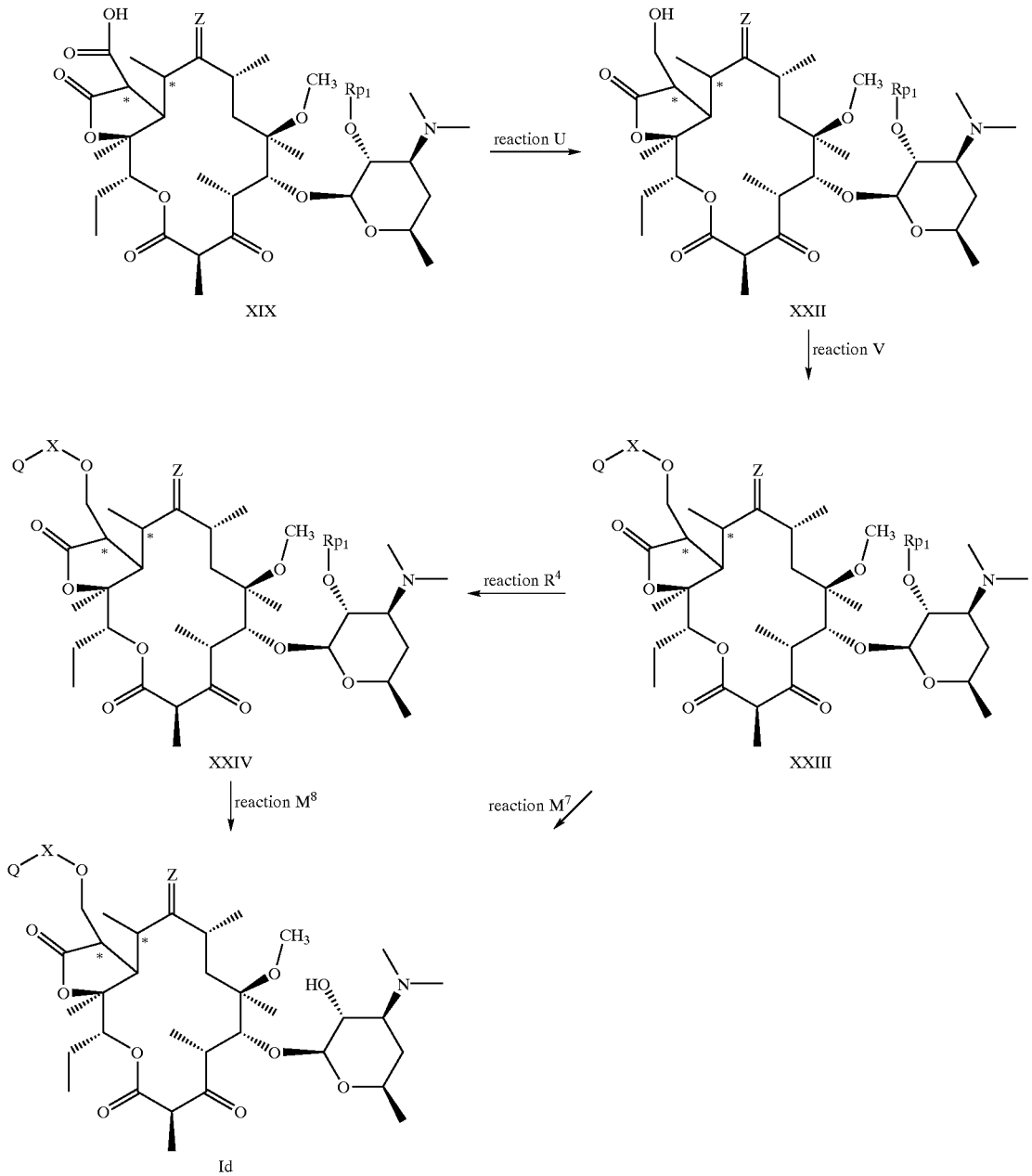

The carboxylic acid group of compounds of formula XIX wherein $R^7$=$CH_3$, Z=O and $Rp_1$ is as defined above is reduced with a reducing agent such as $BH_3$ in a solvent such as THF at temperatures ranging from −78° C. to 25° C. during 1 hour to 24 hours preferably 3 hours (scheme 5, reaction U) to give compounds of formula XXII as a mixture of diastereoisomer in various ratios. The hydroxy group of compounds of formula XXII is then alkylated (reaction V) analogously to the reaction described in WO 0078773 with allyl t-butyl carbonate (preparation described in WO 0078773) in the presence of for example tris(dibenzylideneacetone)dipalladium and 1,4-bis(diphenylphosphine)butane at temperatures ranging from 50° C. to the boiling point of the solvent in an aprotic solvent such as THF during 2 hours to give compounds of formula XXIII wherein X is allyl and Q is H as a mixture of diastereoisomers in various ratios. Alternatively, the hydroxy group is reacted analogous to the conditions described in Clark et al., *Bioorg. Med. Chem. Lett.* 2000, 10, 815–819 with propargylbromide in the presence of a base such as potassium t-butoxide potassium hydroxide or sodium hydride in a mixture of DMSO and THF at 0° C. during 1 hour to give compounds of formula XXIII wherein X is propargyl and Q is H as a mixture of diastereoisomers in various ratios. Compounds of formula XXIII wherein Z, $Rp_1$, X and Q are as defined in this paragraph, are then submitted to a "Heck" reaction in the case of X=allyl or a "Sonogashira" reaction in the case of X=propargyl as described above (reaction $R^4$) to give compounds of formula XXIV. These compounds are then deprotected at the 2' position as described above (reaction $M^8$) to obtain compounds of formula Id as single diastereoisomers.

Compounds of formula XXII can also be reacted with isocyanates in a solvent such as methylene chloride, DMF, acetonitrile or toluene, preferably in the presence of a base such as triethylamine, DBU or pyridine at temperatures ranging from 20° C. to the boiling point of the solvent during 5 to 24 hours to give compounds of formula XXIII which are then deprotected to give compounds of formula Id as a single diastereoisomer (reaction $M^7$).

Scheme 6

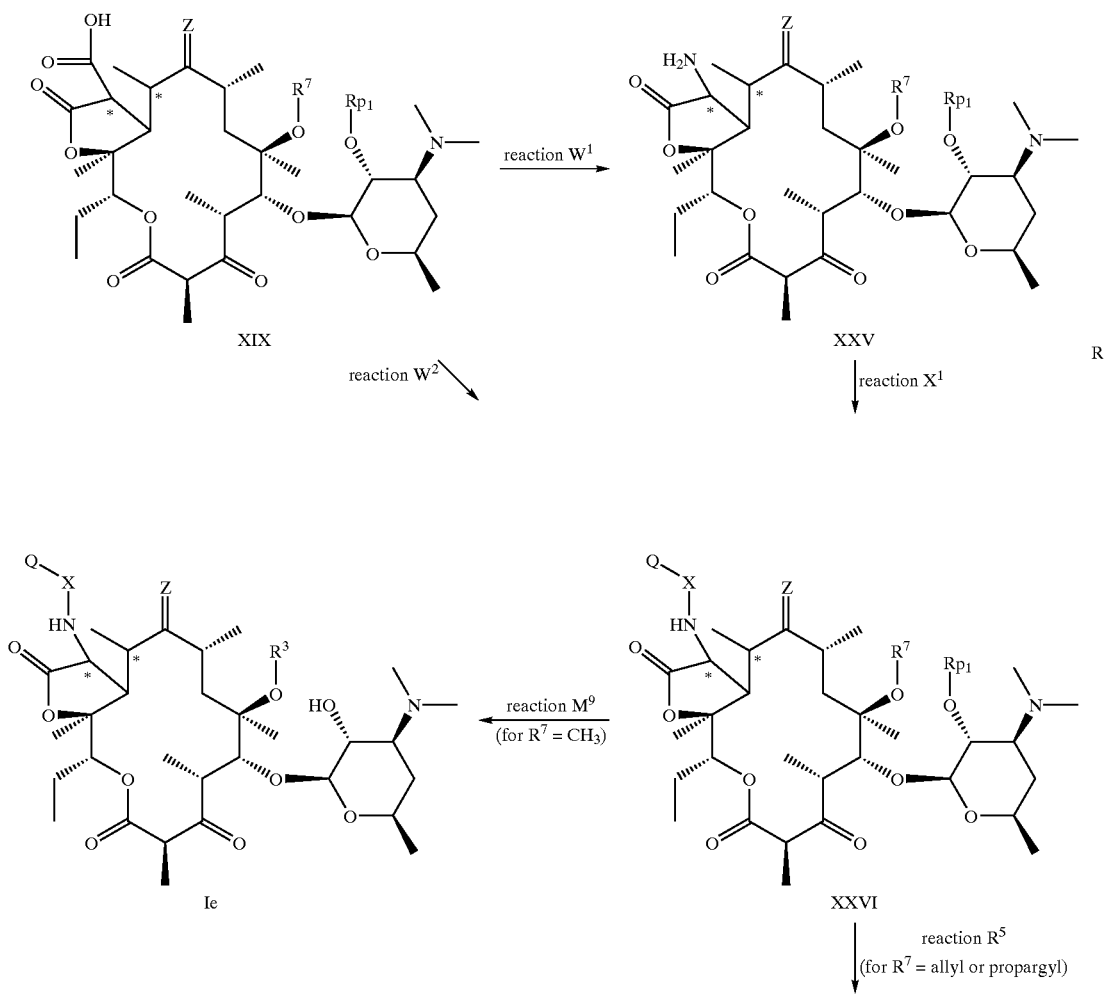

-continued

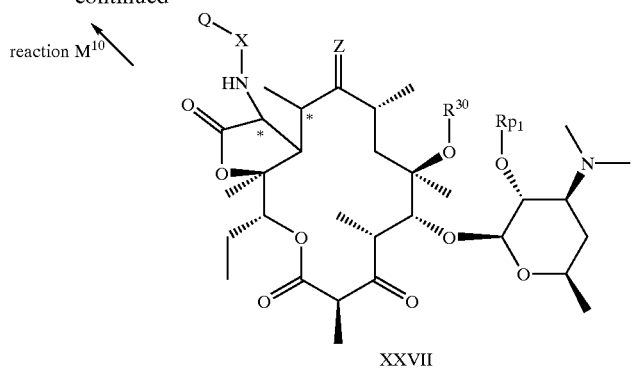

XXVII

R[30] is as in XIII

Compounds of formula XIX wherein Z=O, R[7] is methyl, allyl or propargyl and Rp₁ is as defined above can be further modified as summarised in scheme 6. In the first step compounds XIX are subjected to the so called Curtius rearrangement (reaction W[1]) by reacting with diphenylphosphoryl azide and triethylamine in a solvent such as benzene toluene or acetonitrile at temperatures ranging from 25° C. to the boiling point of the solvent. After 1 hour benzylalcohol, p-methoxybenzylalcohol, t-butylalcohol, 2-trimethylsilylethanol or water is added and the mixture is heated to temperatures ranging from 50 to 110° C. during 5 to 24 hours. Alternatively the same starting material is treated with ethyl chloroformate and triethylamine in a mixture of acetone and water at temperatures ranging from −5 to 10° C. preferably 0° C. during 1 to 2 hours. Now sodium azide is added and the mixture is stirred for another 1 to 5 hours at the same temperature. If one of the above mentioned alcohols has been added to the reaction mixture, the free amine is liberated from the intermediate carbamate, depending on the nature of the alcohol, with H₂/Pd/C (in case of benzylalcohol or p-methoxybenzylalcohol), HCl or trifluoroacetic acid (in case of t-butylalcohol) or tetrabutylammonium fluoride (in case of 2-trimethylsilylethanol) according to standard procedures described in T. W. Green et al., Protective Groups in Organic Synthesis, John Wiley & Sons, 1999 to give compounds of formula XXV as a mixture of diastereoisomers in various ratios. If the intermediate isocyanate, which is formed during the Curtius rearrangement, is reacted with compounds Q—XH, which have a terminal NH or OH group, compounds of formula XXVI can be formed in one step from compounds XIX (reaction W[2]).

Compounds XXV are coupled to appropriate carboxylic acids (reaction X[t]) under conditions described for reaction T[1], scheme 4 or alternatively to appropriate acid chlorides, chloroformate esters or sulfonyl chlorids in the presence of an amine base such as triethylamine, diisopropylethylamine or the like in a solvent such as methylene chloride or THF at temperature ranging from −78° C. to room temperature during 1 hour to 24 hours to give compounds of formula XXVI as a mixture of diastereoisomers in various ratios.

Compounds of formula XXVI where R[7]=CH₃ can then be deprotected at the 2' position following the procedure described above (reaction M[9]) to obtain compounds of formula I as single diastereoisomers or in the case of R[7]=allyl or propargyl compounds XXVI can be submitted to a Heck or a Sonogashira reaction respectively as described above (reaction R[5]) yielding compounds of formula XXVII. These compounds are then deprotected as described above (reaction M[10]) to obtain compounds of formula Ie as single diastereoisomers.

Scheme 7

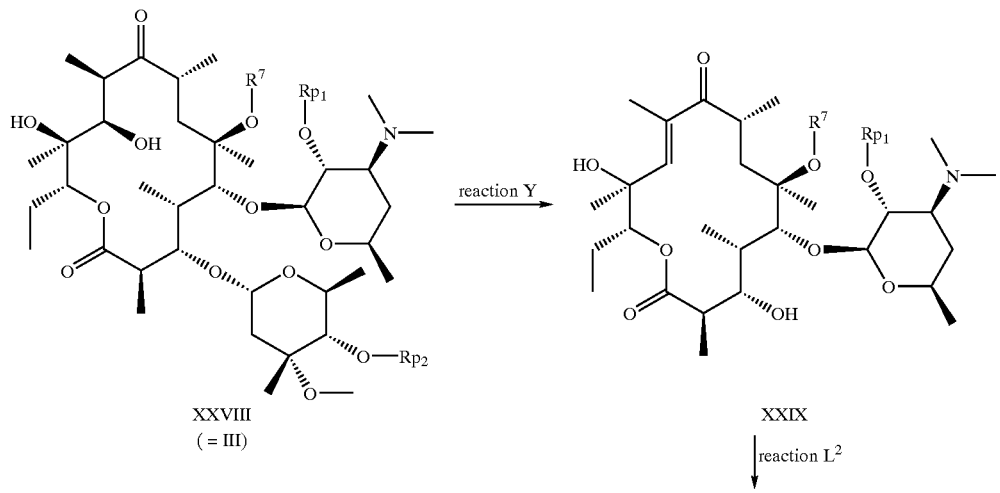

XXVIII
(=III)

reaction Y

XXIX reaction L[2]

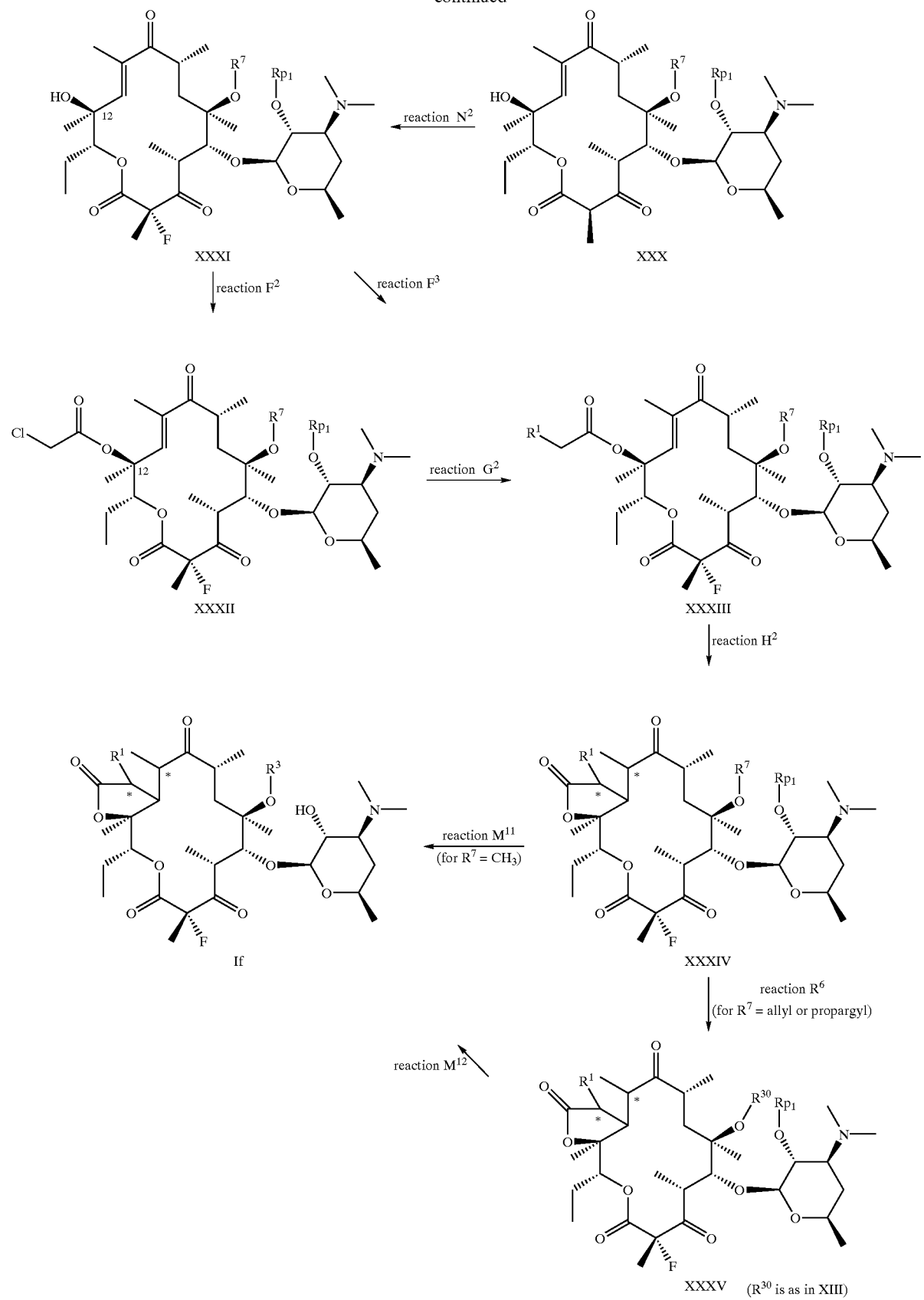

Compounds of formula XXVIII (=III) wherein $R^7$ is as defined above and $Rp_1$ and $Rp_2$ are as defined above or H are transformed into compounds of formula XXIX wherein $Rp_1$ is as defined above, but not H, following a procedure described in Elliott et al., *J. Med. Chem.*, 1998, 41, 1651–1659 (reaction Y). The hydroxy group in position 3 of compounds XXIX is then oxidized according to the procedure described for scheme 2 (reaction $L^2$) and the product obtained then subsequently fluorinated at position 2 following the procedure described for scheme 3 above (reaction $N^2$) to yield compounds of formula XXXI. The hydroxy group at position 12 of compounds of formula XXXI is then esterified to give compounds of formula XXXIII either in a two step procedure or directly as specified in scheme 2 above (reactions $F^2$ and $G^2$ or reaction $F^3$). Compounds of formula XXXIII are then cyclised under similar conditions as described in scheme 2 above (reaction $H^2$) to give compounds of formula XXXIV as a mixture of diastereoisomers in various ratios.

Compounds of formula XXXIV can then (for $R^7$=$CH_3$) be deprotected at the 2' position following the procedure described above (reaction $M^{11}$) to obtain compounds of formula If as single diastereoisomers, or in the case of $R^7$=allyl or propargyl compounds XXXIV can be submitted to a "Heck" or a "Sonogashira" reaction, respectively, as described above (reaction $R^6$) yielding compounds of formula XXXV. These compounds are then deprotected as described above (reaction $M^{12}$) to obtain compounds of formula If as single diastereoisomers.

Scheme 8

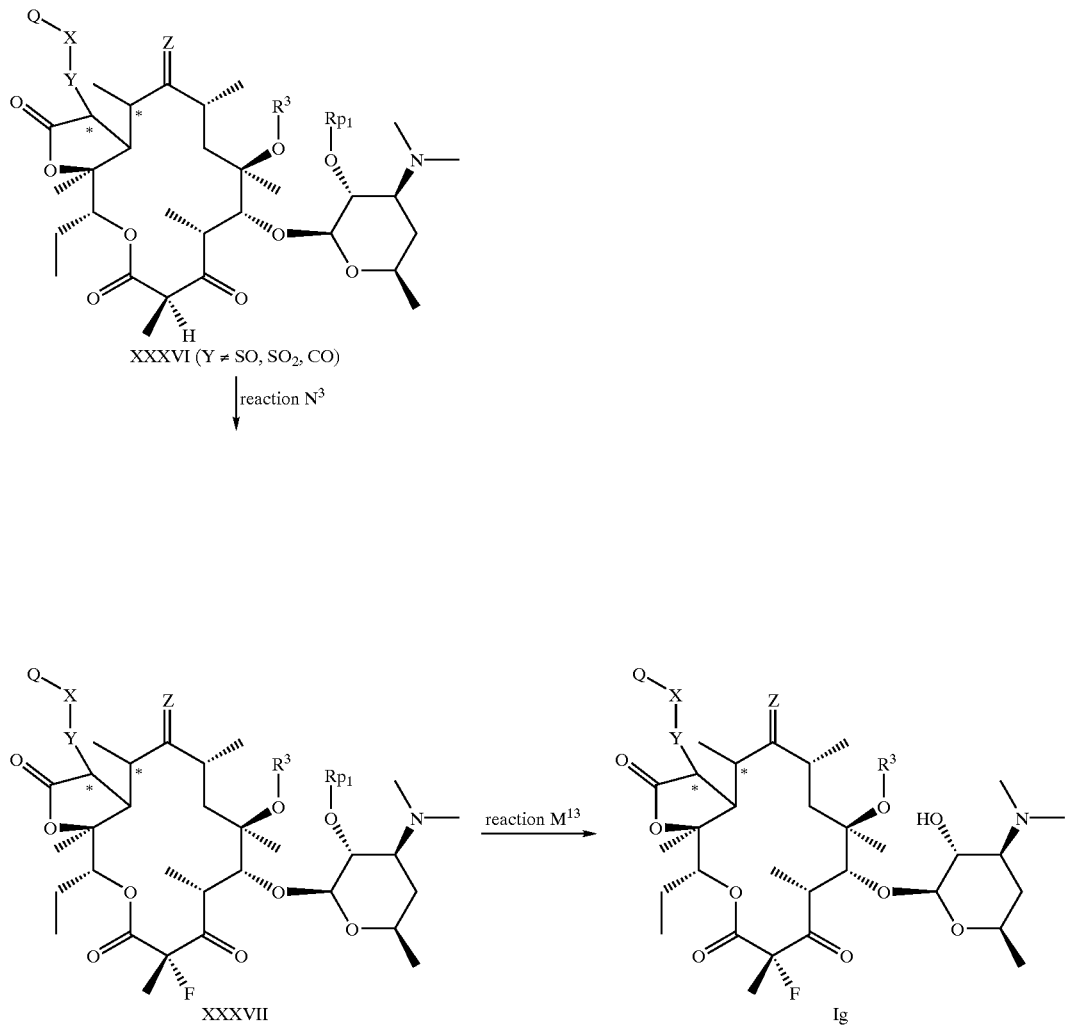

As summarised in scheme 8, compounds of formula X)CXVI wherein $R^3$, $Rp_1$, Q and X are as defined above and Y is as defined (excluding SO, $SO_2$ and CO) are fluorinated in the 12 position following the procedure described above (reaction $N^3$) to give compounds of formula XXXVII as a mixture of diastereoisomers in various ratios. These compounds are then deprotected as described above (reaction $M^{13}$) to obtain compounds of formula Ig as single diastereoisomers.

perature preferably 0° C. during 1 hour to 3 hours (reaction $Z^1$). The N-oxide which is formed on the dimethylamino group of the sugar residue during the reaction is reduced at work-up by treating the organic phase with a aqueous solution of sodium pyrosulfite at room temperature during 5 minutes to 24 hours to give compounds of formula XXXVIII as a mixture of diastereoisomers. Alternatively, if appropriate, the N-oxide is reduced by catalytic hydrogenation according to standard procedures. Compounds of formula

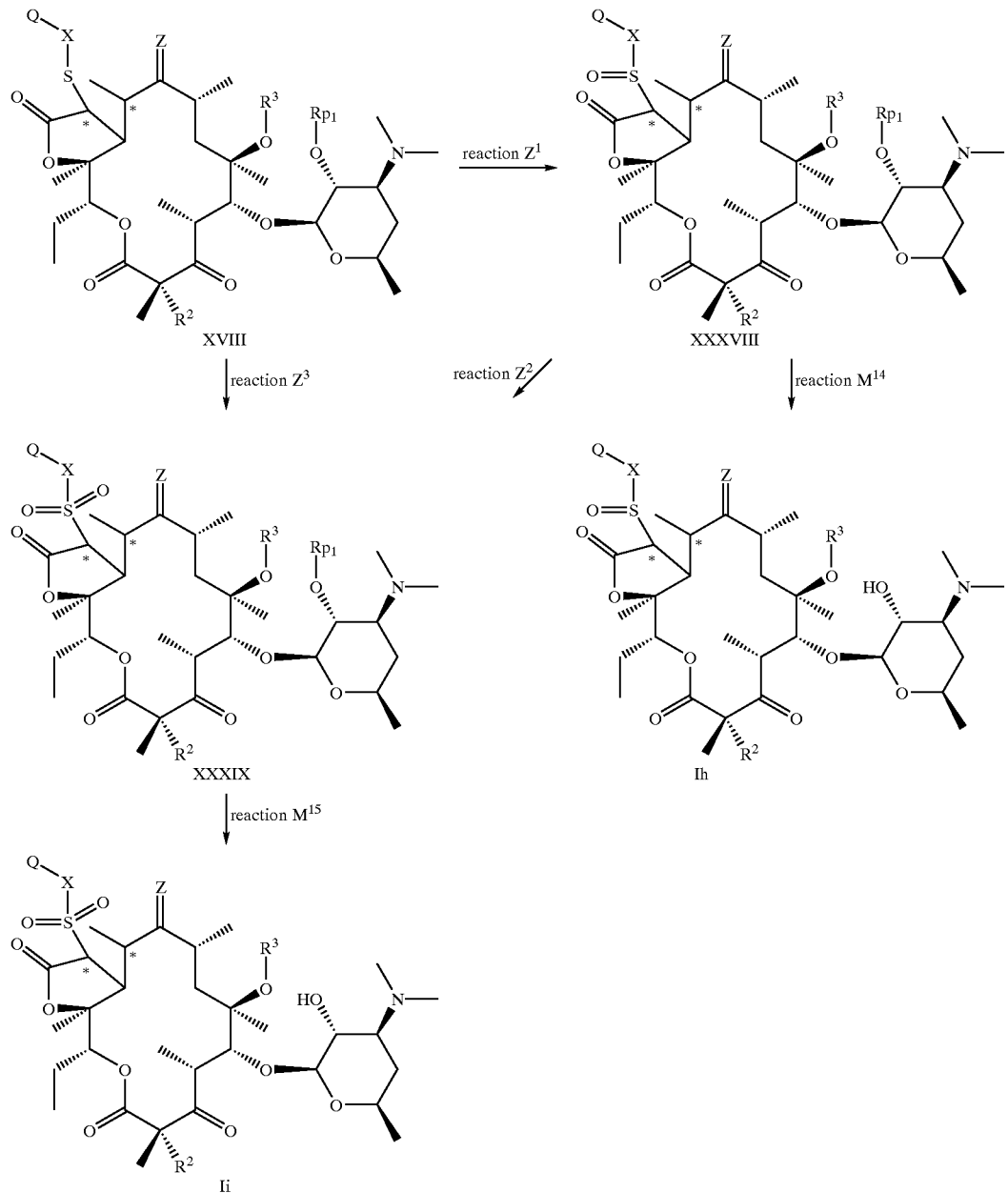

Scheme 9

Compounds of formula XVIII are treated with 2 to 2.5 equivalent of 3-chloroperoxybenzoic acid (MCPBA) and 4 to 5 equivalent of $NaHCO_3$ in a solvent such as methylene chloride at temperatures ranging from 0° C. to room tem- XXXVIII can then be deprotected at the 2' position following the procedure described above (reaction $M^3$) to obtain compounds of formula Ih as a mixture of diastereoisomers in various ratios or are further oxidised as described above but at room temperature during 1 to 48 hours to give, after reduction of the N-oxide, compounds of formula XXXIX as a mixture of diastereoisomers in various ratios (reaction $Z^2$) Compounds XXXIX can also be obtained in one step (reaction $Z^3$) by using 3,5 to 10 equivalent of the oxidising agent and 7 to 20 equivalent of $NaHCO_3$ at temperatures oxidation. Suitable protecting groups commonly known in the art can be introduced according to standard procedures described in T. W. Green et al., Protective Groups in Organic Synthesis, John Wiley & Sons, 1999. After oxidation (reaction $Z^1$, $Z^2$ or $Z^3$), the protecting group can be removed following standard procedures also described in T. W. Green et al.

Scheme 10

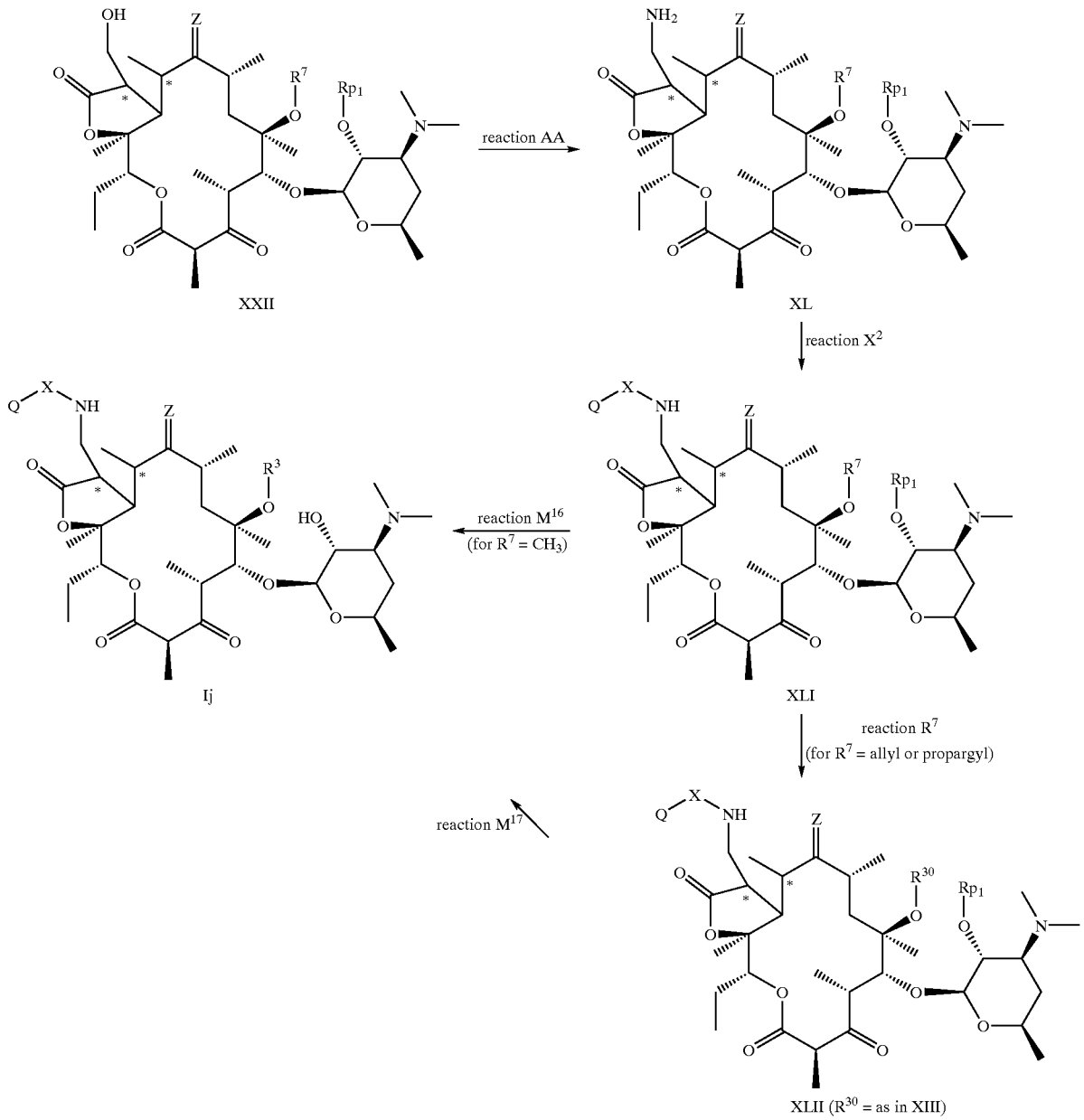

ranging from 0° C. to room temperatures during 5 to 48 hours followed by the workup procedure described above. Compounds of formula XXXIX are then deprotected at the 2' position following the procedure described above (reaction $M^{15}$) to obtain compounds of formula Ii as single diastereoisomers.

In the case where Q is further substituted with oxidation sensitive substituents like amino groups, these substituents need to be protected before submitting the sulfide XVIII to Compounds of formula XXII, triphenylphosphine and $HN_3$ are dissolved in a solvent such as benzene or THF and treated with diethyl azodicarboxylate at temperatures ranging from −78° C. to room temperature during 1 to 24 hours. Another equivalent of tiphenylphosphine is added followed after 3 to 24 hours by water or dilute hydrochloric acid at temperatures ranging from 20° C. to 50° C. (reaction AA) to give compounds of formula XL as a mixture of diastereoisomers in various ratios. Compounds of formula XL are then further modified (reaction $X^2$) according to the procedure described in scheme 6 for reaction $X^1$ to give compounds of formula XLI as a mixture of diasteroisomers in various ratios. Compounds of formula XLI can then be deprotected at the 2' position following the procedure described above (reaction $M^{16}$) to obtain compounds of formula Ij as single diastereoisomers, or in the case of $R^7$=allyl or propargyl compounds XLI can be submitted to a "Heck" or a "Sonogashira" reaction, respectively, as described above (reaction $R^7$) yielding compounds of formula XLII. These compounds are then deprotected as described above (reaction $M^{17}$) to obtain compounds of formula Ij as single diastereoisomers.

Scheme 11

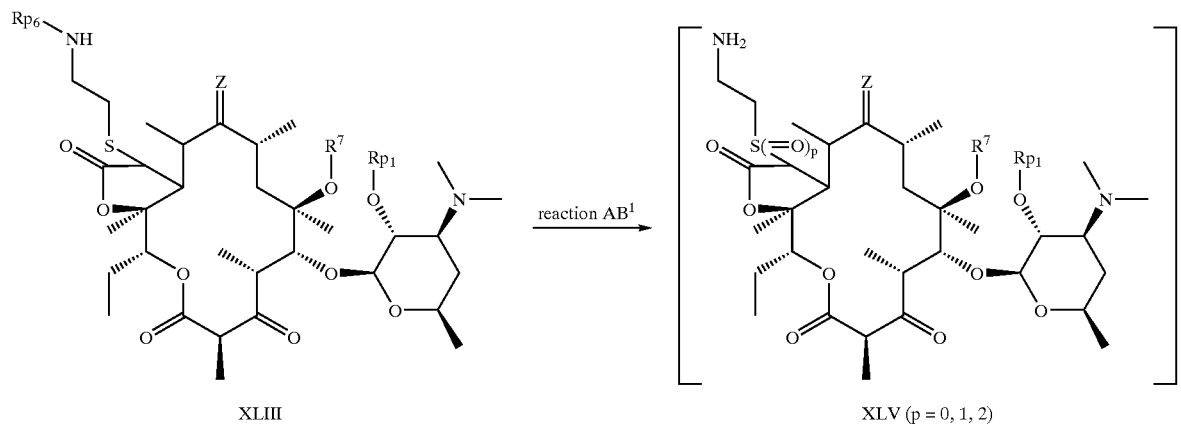

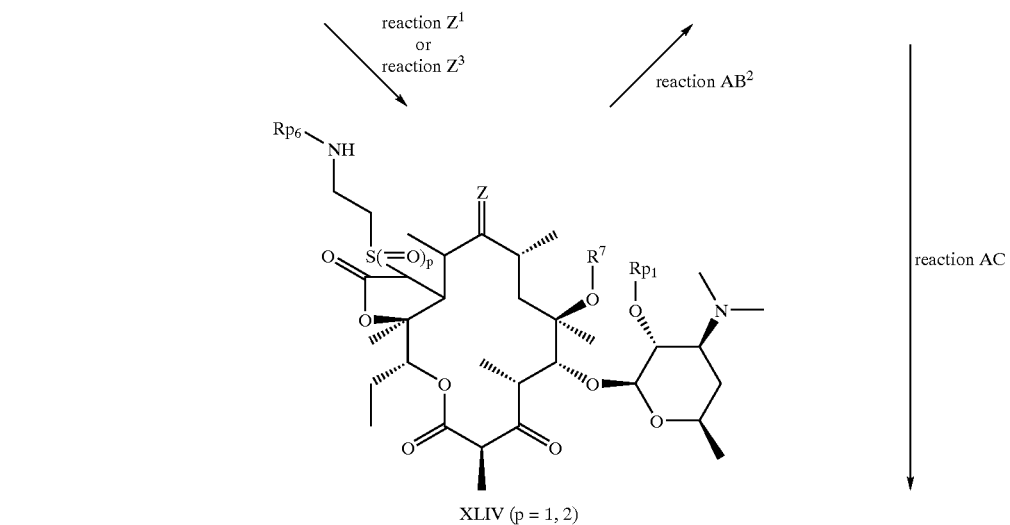

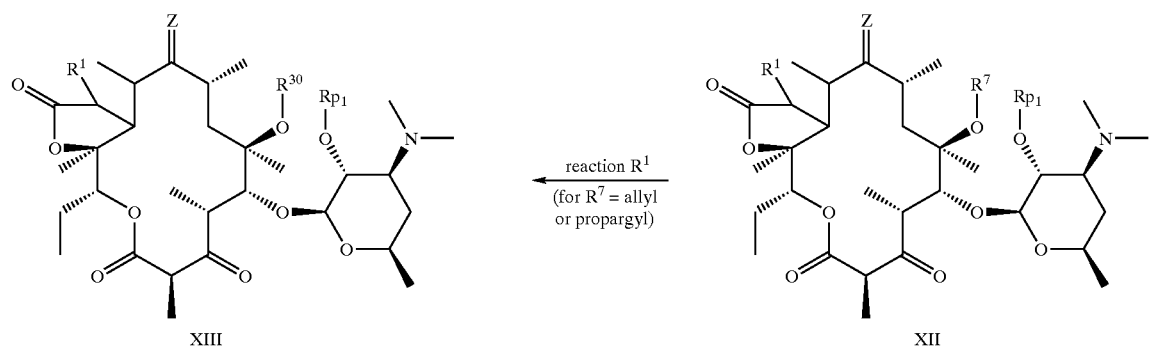

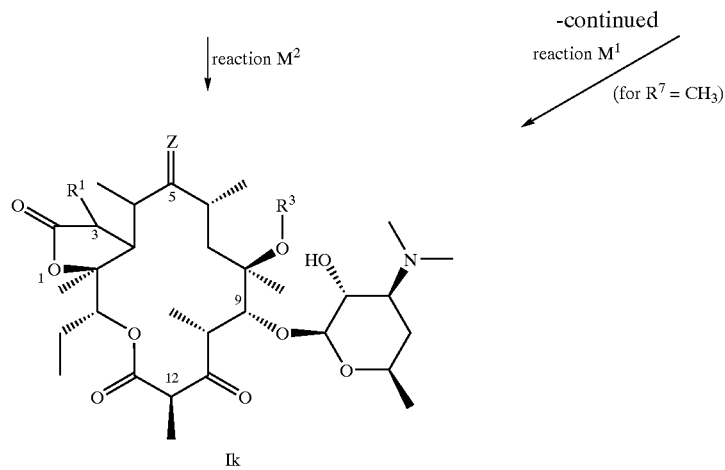

Compounds of formula XLIII wherein $R^7$ and $Rp_1$ are as described above and $Rp_6$ is an amino protecting group like t-butoxy carbonyl (t-BOC), benzyloxycarbonyl (Z) or allyloxycarbonyl (Alloc), preferentially t-butoxy carbonyl, are obtained following the procedure described in scheme 2 using N-protected 2-aminoethane thiol in reaction G. Compounds of formula XLIII are transformed into compounds of formula XLV by cleavage of the amino protecting group $Rp_6$. The amino protecting groups may be cleaved off by acid hydrolysis (e.g. the t-butoxycarbonyl group), preferably with the aid of a lower alkanecarboxylic acid which may be halogenated. In particular formic acid or trifluoroacetic acid is used. The reaction is carried out in the acid or in the presence of a co-solvent such as a halogenated lower alkane, e.g. methylene chloride preferably at room temperature although it can be carried out at a slightly lower or a slightly higher temperature (e.g. a temperature in the range of about −30° C. to +40° C.). The benzyloxycarbonyl group can be cleaved off by hydrogenation at atmospheric pressure in the presence of a catalyst, e.g. Palladium on charcoal in a solvent like ethanol, methanol or ethyl acetate. The allyloxycarbonyl group is cleaved in a palladium (O) catalysed transallylation in the presence of an allyl group scavenger such as, e.g. trimethylsilanyldimethylamine, as described in Tetrahedron Letters, 33, 477,–480 (1992). Alternatively, compounds of formula XLIII can first be oxidised into compounds of formula XLIV as described for scheme 9. Compounds of formula XLIV are subsequently transformed into compounds of formula XLV following procedures described above. Crude compounds of formula XLV are coupled to appropriate carboxylic acids (reaction AC) under conditions described for reaction $T^1$, scheme 4 or alternatively to appropriate acid chlorides, chloroformate esters or sulfonyl chlorides as described for reaction X1, scheme 6 to give compounds of formula XII. Alternatively compounds of formula XII can be obtained by conducting a nucleophilic aromatic substitution of halogenated aromatic or heteroaromatic derivatives with compounds of formula XLV in a protic solvent like ethanol or methanol at temperatures between 20° C. and refluxing temperature, during 1 to 48 hours in the presence of an organic base such as triethylamine. The substitution can also be conducted in a polar aprotic solvent like N,N-dimethylformamide, N,N-dimethyl acetamide N-methyl pyrrolidone or acetonitrile at temperature ranging from 20° C. to 150° C. during 1 to 24 hours. The cross coupling can also be catalysed by Pd (O) complexes following the procedures described for example in J. Org. Chem. 1996, 61, 7240–7241.

Compounds XII are then deprotected as described above (reaction $M^1$) to obtain compounds of formula Ik as single diastereoisomers. Compounds XII can be further transformed by submitting them to a Heck or Shonogashira reaction as described above (reaction $R^1$ scheme 2). Final products of formula Ik are then deprotected as described above (reaction $M^1$).

"Heck" and "Sonogashira" products XVIII, XXI, XXIII, XXVII, XXXV and XLII can be saturated in analogy to compounds XIII as described above.

The following Examples illustrate the invention without being construed as limiting.

EXAMPLE 1

Preparation of (3R or S, 3aR, 4R or S, 6R, 8R, 9R, 10R, 12S, 15R, 15aS)-15-Ethyl-12-fluorooctahydro-8-methoxy-3-[[(4-methoxyphenyl) methyl]thio]-4,6,8,10,12,15a-hexamethyl-9-[[3,4,6-trideoxy-3-(dimethylamino)-β-D-xylo-hexopyranosyl]oxy]-2H-furo [2,3-c] oxacyclotetradecin-2,5,11, 13 (3H,6H,12H)-tetrone (I-1), compound of formula I, wherein $R^1$ is [(4-methoxyphenyl) methyl]thio, $R^2$ is fluoro, $R^3$ is methyl and Z is oxygen. A] (10E)-10,11-Didehydro-11-deoxy-6-O-methyl-erythromycin 2'-acetate 12-(chloroacetate) 4"-(phenylmethyl carbonate) (VII-1) (Scheme 2, formula VII):

To a solution of 14 g (15.4 mmol) (10E)-10,11-didehydro-11-deoxy6O -methyl-erythromycin-2'-acetate-4"-(phenylmethyl carbonate) (VI) and 566 mg DMAP in 280 ml dichloromethane, were added simultaneously a solution of 4.38 g (46.35 mmol) of chloroacetic acid in 70 ml dichloromethane and a solution of 9.56g (46.35 mmol) DCC in 70 ml $CH_2Cl_2$ dropwise over 2 hours under argon. Following addition, the solution was stirred a room temperature for further 2 hours. The volume of the reaction mixture was reduced under reduced pressure to 100 ml and the insoluble precipitate was eliminated by filtration. The filtrate was washed twice with 50 ml of a 5% aqueous $NaHCO_3$ solution. The organic layer was washed successively with 50 ml water, 50ml brine, dried over $Na_2SO_4$ and evaporated. The resulting oil was purified by flash chromatography (1% $NH_3OH$ in dichloromethane/MeOH 90:10). Fractions containing pure product were combined, evaporated and dried under reduced pressure to give 15 g (98%) product as a colorless foam. MS (ISP): 982.4 (MH$^+$).$^1$H-NMR (CDCl$_3$) diagnostic signals only: 0.90 (t, 3H), 0.93 (d, 3H), 1.12 (d, 3H), 1.18 (d, 3H), 1.24 (s, 3H), 1.28 (d, 3H), 1.35 (d, 3H), 1.70 (s, 3H), 2.00 (s, 3H), 2.23 (s, 6H), 2.40 (d, 1H), 2.67 (m, 1H), 2.87 (m, 1H), 3.12 (s, 3H), 3.24 (m, 1H), 3.32 (s, 3H), 3.56 (m, 2 H), 3.81 (m, 1H), 3.98 (s, 2H), 3.86 (m, 1H), 3.95 (d, 1H), 4.07 (d, 1H), 4.29 (m, 1H), 4.96 (m, 1H), 5.21 (dd, 2H), 5.71 (dd, 1H), 6.60 (s, 1H), 7.35 (s, 5H).

B] (10E)-10,11-Didehydro-11-deoxy-6-O-methyl-erythromycin 2'-acetate 4"-(phenylmethyl carbonate) 12-[[[(4-methoxyphenyl)methyl]thio]acetate] (VIII-1):

To a solution of 10 g (10.1 mmol) VII-1 dissolved in 400 ml acetone were added 1.74 g (11.4 mmol) DBU and a catalytic amount of sodium iodide. (4-Methoxyphenyl)-methanethiol (1.66g, 10.78 mmol) was added in one portion and the resulting suspension was stirred at room temperature for 1.5h. The reaction mixture was diluted with 1 l CH$_2$Cl$_2$, extracted twice with 400 ml 5% aqueous NaHCO$_3$, dried over Na$_2$SO$_4$ and evaporated to give 10.55 g of a foamy beige compound. The crude product was used without purification for the next step. MS (ISP): 1100.6 (MHN).

C] (3R or S, 3aR, 4R or S, 6R, 8R, 9R, 10S, 11S, 12R, 15R, 15aS)-9-[[2-O-Acetyl-3,4,6-tri-deoxy-3-(dimethylamino)-β-D-xylo-hexopyranosyl]oxy]-11-[[2,6-dideoxy-3-C-methyl-3-O-methyl-4-O-[(phenylmethoxy)carbonyl]-α-L-ribo-hexopyranosyl]oxy]-15-ethyl-decahydro-8-methoxy-3-[[(4-methoxyphenyl)methyl]thio]-4,6,8,10,12,15a-hexamethyl-2H-furo [2,3-c] oxacyclotetradecin-2,5,13 (3H, 6H)-trione; mixture of diastereomers (IX-1):

To an ice cold solution of 3 g (2.72 mmol) of ester VIII-1 in 30 ml dry DMF kept under argon was added at once 164 mg of a 60% sodium hydride oil dispersion. The resulting mixture was stirred at 0° C. for 3 hours and then partitioned between 50 ml diethylether and 50 ml of 0.5 M KH$_2$PO$_4$ solution. The organic layer was washed twice with 50 ml of 3% NaHCO$_3$ solution and 50 ml brine, dried over Na$_2$SO$_4$ and evaporated to yield 2.97 g of crude product as a yellow foam. MS (ISP): 1100.6 (MH$^+$)

D] (3R or S, 3aR, 4R or S, 6R, 8R, 9R, 10S, 11S, 12R, 15R, 15aS)-9-[[2-O-Acetyl-3,4,6-trideoxy-3-(dimethylamino)-β-D-xylo-hexopyranosyl]oxy]-15-ethyldecahydro-11-hydroxy-8-methoxy-3-[[(4-methoxyphenyl)methyl]thio]-4,6,8,10,12,15a-hexamethyl-2H-furo [2,3-c] oxacyclotetradecin-2,5,13 (3H,6H)-trione; mixture of diastereomers (XI-1):

2.96 g (2.69 mmol) IX-1 were dissolved in 150 ml methanol containing 3% HCl. The solution was kept at room temperature for 24 hours and evaporated. The crude hydrochloride salt was redissolved in 100 ml dichloromethane, washed twice with 50 ml 5% NaHCO$_3$ and 50 ml brine, dried over Na$_2$SO$_4$ and evaporated to give 2.8 g of crude product which was purified by chromatography on silica gel eluting with dichloromethane/methanol 9:1 to give 1.52 g of a colorless foam. MS (ISP): 808.5 (MH$^+$).

E] (3R or S, 3aR, 4R or S, 6R, 8R, 9R, 10R, 12R, 15R, 15aS)-9-[[2-O-Acetyl-3,4,6-trideoxy-3-(dimethylamino)-β-D-xylo-hexopyranosyl]oxy]-15-ethyloctahydro-8-methoxy-3-[[(4-methoxyphenyl)methyl]thiol -4,6,8,10,12,15a-hexamethyl-2H-furo [2,3-c] oxacyclo-tetradecin-2,5,11,13 (3H, 6H, 12H)-tetrone; mixture of diastereomers (XII-1):

19.6 g of a 15% wt solution of Dess-Martin reagent in dichloromethane was added dropwise over a period of 10 minutes to a solution of 1.5 g (2.69 mmol) XI-1 in 130 ml dichloromethane at 0° C. under argon. The reaction mixture was stirred at 0° C. for 1 h30 and at room temperature for 1 h. The resulting yellow solution was diluted with 25 ml diethyl ether and then poured into a mixture of 148 g of a 10% aqueous solution of Na$_2$S$_2$O$_3$ and 13.5 g of a saturated NaHCO$_3$ solution and stirred for 1 h. The organic layer was separated, the aqueous phase was extracted twice with 100 ml of diethylether. The combined organic phases were washed with 100 ml of 3% NaHCO$_3$, 100 ml water, 100 ml brine, dried over Na$_2$SO$_4$ and evaporated. Flash chromatography on silica gel with dichloromethane/methanol/ammonia 90:10:1 gave 1.34 g (61%) of the protected ketolide XII-1 as a beige foam as a mixture of diastereomers. MS (ISP): 806.6 (MH$^+$).

F] (3R or S, 3aR, 4R or S, 6R, 8R, 9R, 10R, 12S, 15R, 15aS)-9-[[2-O-Acetyl-3,4,6-trideoxy-3-(dimethylamino) -β-D-xylo-hexopyranosyl]oxy]-15-ethyl-12-fluoroctahydro-8-methoxy-3-[[(4-methoxyphenyl)methyl]thio]-4,6,8,10,12,15a-hexamethyl-2H-furo [2,3-c] oxacyclo-tetradecin-2,5,11,13 (3H,6H,12H)-tetrone; (XIV-1)

To a solution of 200 mg (0.248mmol) of ketolide XII-1 in 3 ml DMF at 0° C. under argon was added sodium hydride (60% in oil, 21.8 mg, 0.546 mmol) and the mixture was stirred at 0° C. for 1 h. To this orange solution cooled to −20° C. was added N-fluoro-benzenesulfonimide (86.1 mg, 0.27mmol) and the mixture was stirred at 0° C. for 5 min. The reaction mixture was then treated dropwise with a solution of 30 mg acetic acid in 0.7 ml DMF over a period of 10 min., diluted with 50 ml Ethyl acetate and washed twice with 25 ml of a 3% aqueous NaHCO$_3$ solution and with 35 ml brine, dried over Na$_2$SO$_4$ and evaporated. The crude product was purified by chromatography on silica gel with dichloromethane/methanol/ammonia 95:5:1 to give 40 mg (20%) of the desired compound XIV-1 as a slightly yellow foam. MS (ISP): 824.2 (MH$^+$) $^{and}$ 145 mg (70%) of the N-oxide derivative of XIV-1 MS (ISP): 840.2 (M$^+$).

G] (3R or S, 3aR, 4R or S, 6R, 8R, 9R, 10R, 12S, 15R, 15aS)-15-Ethyloctahydro-12-fluoro-8-methoxy-3-[[(4-methoxyphenyl) methyl]thio]-4,6,8,10,12,15a-hexamethyl-9-[[3,4,6-trideoxy-3-(dimethylamino)-β-D-xylo-hexopyranosyl]oxy]-2H-furo [2,3-c] oxacyclotetradecin-2,5,11,13 (3H,6H, 12H)-tetrone (I-1):

230 mg of protected ketolide XIV-1 were dissolved in 5 ml methanol and stirred for 72 hours at room temperature. The solvent was removed under reduced pressure. The residue was dissolved in 10 ml dichloromethane and the resulting solution stirred with 10 ml of a 10% aqueous solution of sodium pyrosulfite during 1 h. The pH of the solution was set on pH 8 with a saturated solution of NaHCO$_3$ and the organic phase separated. The aqueous phase was extracted twice with 10 ml dichloromethane and the combined organic phases were dried over Na$_2$SO$_4$ and evaporated. The crude product was purified by chromatography on silica gel eluting with dichloromethane/methanol/ammonia 90:10:1 to give 111 mg (51%) of the desired compound I-1 as a single diastereomer. MS (ISP): 782.3 (MH$^+$). $^1$H-NMR (CDCl$_3$) diagnostic signals only: 0.91 (t, 3H), 1.04 (d, 3H), 1.13 (d, 3H), 1.27 (d, 3H), 1.29 (d, 3H), 1.31 (s, 3H), 1.51 (s, 3H), 1,6–1,7 (m,2H), 1.78 (d, 3H), 2.26 (s broad, 6H), 2.64 (s, 3H), 2.98 (q, 1H), 3.31 (m, 1H), 3.56 (m, 2H), 3.80 (s, 3H), 4.06 (dd, 2H), 4.37 (d, 1H), 5.42 (dd, 1H), 6.83 (d, 2H), 7.32 (d, 2H).

EXAMPLE 2

Preparation of I-2, compound of formula I, where $R^1$ is [(4-methoxyphenyl)methyl]-sulfonyl, $R^2$ is fluoro, $R^3$ is methyl and Z is oxygen.

A] To a stirred solution of 65 mg (79 μmol) sulfide XVIII-1 in 3 ml dichloromethane at 0° C. were added 46 mg (550 μmol) of sodium bicarbonate and 68 mg (276 μmol) of m-chloroperbenzoic acid. The mixture was allowed to warm to room temperature and stirred for 2 h. 5 ml of an aqueous sodium pyrosulfite solution were added and the two-phase system was stirred for 1 h. The pH of the solution was adjusted to pH 9 with saturated sodium carbonate solution and extracted twice with 10 ml dichloromethane. The combined organic phases were washed with 10 ml 3% $NaHCO_3$ aqueous solution, 10 ml of brine, dried over $Na_2SO_4$ and evaporated to give 55 mg (81%) of compound XXXIX-2 as a light yellow solid. MS (ISP): 856.3 ($MH^+$).

Deprotection of XXXIX-2 was performed as described in example 1G to give product I-2 as a colorless solid as a single diastereomer. MS (ISP): 814.3 ($MH^+$). $^1$H-NMR ($CDCl_3$) diagnostic signals only: 0.94 (t, 3H), 1.03 (d, 3H), 1.12 (d, 3H), 1.24 (d, 3H), 1.28 (s, 3H), 1.30 (d, 3H), 1.61 (s, 3H), 1,55–1,75 (m, 2H), 1.74 (d, 3H), 2.26 (s, 6H), 2.63 (s, 3H), 3.05–3.20 (m, 3H), 3.46 (m, 1H), 3.62 (m, 1H), 3.80 (s, 3H), 4.06 (d, 1H), 4.61 (dd, 2H), 5.53 (dd, 1H), 6.91 (d, 2H), 7.46 (d, 2H).

EXAMPLE 3

Preparation of I-3, compound of formula I, where $R^1$ is (3-nitro-2-pyridinyl)dithio, $R^2$ is hydrogen, $R^3$ is methyl and Z is oxygen.

[A] (3R or S, 3aR, 4R or S, 6R, 8R, 9R, 10R, 12R, 15R, 15aS)-9-[[2-O-Acetyl-3,4,6-trideoxy-3-(dimethylamino)-β-D-xylo-hexopyranosyl]oxy]-15-ethyloctahydro-8-methoxy-4,6,8,10,12,15a-hexamethyl-3-[(3-nitro-2-pyridinyl)dithio]-2H-furo [2,3-c]oxacyclo-tetradecin-2,5,11,13 (3H,6H,12H)-tetrone; (XV-3)

To a solution of compound XII-1 (1 g, 1.24 mmol) in 25 ml dichloromethane at room temperature was added 3-nitro-2-pyridinesulfenylchloride (0.473 g, 2.48 mmol) and trifluoroacetic acid (0.285 ml, 3.72 mmol). The reaction mixture was stirred at room temperature for 1 h. The deeply red colored mixture was taken up with 50 ml dichloromethane and washed with 40 ml aqueous 3% $NaHCO_3$, 40 ml water and 40 ml brine, dried over sodium sulfate and evaporated. Chromatography of the crude product on silica gel eluting with a gradient of 0 to 10% methanol/ammonium hydroxide 9:1 in dichloromethane gave the title compound as a greenish foam. MS (ISP): 840.3 ($MH^+$).

Deprotection of XV-3 was performed as described in example 1G to give product I-3 as a greenish foam as a single diastereomer. MS (ISP): 798.3 ($MH^+$). $^1$H-NMR ($CDCl_3$) diagnostic signals only: 1.02 (t, 3H), 1.05 (d, 3H), 1.16 (d, 3H), 1.24 (d, 3H), 1.34 (s, 3H), 1.38 (d, 3H), 1.54 (s, 3H), 1,55–1,75 (m, 2H), 2.26 (s, 6H), 2.79 (s, 1H), 2.86 (s, 3H), 3.05–3.20 (m, 3H), 3.46 (m, 1H), 3.55 (m, 1H), 3.89 (q, 1H), 4.28 (d, 1H), 4.34 (d, 1H), 5.91 (dd, 1H), 7.33 (dd, 1H), 8.49 (d, 1H), 8.83 (d, 1H).

EXAMPLE 4

Preparation of (3R or S, 3aR, 4R or S, 6R, 8R, 9R, 10R, 12R, 15R, 15aS)-3-[[2-(2-amino-quinolin-8-yl) 2-oxoethyl]-thio]-15-ethyloctahydro-8-methoxy-4,6,8,10,12,15a-hexamethyl-9-[[-3,4,6-trideoxy-3-(dimethylamino)-β-D-xylo-hexopyranosyl]oxy]-2H-furo [2,3-c] oxacyclotetradecin-2,5,11,13 (3H,6H,12H)-tetrone (I-4) compound of formula I, where $R^1$ is [2-(8-quinolinylamino)-2-oxoethyl]thio, $R^2$ is hydrogen, $R^3$ is methyl and Z is oxygen.

To a solution of 30 mg (36 μmol) of compound XV-3 in 1 ml DMF and 0.05 ml water under argon at room temperature was added 7,2 mg (36 μmol) tributyl phosphine and the reaction mixture was stirred for 15 min. A MS spectrum of an aliquot of the reaction mixture shows the presence of the unstable thiol XVI, where $R^2$ is hydrogen, $R^7$ is methyl, $Rp_1$ is acetyl and Z is oxygen (scheme 3). MS (ISP): 686.2 ($MH^+$). The mixture was then treated sequentially with 2 mg sodium iodide, 25 mg (71 μmol) 2-bromo-N-quinolin-8-yl-acetamide and 21.7 mg DBU (143 μmol) and stirred for 30 min. at room temperature. The solvents were evaporated under reduced pressure at 30° C. and the crude residue dissolved in 3 ml methanol and stirred for 72 h at room temperature. The solution was concentrated under vacuum at 30° C. and the residue purfied by HPLC RP-C18 with a gradient of 10 to 50% acetonitrile in water/formic acid 99.5:0.5 to give 17.6 mg (59%) of the title compound as a slightly beige amorphous compound as a single diastereomer. MS (ISP): 828.4 ($MH^+$). $^1$H-NMR ($CDCl_3$) diagnostic signals only: 0.89 (t, 3H), 1.09 (2d, 6H), 1.26 (s, 3H), 1.32 (d, 3H), 1.40 (d, 3H), 1.51 (s, 3H), 1,55–1,80 (m, 3H), 1.94 (m, 1H), 2.35 (s, 6H), 2.50 (m, 1H), 2.69 (s, 1H), 2.83 (s, 3H), 3.00–3.30 (m, 3H), 3.58 (m, 1H), 3.82 (d, 1H), 3.84 (q, 1H), 4.06 (s, 1H), 4.09 (s, 1H), 4.25 (d, 1H), 4.35 (s, 1H), 4.50 (s, 1H), 5.58 (dd, 1H), 7.41 (m, 1H), 7.51 (m, 2H), 8.12 (dd, 1H), 8.79 (m, 1H), 8.81 (1H).

EXAMPLE 5

Preparation of I-5 compound of formula I, where $R^1$ is [2-methoxy-2-oxoethyl]-thio, $R^2$ is hydrogen) $R^3$ is methyl and Z is oxygen.

The title compound was prepared according to example 4 starting from XV-3 and bromoacetic acid methyl ester. MS (ISP): 716.3 ($MH^+$). $^1$H-NMR ($CDCl_3$) diagnostic signals only: 0.86(t, 3H), 0.98 (d, 3H), 1.16 (d, 3H), 1.32 (d, 3H), 1.35 (s, 3H), 1.51 (s, 3H), 1,55–1,80 (m, 3H), 1.94 (m, 1H), 2.38 (s) 6H), 2.60 (s, 1H), 2.79 (s, 3H), 3.00–3.30 (m, 3H), 3.80 (s, 3H), 3.82 (q, 1H), 4.26 (d, 1H), 4.37 (d, 1H), 4.54 (s, 1H), 5.53 (dd, 1H).

EXAMPLE 6

Preparation of I-6 compound of formula I, where $R^1$ is [2-(3,4-dihydro-1H-2-oxo-quinolin-6-yl)-2-oxoethyl]thio, $R^2$ is hydrogen, $R^3$ is methyl and Z is oxygen.

The title compound was prepared according to example 4 starting from XV-3 and 6-(2-bromo-acetyl)-3,4-dihydro-1H-quinolin-2-one. MS (ISP): 831.2 ($MH^+$). $^1$H-NMR ($CDCl_3$) diagnostic signals only: 0.91(t, 3H), 1.11 (d, 3H), 1.15 (d, 3H), 1.25 (s, 3H), 1.31 (d, 3H), 1.38 (d, 3H), 1.51 (s, 3H), 1,55–1,80 (m, 3H), 1.94 (m, 1H), 2.39 (s, 6H), 2.65 (s, 3H), 2.90–3.10 (m, 4H), 3.24 (m, 1H), 3.82 (q, 1H), 4.26 (d, 1H), 4.29 (d, 1H), 4.34 (s, 1H), 4.40 (s, 1H), 5.58 (dd, 1H), 6.76 (d, 1H), 7.78 (m, 1H), 7.84(d, 1H), 7.88 (s, 1H).

EXAMPLE 7

Preparation of I-7 compound of formula I, where $R^1$ is [2-oxo-2-(pyridin-2-yl)ethyl]thio, $R^2$ is hydrogen, $R^3$ is methyl and Z is oxygen.

The title compound was prepared according to example 4 starting from XV-3 and 2-bromo-1-pyridin-2-yl-ethanone. MS (ISP): 763.2 (MH$^+$). $^1$H-NMR (CDCl$_3$) diagnostic signals only: 0.89(t, 3H), 1.11 (d, 3H), 1.21 (s, 3H), 1.25 (d, 3H), 1.31 (d, 3H), 1.38 (d, 3H), 1.51 (s, 3H), 1,55–1,80 (m, 3H), 1.95 (m, 1H), 2.31 (s, 6H), 2.48 (s, 3H), 2.61 (s, 1H), 3.01 (m, 1H), 3.11 (m, 1H), 3.20 (m, 1H), 3.55 (m, 1H), 3.82 (q, 1H), 4.21 (d, 1H), 4.32 (d, 1H), 4.34 (s, 1H), 4.40 (d, 1H), 4.46 (s, 1H), 4.63(d, 1H), 5.49 (dd, 1H), 7.41 (m, 1H), 7.83 (m, 1H), 8.21(d, 1H), 8.61 (m, 1H).

EXAMPLE 8

Preparation of I-8 compound of formula I, where R$^1$ is 3-[3-oxo-3-(1,2,3,4-tetrahydro-isoquinolin-2-yl)propyl] thio, R$^2$ is hydrogen, R$^3$ is methyl and Z is oxygen.

The title compound was prepared according to example 4 starting from XV-3 and 1,2,3,4-tetrahydro-2-(1-oxo-2-propenyl)-isoquinoline. MS (ISP): 831.3 (MH$^+$). $^1$H-NMR (CDCl$_3$) diagnostic signals only: 0.87(t, 3H), 1.11 (d, 3H), 1.14 (d, 3H), 1.25 (s, 3H), 1.28 (d, 3H), 1.31 (d, 3H), 1.38 (d, 3H), 1.51 (s, 3H), 1,55–1,80 (m, 3H), 1.95 (m, 1H), 2.27 (s, 6H), 2.63 (s, 1H), 2.69 (s, 3H), 2.70–3.30 (m, 6H), 3.48 (m, 1H), 3.70–3.90 (m, 6H), 4.22 (m, 1H), 4.42 (d, 1H), 4.70 (m, 4H), 5.41 (dd, 1H), 7.10–7.20 (m, 4H).

EXAMPLE 9

Preparation of I-9 compound of formula I, where R$^1$ is 3-[[[2-(6-amino-9H-purin-9-yl)ethyl]methylamino]-ethyl] thio, R$^2$ is hydrogen, R$^3$ is methyl and Z is oxygen.

A][[2-(6-amino-9H-purin-9-yl) ethyl]methylamino]-ethanol 0.6 g (3 mmol) 9-(chloroethyl)-6-amino-9H-purine (*Chemistry of Heterocyclic Compounds*, 1996, 32, 333–337) was dissolved in 10 ml n-butanol and treated with 0.684 g (9 mmol) of N-methylaminoethanol at 110° C. for 18 h. The solvent was evaporated under reduced pressure and the crude mixture purified by flash chromatography on silica gel with a gradient of 0 to 25% methanol in dichloromethane to yield 0.68 g (94%) of a light orange solid. MS (ISP): 237.3 (MH$^+$).

B] Ethanethioic acid, S-[2-[(6-amino-9H-purin-9-yl)ethyl] methylamino]ethyl]ester Diisopropylazodicarboxylate (0.829 g, 4.1 mmol) was added dropwise to a solution of 1.075 g (4.1 mmol) triphenylphosphine in 20 ml THF kept at 0° C. The mixture was stirred for 30 minutes and then a solution of 0.473 g (2 mmol) of [[2-(6-amino-9H-purin-9-yl) ethyl]methylamino]-ethanol and 0.312 g thioacetic acid (4.1 mmol) in 20 ml THF was added. The reaction mixture was stirred at 0° C. for 2 h and overnight at RT. After evaporation under reduced pressure, the residue was purified by flash chromatography on silica gel with a gradient of 0 to 20% methanol in dichloromethane. 0.547 g (92%) of a light yellow product was isolated. MS (ISP): 295.4 (MH$^+$).

C] [[2-(6-amino-9H-purin-9-yl)ethyl]methylamino]-1-ethanethiol:

0.27 g (0.92 mmol) ethanethioic acid, S-[2-[(6-amino-9H-purin-9-yl)ethyl]methyl-amino]ethyl] ester was suspended in 10 ml degassed methanol, kept under argon. Ammonia was bubbled through the solution for 5 minutes and the internal temperature rose to 40° C. The resulting solution was stirred for 60 minutes, then concentrated and the crude product was dried at 60° C. in vacuo. Yield: 210 mg (90%). MS (EI): 253.4 (MH$^+$).

The title compound (I-9,) was prepared according to example 1, steps B–E and G starting from [[2-(6-amino-9H-purin-9-yl) ethyl]methylamino]-1-ethanethiol and VII-1. MS (ISP): 862.5 (MH$^+$). $^1$H-NMR (CDCl$_3$) diagnostic signals only: 0.89(t, 3H), 1.11 (d, 3H), 1.15 (d, 3H), 1.27 (s, 3H), 1.28 (d, 3H), 1.31 (d, 3H), 1.40 (d, 3H), 1.52 (s, 3H), 1,55–1,80 (m, 3H), 1.95 (m, 1H), 2.26 (s, 6H), 2.31 (s, 3H), 2.63 (s, 1H), 2.75 (s, 3H), 2.70–2.90 (m, 2H), 3.02–3.25 (m, 3H), 3.40–3.60 (m, 4H), 3.84 (q, 1H), 4.25–4.40 (m, 4H), 5.41 (m, 2H), 5.49 (dd, 1H), 8.03 (s, 1H), 8.36 (s, 1H).

EXAMPLE 10

Preparation of I-10, compound of formula I wherein R$^1$ is [3-(4-phenyl-1H- pyrazol-1-yl) -propyl]thio, R$^2$ is fluoro, R$^3$ is methyl and Z is oxygen.

A] 1-(3-chloroprop-1-yl)-4-iodo-1H-pyrazole 2.0 g (10.31 mmol) 4-iodopyrazole were dissolved in 20 ml DMF and 1.22 g (10.8 mmol) potassium t-butoxide was added. The mixture was stirred for 1 hour at room temperature and 1.06 ml (10.83 mmol) 1-bromo-3-chloropropane were added. A white precipitate appeared rapidly. After 30 minutes 50 ml water was added and the reaction mixture was extracted twice with 100 ml hexane. The combined organic layers were dried over MgSO$_4$ and the solvent was removed to give 2.65 g of the desired product as a colourless oil. MS (ISP): 270.1 (MH$^+$). $^1$H-NMR (CDCl$_3$): 2.31 (quint, 2H), 3.47 (t, 2H), 4.32 (t, 2H), 7.48 (s, 1H), 7.53 (s, 1H).

B] 1-(3-chloroprop-1-yl)-4-phenyl-1H-pyrazole

To a solution of 0.50 g (1.85 mmol) 1-(3-chloroprop-1-yl)-4-iodo-1H-pyrazole in 10 ml dioxane 0.34 g (2.78 mmol) phenylboronic acid, 0.107 g (0.09 mmol) tetrakis(triphenylphosphine)-palladium(0) and 3 ml of an aqueous 2M K$_3$PO$_4$ solution were added and the solution was degassed 3 times and heated to 60° C. for 3 hours under an atmosphere of argon. 100 ml of water were added and the mixture was extracted twice with ethyl acetate. The combined organic layers were dried over Na$_2$SO$_4$ and evaporated under reduced pressure. The residue was purified by flash chromatography on silica gel (first hexane/ethyl acetate 8:2 then ethyl acetate) to give 233 mg of the desired product as yellow crystals.MS (ISP): 221.3 (MH$^+$). $^1$H-NMR (CDCl$_3$): 2.36 (quint, 2H), 3.50 (t, 2H), 4.35 (t, 2H), 7.25 (m, 1H), 7.39 (m, 1H), 7.47 (m, 1H), 7.68 (s, 1H), 7.80 (s, 1H).

C]Ethanethioic acid, S-[(4-phenyl-1H-pyrazol-1-yl)propyl] ester 0.23 g (1.04 mmol) 1-(3-chloroprop-1-yl)-4-phenyl-1H-pyrazole were dissolved in 6 ml acetone, potassium thioacetate (0.15 g, 1.3 mmol) was added and the mixture was heated to reflux during 16 hours. The solvent was evaporated under reduced pressure and the residue was purified by flash chromatography on silica gel (hexane/ethyl acetate, gradient 9:1 to 7:3) to give 240 mg of the desired product as a yellow oil. MS (EI): 260.1 (M$^+$). $^1$H-NMR (CDCl$_3$): 2.19 (quint, 2H), 2.35 (s, 3H), 2.87 (t, 2H), 4.21 (t, 2H), 7.23 (m, 1H), 7.36 (m, 1H), 7.47 (m, 1H), 7.64 (s, 1H), 7.78 (s, 1H).

D] 3-(4-phenyl-1H-pyrazol-1-yl)propanethiol 240 mg (0.92 mmol) ethanethioic acid, S-[(4-phenyl-1H-pyrazol-1-yl)propyl] ester were dissolved in 10 ml degassed methanol kept under argon. Dry ammonia was bubbled through the solution during 5 minutes and the temperature rose to approx. 40° C. The resulting solution was stirred for 1 hour and subsequently evaporated and dried in vacuo. The crude product was used immediately for the next reaction.

MS (ISP): 219.2 (MH$^+$). The title compound I-10 was prepared starting from 3-(4-phenyl-1H-pyrazol-1-yl)propanethiol and VII-1 according to example 1 steps B–G. MS (ISP): 846.4 (MH$^+$).

EXAMPLE 11

Preparation of I-11, compound of formula I wherein R$^1$ is [3-(4-phenyl-1H-pyrazol-1-yl)-propyl]sulfonyl, R$^2$ is fluoro R$^3$ is methyl and Z is oxygen.

The title compound was prepared from the product of example 10 step E following the procedures described in example 2 step A and in example 1 step G. MS (ISP): 878.4 (MH$^+$). $^1$H-NMR (CDCl$_3$) diagnostic signals only: 0.94 (t, 3H), 1.10 (d, 3H), 1.15 (d, 3H), 1.23 (d, 3H), 1.26 (s, 3H), 1.28 (s, 3H), 1.31 (d, 3H), 1.81 (s, 3H), 1.86 (s, 3H), 2.29 (s, 6H), 2.67 (s, 3H), 3.10 (s,1H), 3.17 (m, 3H), 3.44 (m, 4H), 3.63 (m, 2H), 4.10 (d, 1H), 4.32 (d, 1H), 4.39 (m, 3H), 4.71 (s, 1H), 5.51 (dd, 1H), 7.21 (m, 1H), 7.35 (t, 2H), 7.49 (d, 2H), 7.74 (s, 1H), 7.79 (s, 1H).

EXAMPLE 12

Preparation of (3R or S, 3aR, 4R or S, 6R, 8R, 9R, 10R, 12S, 15R, 15aS)-15-Ethyl-12-fluorooctahydro-8-methoxy-4,6,8,10,12,15a-hexamethyl-3-[[2-[3-(3-pyridinyl)-1H-1,2,4-triazole-1-yl]ethyl]thio]-9-[[3,4,6-trideoxy-3-(dimethylamino)-β-D-xylo-hexopyranosyl]oxy]-2H-furo [2,3-c] oxacyclotetradecin-2,5,11,13 (3H,6H,12H)-tetrone (I-12), compound of formula I where R$^1$ is [2-[3-(3-pyridinyl)-1H-1,2,4-triazol-1-yl]ethyl]thio, R$^2$ is fluoro, R$^3$ is methyl and Z is oxygen.

A] 3-(3-Pyridinyl)-1,2,4-triazole was prepared according to Lin et al. *J. Org. Chem.* 1979, 44, 4160.

B] 1-(2-Hydroxyethyl)-3-(3-pyridinyl)-1H-1,2,4-triazole
3-(3-Pyridinyl)-1,2,4-triazole (1.6 g, 10.9 mmol) was suspended in DMF (50 ml) and 0.964 g (10.9 mmol) ethylene carbonate was added. After addition of a catalytic amount of NaOH (8 mg), the mixture was stirred at 160° C. for 2 hours. DMF was removed in vacuo and the residue was crystallized from EtOH to give the desired product as a solid. MS (EI): 190.1 (M$^+$). $^1$H-NMR (DMSO-d6): 3.80 (q, 2H), 4.29 (t, 2H), 5.01 (t, 1H), 7.50 (m, 1H), 8.31 (m, 1H), 8.59 (s, 1H), 8.62 (m, 1H), 9.17 (d, 1H).

C] 1-(2-Chloroethyl)-3-(3-pyridinyl)-1H-1,2,4-triazole
122 g (6.4 mmol) 1-(2-hydroxyethyl)-3-(3-pyridinyl)-1H-1,2,4-triazole were suspended in 15 ml thionyl chloride and heated at 70° C. for 45 minutes. Excess thionyl chloride was removed in vacuo and the residue was dissolved in water (100 ml). The aqueous solution was basified with NaHCO$_3$ solution (10%) and the resulting slurry was stirred for 15 minutes. The product was isolated by filtration, washed with water and dried to give the desired product as a brownish solid. MS (EI): 208.1 (M$^+$). $^1$H-NMR (DMSO-d6): 3.97 (t, 2H), 4.54 (t, 2H), 7.38 (m, 1H), 8.21 (s, 1H), 8.36 (m, 1H), 8.65 (m, 1H), 9.34 (d, 1H).

D] Ethanethioic acid, S-[[3-(3-pyridinyl)-1H-1,2,4-triazole-1-yl]ethyl] ester:
The title compound was obtained from 1-(2-chloroethyl)-3-(3-pyridinyl)-1H-1,2,4-triazole following the procedure described in example 10 step C. MS (EI): 248.1 (M$^+$). $^1$H-NMR (DMSO-d6): 2.34 (s, 3H), 3.36 (t, 2H), 4.44 (t, 2H), 7.51 (m, 1H), 8.31 (m, 1H), 8.63 (m, 1H), 8.67 (s, 1H), 9.16 (d, 1H).

E] 2-[3-(3-Pyridinyl)-1H-1,2,4-triazole-1-yl]ethanethiol:
The title compound was obtained from ethanethioic acid, S-[[3-(3-pyridinyl)-1H-1,2,4-triazole-1-yl]ethyl] ester following the procedure described in example 10 step D. MS (EI): 206.1 (M$^+$). $^1$H-NMR (DMSO-d6): 2.50 (broad t, 1H), 2.98 (broad q, 2H), 4.41 (t, 2H), 7.51 (m, 1H), 8.31 (m, 1H), 8.62 (m, 1H), 8.67 (s, 1H), 9.17 (s, 1H).

F] (10E)-3-de[(2,6-dideoxy-3-C-methyl-3-O-methyl-α-L-ribo-hexopyranosyl)oxy]-10,11-didehydro-11-deoxy-6-O-methyl-3-oxo-Erythromycin 2'-acetate (XXX-12)
To a solution of 0.4 g (0.65 mmol) of (10E)-3-O-de(2,6-dideoxy-3-C-methyl-3-O-methyl-α-L-ribo-hexopyranosyl)-10,11-didehydro-11-deoxy-6-O-methyl-erythromycin-2'-acetate (XXIX, where R$^7$ is methyl, Rp$_1$ is acetyl; *J. Med. Chem.* 1998, 41, 1651–1659) in 5 ml dichloromethane were added dropwise at room temperature 2.76 g (0.98 mmol) of a 15% wt solution of Dess-Martin reagent in dichloromethane over a period of 10 minutes under argon. The reaction mixture was stirred for 1 h30 at room temperature. The resulting yellow solution was diluted with 5 ml diethyl ether and then poured into a mixture of 45 g of a 10% aqueous solution of Na$_2$S$_2$O$_3$ and 4 g of a saturated NaHCO$_3$ solution and stirred for 1 h. The organic layer was separated, the aqueous phase was extracted twice with 25 ml of diethylether. The combined organic phases were washed with 20 ml of 3% NaHCO$_3$, 20 ml water, 20 ml brine, dried over Na$_2$SO$_4$ and evaporated. Flash chromatography on silica gel with dichloromethane/methanol/ammonia 90:10:1 gave 0.36 g (90%) of XXX-12 as a colourless solid. MS (ISP): 612.7 (MH$^+$). $^1$H-NMR (CDCl$_3$) diagnostic signals only: 0.93(t, 3H), 1.11 (d, 3H), 1.15 (d, 3H), 1.22 (d, 3H), 1.31 (s, 3H), 1.35 (d, 3H), 1.48 (s, 3H), 1,55–2,00 (m, 6H), 2.01 (s, 3H), 2.04 (s, 3H), 2.24 (s, 6H), 2.65 (m, 1H), 2.86 (s, 3H), 3.00–3.20 (m, 2H), 3.54 (m, 1H), 3.72 (q, 1H), 4.17 (d, 1H), 4.36 (d, 1H), 4.71 (m, 1H), 4.98 (dd, 1H), 6.59 (s, 1H).

G] (10E)-3-de[(2,6-dideoxy-3-C-methyl-3-O-methyl-α-L-ribo-hexopyranosyl)oxy]-10,11-didehydro-11-deoxy-2-fluoro-6-O-methyl-3-oxo-Erythromycin 2'-acetate (XXXI-12)
This compound was obtained according to example 1F from XXX-12 (0.5 g) and N-fluorobenzenesulfonimide (0.283 g). Yield: 0.24 g (46%). MS (ISP): 630.2 (MH$^+$). $^1$H-NMR (CDCl$_3$) diagnostic signals only: 0.95(t, 3H), 1.16 (d, 3H), 1.17 (d, 3H), 1.22 (d, 3H), 1.28 (s, 3H), 1.49 (s, 3H), 1,73 (d, 3H), 1.96 (s, 3H), 2.03 (s, 3H), 2.25 (s, 6H), 2.67 (s, 3H), 3.46 (m, 2H), 3.96 (d, 1H), 4.72 (dd, 1H), 5.03 (dd, 1H), 6.59 (s, 1H).

H] (10E)-3-de[(2,6-dideoxy-3-C-methyl-3-O-methyl-α-L-ribo-hexopyranosyl)oxy]-10,11-didehydro-11-deoxy-2-fluoro-6-O-methyl-3-oxo-erythromycin 2'-acetate 12-(chloroacetate) (XXXII-12):
This compound was obtained according to example 1A from XXXI-12 (0.15 g) and chloroacetic acid (67mg). Yield: 0.148 g (88%). MS (ISP): 706.3 (MH$^+$). $^1$H-NMR (CDCl$_3$) diagnostic signals only: 0.97(t, 3H), 1.16 (d, 3H), 1.17 (d, 3H), 1.22 (d, 3H), 1.28 (s, 3H), 1.49 (s, 3H), 1,71 (s, 3H), 1.73 (d, 3H), 2.09 (s,3H), 2.26 (s, 6H), 2.65 (s, 3H), 3.03 (m, 2H), 3.46 (m, 2H), 4.01 (s, 2H), 4.39 (d, 1H), 4.76 (m, 1H), 4.97 (d broad, 1H), 6.64 (s, 1H).

I] (10E)-3-de[(2,6-dideoxy-3-C-methyl-3-O-methyl-α-L-ribo-hexopyranosyl)oxy]-10,11-didehydro-11-deoxy-2-fluoro-6-O-methyl-3-oxo-erythromycin 2'-acetate 12-[[[2-[3-(3-pyridinyl)-1H-1,2,4-triazole-1-yl]ethyl]thio]acetate] (XXXIII-12)

To a solution of 35 mg (49.6 μmol) XXXII-12 dissolved in 3 ml acetone were added 8.1 μl DBU and a catalytic amount of sodium iodide. 10.7 mg (52.0 μmol) 2-[3-(3-pyridinyl)-1H-1,2,4-triazole-1-yl]ethanethiol were added in one portion and the solution was stirred for 1 hour at room temperature. The reaction mixture was diluted with $CH_2Cl_2$ washed with 5% aqueous $NaHCO_3$, dried over $Na_2SO_4$ and evaporated. The crude product was purified by flash chromatography on silica gel ($CH_2Cl_2$/MeOH/$NH_3$ 95:5:0.01) to give 35 mg of the desired product as a foam. MS (ISP): 876.3 ($MH^+$), 439.1 ($[MH_2]^{++}$). $^1$H-NMR ($CDCl_3$), diagnostic signals only: 0.94 (t, 3H), 1.16 (d, 3H), 1.24 (d, 3H), 2.08 (2, 3H), 2.25 (s, 6H), 3.15 (s, 3H), 3.4–3.55 (m, 2H), 3.97 (d, 1H), 4.35–4.44 (m, 4H), 4.74 (dd, 1H), 5.46 (dd, 1H), 6.62 (s, br, 1H), 7.37 (dd, 1H), 8.19 (s, 1H), 8.35 (m, 1H), 8.64 (m, 1H), 9.32 (m, 1H).

K] (3R or S, 3aR, 4 R or S, 6R, 8R, 9R, 10R, 12S, 15R, 15aS)-9-[[2-O-Acetyl-3,4,6-trideoxy-3-(dimethylamino)-β-D-xylo-hexopyranosyl]oxy]-15-ethyl-12-fluorooctahydro-8-methoxy-4,6,8,10,12,15a-hexamethyl-3-[[2-[3-(3-pyridinyl)-1H-1,2,4-triazole-1-yl]ethyl]thio]-2H-furo [2,3-c] oxacyclotetradecin-2,5,11,13 (3H,6H,12H)-tetrone (XXXIV-12)

To a solution of 11.4 mg (13.0 μmol) XXXIII-12 in 2 ml dry DMF kept under argon at −5° C. were added 17.0 μl of a solution of potassium t-butoxide (1M in THF). The reaction mixture was stirred at −10 to −5° C. for 1 hour. The reaction was subsequently quenched with 2 ml of a saturated ammonium chloride solution and partitioned between ethyl acetate and 3% aqueous $NaHCO_3$. The organic layer was washed twice with 3% aqueous $NaHCO_3$ and once with half saturated brine, dried over $Na_2SO_4$ and evaporated.

The crude product was purified by flash chromatography on silica gel ($CH_2Cl_2$/MeOH/$NH_3$ 98:2:0.01→97:3:0.01) to give 7.7 mg of the desired product as a foam as a mixture of diastereomers. MS (ISP): 876.3 ($MH^+$), 439.0 ($[MH_2]^{++}$). $^1$H-NMR ($CDCl_3$), diagnostic signals only (main isomer): 0.90 (t, 3H), 2.07 (s, 3H), 2.26 (s, 6H), 2.37 (s, 1H), 2.50 (s, 3H), 4.04 (d, 1H), 4.18 (s, 1H), 4.37 (d, 1H), 4.55–4.61 (m, 2H), 4.75 (dd, 1H), 5.28 (dd, 1H), 7.36 (m, 1H), 8.33 (m, 1H), 8.56 (s, 1H), 8.62 (m, 1H), 9.30 (m, 1H).

L] (3R or S, 3aR, 4R or S, 6R, 8R, 9R, 10R, 12S, 15R, 15aS)-15-Ethyl-12-fluorooctahydro-8-methoxy-4,6,8,10,12,15a-hexamethyl-3-[[2-[3-(3-pyridinyl)-1H-1,2,4-triazole-1-yl]ethyl]thio]-9-[[3,4,6-trideoxy-3-(dimethylamino)-β-D-xylo-hexopyranosyl]oxy]-2H-furo [2,3-c] oxacyclotetradecin-2,5,11,13 (3H,6H,12H)-tetrone (I-12)

The protected ketolide XXXIV-12 (13 mg, 14.8 mmol) was dissolved in 3 ml methanol and stirred for 5 days at room temperature. The solvent was removed under reduced pressure and the crude product was purified by flash chromatography on silica gel ($CH_2Cl_2$/MeOH/$NH_3$ 94:6:0.01) to give 6.0 mg of the desired product as a colorless solid as a single diastereoisomer. $^1$H-NMR ($CDCl_3$), diagnostic signals only: 0.90 (t, 3H), 1.15 (d, 3H), 1.18 (d, 3H), 1.27 (d, 3H), 1.29 (d, 3H), 1.35 (s, 3H), 1.75 (d, 3H),1.83–1.98 (m., 2H), 2.27 (s, 6H), 2.37 (s, 1H), 2.45, (m, 1H), 2.51 (s, 3H), 2.60–2.68 (m, 1H), 3.07 (m, 1H), 3.13–3.21 (m, 2H), 3.50–3.64 (m, 4H), 4.06 (d, 1H), 4.18 (s, 1H), 4.30 (d, 1H), 4.55–4.63 (m, 2H), 5.26 (dd, 1H), 7.35 (dd, 1H), 8.33 (m, 1H), 8.57 (s, 1H), 8.62 (n, 1H), 9.30 (m, 1H).

EXAMPLE 13

Preparation of (3R or S, 3aR, 4R or S, 6R, 8R, 9R, 10R, 12S, 15R, 15aS) -3-[[3-[6-Amino-9H-purine-9-yl]propyl]thio]-15-ethyl-12-fluorooctahydro-8-methoxy-4,6,8,10,12,15a-hexamethyl-3-9-[[3,4,6-trideoxy-3-(dimethylamino)-β-D-xylo-hexopyranosyl]oxy]-2H-furo [2,3-c] oxacyclotetradecin-2,5,11,13 (3H,6H,12H)-tetrone (I-13), compound of formula I where $R^1$ is [3-[6-Amino-9H-purine-9-yl]propyl]thio, $R^2$ is fluoro, $R^3$ is methyl and Z is oxygen.

A] 3-[6-amino-9H-purine-yl]propanethiol

This side chain was prepared from 6-amino-9-(3-chloropropyl)-9H-purine (J. Am. Chem. Soc. 1994, 116, 6089) following the procedures described in example 10, steps C and D.

The title compound I-13 was prepared starting from 3-[6-amino-9H-purine-9-yl]-propanethiol and XXXII-12 according to example 12 steps I–L with the only difference, that the cyclisation (step K) was performed at 0° C.

MS (ISP) ($MH^+$). $^1$H-NMR ($CDCl_3$), diagnostic signals only: 0.93 (t, 3H), 1.12 (d, 3H), 1.18 (d, 3H), 1.23 (d, 3H), 1.31 (d, 3H), 1.32 (s, 3H), 1.53 (s, 3H), 1.80 (d, 3H), 2.30 (s, 6H), 2,69 (s, 3H), 4.08 (d, 1H), 4.14 (s, 1H), 4.32 (d, 1H), 4.33–4.50 (m, 4H), 5.35 (dd, 1H), 5.48 (s, broad, 2H), 8.15 (s, 1H), 8.36 (s, 1H).

EXAMPLE 14

Preparation of (3R or S) 3aR, 4R or S, 6R, 8R, 9R, 10R, 12S, 15R, 15aS)-15-Ethyl-12-fluorooctahydro-8-methoxy-4,6,8,10,12,15a-hexamethyl-3-[[2-[[5-methyl-2,4-(1H,3H)-pyrimidinedione-1-yl]methoxy]ethyl]thio]-9-[[3,4,6-trideoxy-3-(dimethylamino)-β-D-xylo-hexopyranosyl]oxy]-2H-furo [2,3-c] oxacyclotetradecin-2,5,11,13 (3H,6H,12H)-tetrone (I-14), compound of formula I where $R^1$ is [2-[[5-methyl-2,4-(1H,3H) -pyrimidinedione-1-yl]methoxy]ethyl]thio, $R^2$ is fluoro, $R^3$ is methyl and Z is oxygen.

A] 1-[(2-Hydroxyethoxy)methyl]-5-methyl-2,4(1H,3H)-pyrimidinedione

The title compound was prepared according to Ubasawa et al., Chem. Pharm. Bull., 1995, 43, 142–143.

B] 1-[(2-Chloroethoxy)methyl]-5-methyl-2,4(1H,3H)-pyrimidinedione 150 mg (0.75 mmol) 1-[(2-hydroxyethoxy)methyl]-5-methyl-2,4(1H,3H)-pyrimidinedione were dissolved in 10 ml pyridine and 1 g PS-triphenylphosphine resin (3 mmol/g) and 147 μl carbontetrachloride were added. The reaction was stirred at room temperature for 3 days. The reaction mixture was diluted with a mixture of ethyl acetate and methanol and centrifuged. The supernatant was decanted and the solvent was evaporated under reduced pressure. The residue, dissolved in ethyl acetate and a small amount of methanol, was purified by flash chromatography on silica gel (ethyl acetate). The fractions containing the product were pooled and the volume was reduced to about 3 ml. Upon addition of hexane the product crystallized to give 97 mg of white crystals. MS (ISP): 217.1 ($M-H^+$). $^1$H-NMR (DMSO-$d_6$): 1.77 (d, 3H), 3.69–3.77 (m, 4H), 5.10 (s, 2H), 7.59 (d, 1H), 11,32 (s, br, 1H).

C] Ethanethioic acid, S-[2-[[-5-methyl-2,4(1H,3H)-pyrimidinedione-1-yl]methoxy]ethyl] ester 92.0 mg (421 μmol) 1-[(2-chloroethoxy)methyl]-5-methyl-2,4(1H,3H)-pyrimidinedione were suspended in 6 ml acetone and 60.1 mg (526 μmol) potassium thioacetate were added and the reaction mixture was heated to reflux for 6 hours. The suspension was concentrated in vacuo and ethyl acetate was added. The organic layer was washed with water, dried over $Na_2SO_4$ and evaporated. The crude product was purified by flash chromatography on silica gel (ethyl acetate/hexane 9:1) to give 73 mg of the desired product. MS (ISP): 259.1 (MH$^+$), 281.1 (MNa$^+$). $^1$H-NMR (DMSO-d$_6$): 1.76 (d, 3H), 2.32 (s, 3H), 3.01 (t, 2H), 3.58 (t, 2H), 5.04 (s, 2H), 7.57 (d, 1H), 11.32 (s, br, 1H).

D] 2-[[5-methyl-2,4-(1H,3H)-pyrimidinedione-1-yl]methoxy]ethanethiol

The title compound was prepared from 20 mg (77.4 µmol) ethanethioic acid, S-[2-[[-5-methyl-2,4(1H,3H)-pyrimidinedione-1-yl]methoxy]ethyl] ester following the procedure described in example 10 step D. The crude product was used immediately for the next reaction.

The title compound I-14 was prepared starting from 2-[[5-methyl-2,4-(1H,3H)-pyrimidinedione-1-yl]methoxy] ethanethiol and XXXII-12 according to example 12 steps I–L with the only difference that the cyclisation (step K) was performed at 0° C. The product was isolated as a mixture of two isomers. MS (ISP) 844.3 (MH$^+$).

EXAMPLE 15

Preparation of (3R or S, 3aS, 4R or S, 6R, 8R, 9R, 10R, 12R, 15R, 15aS) -15-Ethylhexadecahydro-4,6,8,10,12,15a-hexamethyl-2,5,11,13-tetraoxo-8-[[(2E)-3-(3-quinolyl)-2-propen-1-yl]oxy]-9-[[3,4,6-trideoxy-3-(dimethylamino)-β-D-xylo-hexopyranosyl]oxy]-2H-furo [2,3-c] oxacyclotetradecin-3-carbonitrile (I-15), compound of formula I where R$^1$ is cyano, R$^2$ is hydrogen, R$^3$ is 3-(3-quinolyl)-2-propen-1-yl and Z is oxygen.

A] 6-O-2-Propen-1-yl-erythromycin A 2',4"-dibenzoate (III-15)

6-O-2-Propen-1-yl-erythromycin A 2',4"-dibenzoate was prepared following procedures described in WO0078773.

B] 6-O-2-Propen-1-yl-erythromycin A cyclic 11,12 carbonate 2',4"-dibenzoate (IV-15)

To a solution of 500 mg (509 µmol) 6-O-2-propen-1-yl-erythromycin A 2',4"-dibenzoate (III-15) in 30 ml THF at –20° C. kept under argon 305 µl (305 µmol) of a solution of sodium bis(trimethylsilyl)amide (1M in THF) were added. After 10 minutes 165 mg (1.02 mmol) 1,1'-carbonyldiimidazole were added and the temperature was allowed to rise to –5° C. The reaction was stirred at –5° C. to 0° C. over night and additional sodium bis(trimethylsilyl)amide (600 µl, 1M in THF) and 1,1'-carbonyldiimidazole (83 mg, 0.51 mmol) were added. The reaction was stirred at –5° C. to 0° C. until no starting material remained. The mixture was hydrolysed with water and ethyl acetate was added. The organic layer was washed with saturated NaHCO$_3$ and brine, dried over Na$_2$SO$_4$ and evaporated. The crude product (500 mg) was used for the next reaction without further purification. MS (ISP): 1008.4 (MH$^+$)

C] (10E)-10,11-Didehydro-11-deoxy-6-O-2-propen-1-yl-erythromycin A 2',4"-dibenzoate (VI-15)

500 mg (496 µmol) 6-O-2-Propen-1-yl-erythromycin A cyclic 11,12 carbonate 2',4"-dibenzoate were dissolved in 10 ml benzene and 185 µl (1.24 mmol) DBU were added. The reaction was heated to reflux for 12 hours and diluted with ethyl acetate. The organic layer was washed with saturated aqueous NaHCO$_3$, dried over Na$_2$SO$_4$ and evaporated. The crude product was purified by flash chromatography on silica gel (ethyl acetate/hexane 7:3) to give 200 mg of the desired product as a solid. MS (ISP): 964.4 (MH$^+$), $^1$H-NMR (CDCl$_3$), diagnostic signals only: 0.78 (d, 3H), 0.84 (t, 3H), 0.98 (d, 3H), 1.68–1.91 (m, 6H), 1.97 (s, 3H), 2.32 (s, 6H), 2.45 (d, 1H), 2.74–2.85 (m, 1H), 2.88–2.03 (mn, 1H), 3.27–3.38 (m, 1H), 3.48 (s, 3H), 3.71 (d, 1H), 3.78–3.94 (m, 2H), 3.98–4.15 (m, 2H), 4.45–4.58 (m, 1H), 4.82 (d, 1H), 4.87–5.00 (m, 3H), 5.02–5.14 (m, 2H), 5.24 (dd, 1H), 6.49 (s, 1H), 7.36–7.65 (m , 6H), 7.95–8.09 (m, 4H).

D] (10E)-10,11-Didehydro-11-deoxy-6-O-2-propen-1-yl-erythromycin A 2',4"-dibenzoate 12-(chloroacetate) (VII-15)

The title compound was prepared starting with 166 mg of VI-15 according to the procedure described in example 1, step A to give 128 mg of purified product. MS (ISP): 1040.5 (MH$^+$).

E] (3R or S, 3aS, 4R or S, 6R, 8R, 9R, 10R, 12R, 15R, 15aS) - 9-[[2-O-Benzoyl-3,4,6-trideoxy-3-(dimethylamino)-β-D-xylo-hexopyranosyl]oxy]-11-[[2,6-dideoxy-3-C-methyl-3-O-methyl-4-O-(benzoyl-α-L-ribo-hexopyranosyl)oxy]-15-ethylhexadecahydro-4,6,8,10,12,15a-hexamethyl-2,5,13-trioxo-8-[(2-propen-1-yl)oxy]-2H-furo [2,3-c] oxacyclotetradecin-3-carbonitrile (IX-15)

200 mg (192 µmol) VII-15 were dissolved in 5 ml dichloromethane at 0° C. and 96.5 mg (359 µmol) tetrabutylammonium cyanide were added. The temperature was allowed to rise to room temperature. After 4 hours more tetrabutylammonium cyanide (25 mg, 93 µmol) was added and the reaction was stirred over night at room temperature. The reaction mixture was heated to 40° C. during 4 hours. The solvent was evaporated and the residue was purified by flash chromatography on silica gel (CH$_2$Cl$_2$/MeOH 9:1) to give 170 mg of the desired product (mixture of diastereoisomers) as a solid. MS (ISP): 1031.4 (MH$^+$).

F] (3R or S, 3aS, 4R or S, 6R, 8R, 9R, 10R, 12R, 15R, 15aS)-9-[[2-O-Benzoyl-3,4,6-trideoxy-3-(dimethylamino)-β-D-xylo-hexopyranosyl]oxy]-15-ethylhexadecahydro-11-hydroxy-4,6,8,10,12,15a-hexamethyl-2,5,13-trioxo-8-[(2-propen-1-yl)oxy]-2H-furo [2,3-c] oxacyclotetradecin-3-carbonitrile (XI-15)

Compound IX-15 (170 mg, 165 µmol) was dissolved in a mixture of 0.83 ml ethanol and 0.83 ml 2N hydrochloric acid and heated to 45° C. for 4 hours. The reaction was then stirred at room temperature during 16 hours. 0.83 ml 3N sodium hydroxide were added and the reaction mixture was extracted with ethyl aceteate. The organic layer was washed with saturated aqueous NaHCO$_3$, dried over Na$_2$SO$_4$ and evaporated. The crude product was purified by flash chromatography on silica gel (CH$_2$Cl$_2$/MeOH 95:5) to give 100 mg of the desired product as a solid as a mixture of diastereomers. MS (ISP): 769.2 (MH$^+$).

G] (3R or S, 3aS, 4R or S, 6R, 8R, 9R, 10R, 12R, 15R, 15aS)-9-[[2-O-Benzoyl-3,4,6-trideoxy-3-(dimethylamino)-β-D-xylo-hexopyranosyl]oxy]-15-ethylhexadecahydro-4,6,8,10,12,15a-hexamethyl-2,5,11,13-tetraoxo-8-[(2-propen-1-yl)oxy]-2H-furo [2,3-c] oxacyclotetradecin-3-carbonitrile (XII-15)

100 mg (130 µmol) XI-15, 167.0 mg (871 µmol) EDC*HCl and 166.3 µl (2.34 mmol) DMSO were dissolved in 8 ml dichloromethane at 0° C. and a solution of 168.3 mg (871 µmol) pyridinium trifluoroacetate in 2 ml dichloromethane was added over a period of 10 minutes. The reaction mixture was stirred at room temperature during two hours. The solution was diluted with dichloromethane, washed with 3% aqueous NaHCO$_3$, dried over Na$_2$SO$_4$ and evaporated. The crude product was purified by flash chromatography on silica gel (ethyl acetate/hexane 7:3) to give 57 mg of the desired product as a solid as a mixture of diastereomers. MS (ISP): 767.2 (MH$^+$), $^1$H-NMR (CDCl$_3$), diagnostic signals only: 0.88 (t, 3H), 0.99 (d, 3H), 1.03 (d, 3H), 1.10 (d, 3H), 1.49 (s 3H), 2.27 (s, 6H), 2.56–2.66 (m, 1H), 2.80–2.95 (m, 1H), 2.97–3.17 (m, 4H), 3.60–3.84 (m, 5H), 4.39 (d, 1H), 4.61 (d, 1H), 4.69 (d, 1H), 4.98–5.13 (m, 4H), 5.39 (dd, 1H), 5.60–5.76 (m, 1H), 7.39–7.48 (m, 2H), 7.52–7.60 (m, 1H), 7.98–8.06 (m, 2H).

H] (3R or S, 3aS, 4R or S, 6R, 8R, 9R, 10R, 12R, 15R, 15aS)-9-[[2-O-Benzoyl-3,4,6-trideoxy-3-(dimethylamino)-β-D-xylo-hexopyranosyl]oxy]-15-ethylhexadecahydro-4,6,8,10,12,15a-hexamethyl-2,5,11,13-tetraoxo-8-[[(2E)-3-(3-quinolyl)-2-propen-1-yl]oxy]-2H-furo [2,3-c] oxacyclotetradecin-3-carbonitrile (XIII-15)

The product of step G (50 mg, 65 μmol), 2.9 mg (13 μmol) palladium(II)acetate, 6 mg (20 μmol) tri-o-tolylphosphine, 27.1 mg (130 μmol) 3-bromoquinoline and 27.1 μl (196 μmol) triethylamine were dissolved in 1 ml acetonitrile in an autoclave and the solution was degassed and heated to 90° C. during 36 hours. The reaction mixture was diluted with dichloromethane washed with aqueous NaHCO$_3$, dried over Na$_2$SO$_4$ and evaporated. The crude product was purified by flash chromatography on silica gel (CH$_2$Cl$_2$/MeOH 98:2) to give 40 mg of the desired product as a foam as a mixture of diastereoisomers. MS (ISP): 894.3 (MH$^+$), 448.0 ([MH$_2$]$^{++}$).

I] (3R or S, 3aS, 4R or S, 6R, 8R, 9R, 10R, 12R, 15R, 15aS)-9-[[3,4,6-trideoxy-3-(dimethylamino) -β-D-xylo-hexopyranosyl]oxy]-15-ethylhexadecahydro-4,6,8,10,12,15a-hexamethyl-2,5,11,13-tetraoxo-8-[[(2E)-3-(3-quinolyl)-2-propen-1-yl]oxy]-2H-furo [2,3-c] oxacyclotetradecin-3-carbonitrile (I-15)

Compound XIII-15 (23 mg, 26 μmol) was dissolved in 3 ml methanol and heated to reflux for 5 hours. The solvent was removed and the residue was purified by flash chromatography on silica gel (CH$_2$Cl$_2$/MeOH 98:2) to give 11.7 mg of the desired product as a light yellow solid as a single diastereoisomer. MS (ISP): 790.5 (MH$^+$), 396.0 ([MH$_2$]$^{++}$). $^1$H-NMR (CDCl$_3$), diagnostic signals only: 0.93 (t, 3H), 1.07 (d, 3H), 1.09 (d, 3H), 1.15 (d, 3H), 1.37 (d, 3H), 1.42 (d, 3H), 1.44 (s, 3H), 1.62 (s, 3H), 2.24 (s, 6H), 2.39–2.48 (m, 1H), 2.64–2.74 (m, 1H), 3.12–3.30 (m, 4H), 3.39–3.53 (m, 2H), 3.92–4.05 (m, 2H), 4.37 (d, 1H), 4.46 (d, 1H), 4.75 (s, 1H), 5.45 (dd, 1H), 6.23–6.33 (m, 1H), 6.58 (d, 1H), 7.47–7.54 (m, 1H), 7.61–7.68 (m, 1H), 7.81–7.86 (m, 1H), 8.03–8.09 (m, 1H), 8.15 (d, 1H), 9.00 (d, 1H).

EXAMPLE 16

Preparation of (3R or S, 3aS, 4R or S, 6R, 8R, 9R, 10R, 12R, 15R, 15aS)-15-Ethylhexadecahydro-8-methoxy-4,6,8,10,12,15a-hexamethyl-2,5,11,13-tetraoxo-9-[[3,4,6-trideoxy - 3-(dimethylamino)-β-D-xylo-hexopyranosyl]oxy]-2H-furo [2,3-c] oxacyclotetradecin-3-carboxylic acid phenylmethyl ester (I-16), compound of formula I where R$^1$ is (phenylmethoxy)carbonyl, R$^2$ is hydrogen, R$^3$ is methyl and Z is oxygen A] (10E)-10,11-Didehydro-11-deoxy-6-O-methyl-erythromycin 2'-acetate 4"-(phenylmethyl carbonate) 12-[[(phenylmethoxy)carbonyl]acetate] (VIII-16)

To a solution of 200 mg (221 μmol) (10E)-10,11-didehydro-11-deoxy-6-O-methyl-erythromycin 2'-acetate 4"-(phenylmethyl carbonate) and 8.09 mg (66.2 μmol) DMAP in 10 ml dichloromethane kept under argon were added a solution of 343 mg (~50% purity; 883 μmol) monobenzyl malonate in 4 ml dichloromethane and a solution of 182 mg (883 μmol) DCC in 4 ml dichloromethane simultaneously over two days at room temperature. Following the addition, the reaction mixture was stirred at room temperature for further 12 hours. The solvent was partly evaporated under reduced pressure and the remaining suspension was filtrated. The filtrate was diluted with dichloromethane, washed with 3% aqueous NaHCO$_3$, dried over Na$_2$SO$_4$ and evaporated. The crude product was purified twice by flash chromatography on silica gel (CH$_2$Cl$_2$/MeOH/NH$_3$ 97:3:0.01→96:4:0.01) to give 190 mg of the desired product as a light yellow foam. MS (ISP): 1082.4 (MH$^+$). $^1$H-NMR (CDCl$_3$), diagnostic signals only: 0.81 (t, 3H), 0.91 (d, 3H), 1.82 (s, 3H), 2.00 (s, 3H), 2.23 (s, 6H), 2.40 (d, 1H), 3.14 (s, 3H), 3.32 (s3H), 3.36 (s, 2H), 4.68 (dd, 1H), 5.68 (dd, 1H), 6.59 (s, 1H), 7.25–7.41 (m, 10H).

B] (3R or S, 3aS, 4R or S, 6R, 8R, 9R, 10S, 11S, 12R, 15R, 15aS)-9-[[2-O-Acetyl-3,4,6-trideoxy-3-(dimethylamino)-β-D-xylo-hexopyranosyl]oxy]-11[[2,6-dideoxy-3-C-methyl-3-O-methyl-4-O-[(phenylmethoxy)carbonyl]-α-L-ribo-hexopyranosyl]oxy]-15-ethylhexadecahydro-8-methoxy-4,6,8,10,12,15a-hexamethyl-2,5,13-trioxo-2H-furo [2,3-c] oxacyclotetradecin-3-carboxylic acid phenylmethyl ester; mixture of diastereoisomers (IX-16)

To a solution of 56 mg (51.7 μmol) VIII-16 in 3 ml dry DMF kept under argon at 0° C. were added 65 μl of a solution of potassium t-butoxide (1M in THF). The reaction mixture was stirred at 0° C. for 1 hour. The reaction was subsequently quenched with 2 ml of a saturated NH$_4$Cl solution and partitioned between diethylether and 3% aqueous NaHCO$_3$. The organic layer was washed three times with 3% aqueous NaHCO$_3$, dried over Na$_2$SO$_4$ and evaporated. The crude product was submitted to a rough purification by flash chromatography on silica gel (CH$_2$Cl$_2$/MeOH/NH$_3$ 97:3:0.01→96:4:0.01) and directly used for the next reaction. MS (ISP): 1082.4 (MH$^+$).

C] (3R or S, 3aS, 4R or S, 6R, 8R, 9R, 10S, 11S, 12R, 15R, 15aS)-9-[[2-O-Acetyl-3,4,6-trideoxy-3-(dimethylamino)-β-D-xylo-hexopyranosyl]oxy]-15-ethylhexadecahydro-11-hydroxy-8-methoxy-4,6,8,10,12,15a-hexamethyl-2,5,13-trioxo-2H-furo [2,3-c] oxacyclotetradecin-3-carboxylic acid phenylmethyl ester; mixture of diastereoisomers (XI-16)

The product of example 16 step B was dissolved in 4 ml methanol containing 3% HCl. The reaction mixture was stirred at room temperature during 3.5 hours and subsequently the solvent was evaporated. The residue was dissolved in dichloromethane, washed with 3% aqueous NaHCO$_3$, dried over Na$_2$SO$_4$ and evaporated. The crude product was purified by flash chromatography on silica gel (CH$_2$Cl$_2$/MeOH/NH$_3$ 94:6:0.01→93:7:0.01) to give 15 mg of the desired product (mixture of diastereoisomers) as a foam. MS (ISP): 790.2 (MH$^+$).

D] (3R or S, 3aS, 4R or S, 6R, 8R, 9R, 10R, 12R, 15aS)-9-[[2-O-Acetyl-3,4,6-trideoxy-3-(dimethylamino)-β-D-xylo-hexopyranosyl]oxy]-15-ethylhexadecahydro-8-methoxy-4,6,8,10,12,15a-hexamethyl-2,5,11,13-tetraoxo-2H-furo [2,3-c] oxacyclotetradecin-3-carboxylic acid phenylmethyl ester; mixture of diastereoisomers (XII-16)

15 mg (19.0 μmol) XI-16, 24.4 mg (127.2 μmol) EDC*HCl and 24.3 μl (341.8 μmol) DMSO were dissolved in 1.5 ml dichloromethane and a solution of 24.6 mg (127.2 μmol) pyridinium trifluoroacetate in 0.5 ml dichloromethane was added over a period of 10 minutes. The reaction mixture was stirred at room temperature during two hours. The solution was diluted with dichloromethane, washed with 3% aqueous NaHCO$_3$, dried over Na$_2$SO$_4$ and evaporated. The crude product was purified by flash chromatography on silica gel (CH$_2$Cl$_2$/MeOH/NH$_3$ 96:4:0.01→94:6:0.01) to give 12 mg of the desired product (mixture of diastereoisomers) as a foam. MS (ISP): 788.3 (MH+).

E] (3R or S, 3aS, 4R or S, 6R, 8R, 9R, 10R, 12R, 15R, 15aS)-15-Ethylhexadecahydro-8-methoxy-4,6,8,10,12,15a-hexamethyl-2,5,11,13-tetraoxo-9-[[3,4,6-trideoxy-3-(dimethylamino)-β-D-xylo-hexopyranosyl]oxy]-2H-furo [2,3-c] oxacyclotetradecin-3-carboxylic acid phenylmethyl ester (I-16)

The product of step D (XII-16; 13 mg, 14.8 mmol) was dissolved in 4 ml methanol and stirred for 3 days at room temperature. The solvent was removed under reduced pressure and the crude product was purified by flash chromatography on silica gel ($CH_2Cl_2$/MeOH/$NH_3$ 95:5:0.01) to give 2.5 mg of the desired product as a colorless solid as a single diastereoisomer. $^1$H-NMR ($CDCl_3$), diagnostic signals only: 0.79 (t, 3H), 2.28 (s, 6H), 2.52 (s, 3H), 3.03–3.22 (m, 4H), 3.48–3.60 (m, 2H), 3.82 (q, 1H), 4.19 (d, 1H), 4.31 (d, 1H), 4.37 (d, 1H), 5.23 (s, 2H), 5.25 (dd, 1H), 7.27–7.44 (m, 5H).

EXAMPLE 17

Preparation of I-17, compound of formula I, where $R^1$ is [2-[4-(dimethylamino) phenyl]-2-oxoethyl]thio, $R^2$ is hydrogen, $R^3$ is methyl and Z is oxygen.

The title compound was prepared according to example 4 starting from XV-3 and α-bromo-4-diethylaminoacetophenone. MS (ISP): 833.3 (MH+). $^1$H-NMR ($CDCl_3$) diagnostic signals only: 0.89 (t, 3H), 1.14 (d, 3H), 1.18 (d, 3H), 1.22 (t, 6H), 1.25 (s, 3H), 1.31 (d, 3H), 1.37 (d, 3H), 1.51 (s, 3H), 1,55–1,80 (m, 3H), 1.95 (m, 1H), 2.31 (s, 6H), 2.62 (s, 1H), 2.64(s, 3H), 3.02 (q, 1H), 3.05–3.15 (m, 1H), 3.22 (m, 1H), 3.42 (q, 4H), 3.56 (m, 1H), 3.82 (q, 1H), 4.26 (d, 1H), 4.22 (d, 1H), 4.28 (d, 1H), 4.40 (s, 1H), 5.50 (dd, 1H), 6.61 (d, 2H), 7.78 (d, 2H).

EXAMPLE 18

Preparation of I-18 compound of formula I, where $R^1$ is [2-(1H-2,3-dihydroindol-1-yl)-2-oxoethyl]thio, $R^2$ is hydrogen, $R^3$ is methyl and Z is oxygen.

The title compound was prepared according to example 4 starting from XV-3 and 1-(bromoacetyl)-2,3-dihydro-1H-Indole. MS (ISP): 803.3 (MH+). $^1$H-NMR ($CDCl_3$) diagnostic signals only: 0.90 (t, 3H), 1.12 (d, 3H), 1.24 (d, 3H), 1.28 (s, 3H), 1.31 (d, 3H), 1.36 (d, 3H), 1.52 (s, 3H), 1,55–1,80 (m, 4H), 1.95 (m, 1H), 2.28 (s, 6H), 2.45–2.60 (m, 3H), 2.64 (s, 1H), 2.75 (s, 3H), 3.00–3.25 (m, 5H), 3.55 (m, 1H), 3.82 (q, 1H), 3.93 (q, 2H), 4.12–4.20 (m, 2H), 4.24 (d, 1H), 4.31 (d, 1H), 4.46 (s, 1H), 5.50 (dd, 1H), 6.99 (t, 1H), 7.17 (t, 2H), 8.22 (d, 1H).

EXAMPLE 19

Preparation of (3R or S, 3aR, 4R or S, 6R, 8R, 9R, 10R, 12R, 15R, 15aS) -15-Ethyloctahydro-8-methoxy-4,6,8,10,12,15a-hexamethyl-3-[[2-[(3-pyridinylcarbonyl)amino]ethyl] thio]-9-[[-3,4,6-trideoxy-3-(dimethylamino)-β-D-xylo-hexopyranosyl]oxy]-2H-furo [2,3-c] oxacyclotetradecin-2,5,11, 13 (3H,6H,12H)-tetrone (I-19) compound of formula I, where $R^1$ is [2-[(3-pyridinylcarbonyl)amino]ethyl]thio, $R^2$ is hydrogen, $R^3$ is methyl and Z is oxygen.

A] (10E)-10,11-didehydro-11-deoxy-6-O-methyl-erythromycin (V, scheme 1)

35.4 g (47.3 mmol) clarithromycin, 35.4 g (402.4 mmol) ethylene carbonate and 32.7 g (236.7 mmol) potassium carbonate dissolved in 200 ml dry DMF were heated to 110° C. until no starting material remained (~10 h). The mixture was then cooled to 50° C. and the solvent was evaporated in vacuo. The residue was taken up in 1000 ml diethylether. The organic layer was washed twice with 400 ml aqueous $NaHCO_3$ 3%, dried over $Na_2SO_4$ and concentrated under reduced pressure to a small volume from which the desired product precipitated. The filtrate was purified by flash chromatography on silica gel ($CH_2Cl_2$:MeOH:$NH_3$ 96:4:0.01). 25.2 g (73%) of the desired product V were obtained. MS (ISP): 730.4 (MH+). $^1$H-NMR ($CDCl_3$), diagnostic signals only: 0.90 (t, 3H), 1.10 (d, 3H), 1.16 (d, 3H), 1.21 (d, 2H), 1.24 (s, 3H), 1.24 (d, 3H), 1.29 (d, 3H), 1.40 (d, 3H), 1.41 (s, 3H), 1.55 (s, 3H), 2.01 (s, 3H), 2.27 (s, 6H), 2.34–2.46 (m, 2H), 2.83–2.93 (m, 1H), 3.01 (dd, 1H), 3.19 (dd, 1H), 3.23 (s, 3H), 3.31 (s, 3H), 3.38 (s, 3H), 3.42–3.51 (m, 1H), 3.67 (d, 1H), 3.96–4.07 (m, 2H), 4.36 (d, 1H), 4.85 (d, 1H), 5.01 (dd, 1H), 6.63 (s, 1H).

B] (10E)-10,11-didehydro-11-deoxy-6-O-methyl-erythromycin 2',4"-dibenzoate (VI-19), (scheme 1, formula VI)

To a solution of 16.9 g (23.2 mmol) (10E)-10,11-didehydro-11-deoxy-6-O-methyl-erythromycin (V) in 150 ml dry THF kept under argon were added 2.83 g (23.2 mmol) DMAP, 12.9 ml (92.7 mmol) triethylamine and 20.97 g (92.7 mmol) benzoic anhydride. The reaction was stirred at 35° C. for two days. Most of the solvent was evaporated and the residue was dissolved in 600 ml ethyl acetate. The organic layer was washed twice with 200 ml aqueous $NaHCO_3$ 5% and with 200 ml brine, dried over $Na_2SO_4$ and concentrated in vacuo. The crude product was purified by crystallisation from a small amount of ethyl acetate/hexane and the mother liquors were subsequently purified by flash chromatography on silica gel ($CH_2Cl_2$:MeOH:$NH_3$ 97:3:0.01→95:5:0.01) to give 15.4 g (71%) of the desired product VI-19. MS (ISP): 938.4 (MH+).

C] (10E)-10,11-didehydro-11-deoxy-6-O-methyl-erythromycin 2',4"-dibenzoate 12-(chloroacetate) (VII-19), (scheme 2, formula VII)

This compound was prepared from 8.6 g (9.17 mmol) of VI-19 according to the procedure described in example 1 step A. The crude product was purified by flash chromatography on silica gel ($CH_2Cl_2$:MeOH:$NH_3$ 98:2:0.01) to give 7.07 g (76%) of VII-19 as a foam. MS (ISP): 1014.5 (MH+).

D] (10E)-10,11-didehydro-11-deoxy-6-O-methyl-erythromycin 2',4"-dibenzoate 12-[[[2-[[(1,1-dimethylethoxy)carbonyl]amino]ethyl]thio]acetate] (VIII-19), (scheme 2, formula VIII)

To a solution of 5.8 g (5.7 mmol) VII-19 in 100 ml acetone were added 0.938 ml (6.28 mmol) DBU and a catalytic amount of sodium iodide. 1.115 g (6.29 mmol) 2(-tert-Butoxycarbonylamino)ethanethiol were added in one portion and the resulting suspension was stirred at room temperature for 1.5 hours. Most of the solvent was evaporated under reduced pressure and 150 ml dichloromethane were added to the residue. The organic layer was washed twice with 70 ml aqueous NaHCO3, dried over Na2SO4 and evaporated. The crude product was purified by flash chromatography on silica gel ($CH_2Cl_2$:MeOH:$NH_3$ 98:2:0.01) to give 5.68 g (86%) of VIII-19 as a foam. MS (ISP): 1155.5 (MH+).

E] (3R or S, 3aR, 4R or S, 6R, 8R, 9R, 10S, 11S, 12R, 15R, 15aS)-9-[[2-O-Benzoyl-3,4,6-trideoxy-3-(dimethylamino)-

β-D-xylo-hexopyranosyl]oxy]-11-[[4-O-benzoyl-2,6-dideoxy-3-C-methyl-3-O-methyl-α-L-ribo-hexopyranosyl]oxy]-15-ethyldecahydro-8-methoxy -4,6,8,10,12,15a-hexamethyl-3-[[2-[[(1,1-dimethylethoxy)carbonyl]amino]ethyl]thio]-2H-furo [2,3-c] oxacyclotetradecin-2,5,13 (3H, 6H)-trione; mixture of diastereomers; (IX-19), (scheme 2, formula IX)

To an ice cold solution of 2.0 g (1.73 mmol) VIII-19 in 20 ml dry DMF kept under argon were added 2.16 ml of a solution of KO′Bu (1M in THF). The reaction was stirred at 0° C. for 2 hours and then partitioned between 150 ml diethylether and 80 ml aqueous KH$_2$PO$_4$ (0.5 M). The organic layer was washed twice with 80 ml aqueous NaHCO$_3$3% and once with 80 ml brine, dried over Na$_2$SO$_4$ and evaporated under reduced pressure. The crude product (1.91 g) was used for the next step without further purification. MS (ISP): 1155.6 (MH$^+$).

F] (3R or S, 3aR, 4R or S, 6R, 8R, 9R, 10S, 11S, 12R, 15R, 15aS) -9-[[2-O-Benzoyl-3,4,6-trideoxy-3-(dimethylamino)-β-D-xylo-hexopyranosyl]oxy]-15-ethyldecahydro-11-hydroxy-8-methoxy-4,6,8,10,12,15a-hexamethyl-3-[[2-[[(1,1-dimethylethoxy)carbonyl]-amino]ethyl]thio]-2H-furo [2,3-c] oxacyclotetradecin-2,5,13 (3H,6H)-trione; mixture of diastereomers; (XI-19), (scheme 2, formula XI).

1.90 g (1.64 mmol) of IX-19 were dissolved in 100 ml methanol containing 3% HCl. The solution was kept at room temperature for 24 hours evaporated and dried under high vacuum. The crude hydrochloride salt was suspended in 20.0 ml THF and 12.0 ml N-ethyldiisopropylamine and 1.08 g (4.92 mmol) di-tert-butyl-dicarbonate were added. The reaction was stirred under argon at room temperature during two hours. Now 70 ml dichloromethane were added and the organic layer was washed with 50 ml of saturated aqueous NaHCO$_3$, 50 ml brine, dried over Na$_2$SO$_4$ and evaporated. The crude product was purified by flash chromatography on silica gel (CH$_2$Cl$_2$:MeOH:NH$_3$98:2:0.01) to give 1.06 g (72.2%) of XI-19 as a foam. MS (ISP): 893.2 (MH$^+$).

G] (3R or S, 3aR, 4R or S, 6R, 8R, 9R, 10R, 12R, 15R, 15aS)-9-[[2-O-Benzoyl-3,4,6-trideoxy-3-(dimethylamino)-β-D-xylo-hexopyranosyl]oxy]-15-ethyldecahydro-8-methoxy-4,6,8,10,12,15a-hexamethyl -3-[[2-[[(1,1-dimethylethoxy)carbonyl]-amino]ethyl]thio]-2H-furo [2,3-c] oxacyclotetradecin-2,5,13 (3H,6H, 12H)-tetrone; mixture of diastereomers; (XLIII-19), (scheme 11, formula XLIII).

This compound was prepared from 1.06 g (1.19 mmol) of XI-19 according to the procedure described in example 1 step E. The crude product was purified by flash chromatography on silica gel (CH$_2$Cl$_2$:MeOH:NH$_3$ 98:2:0.01) to give 0.87 g (82%) of XLIII-19 as a foam. MS (ISP): 891.4 (MH$^+$).

H] (3R or S, 3aR, 4R or S, 6R, 8R, 9R, 10R, 12R, 15R, 15aS)-3-[(2-aminoethyl)thio]-9-[[2-O-Benzoyl-3,4,6-trideoxy-3-(dimethylamino)-β-D-xylo-hexopyranosyl]oxy]-15-ethyloctahydro-8-methoxy-4,6,8,10,12,15a-hexamethyl-2H-furo [2,3-c] oxacyclo-tetradecin-2,5,11,13 (3H,6H, 12H)-tetrone (XLV-19) (scheme 11, formula XLV)

To a solution of 150 mg (0.168 mmol) XII-19 in 5 ml dichloromethane were added 1.0 ml trifluoroacetic acid. The reaction was stirred for 1 hour at room temperature. The mixture was diluted with 25 ml dichloromethane and the organic layer was washed once with 20 ml saturated aqueous NaHCO3, dried over Na2SO4 and evaporated. The crude product (112 mg) was used for the next step without further purification. MS (ISP): 791.2 (MH$^+$) 396.2 ([MH$_2$]$^{++}$).

I] (3R or S, 3aR, 4R or S, 6R, 8R, 9R, 10R, 12R, 15R, 15aS) -9-[[2-O-Benzoyl-3,4,6-trideoxy-3-(dimethylamino)-β-D-xylo-hexopyranosyl]oxy]-15-ethyloctahydro-8-methoxy-4,6,8,10,12,15a-hexamethyl-3-[[2-[(3-pyridinylcarbonyl)amino]ethyl]thio]-2H-furo [2,3-c] oxacyclotetradecin-2,5,11,13 (3H,6H,12H)-tetrone (XII-19) (scheme 11, formula XII)

To a solution of 112 mg (~0.14 mmol) crude XLV-19 in 15 ml dichloromethane kept under argon were added 58.2 μl (0.42 mmol) triethylamine and 27.4 mg (0.154 mmol) 3-pyridinecarbonyl chloride. The reaction mixture was stirred at room temperature until no starting material remained (~two hours). The organic layer was washed with 10 ml saturated aqueous NaHCO$_3$, dried over Na$_2$SO$_4$ and evaporated. The crude product was purified by flash chromatography on silica gel (CH$_2$Cl$_2$:MeOH:NH$_3$ 98:2:0.01) to give 100 mg (90%) of XII-19 as a foam. MS (ISP): 896.2 (MH$'$), 448.6 ([MH$_2$]$^{++}$).

K] (3R or S, 3aR, 4R or S, 6R, 8R, 9R, 10R, 12R, 15R, 15aS)-15-Ethyloctahydro-8-methoxy 4,6,8,10,12,15a-hexamethyl-3-[[2-[(3-pyridinylcarbonyl)amino]ethyl]thio]-9-[[-3,4,6 -trideoxy-3-(dimethylamino)-β-D-xylo-hexopyranosyl]oxy]-2H-furo [2,3-c] oxacyclo-tetradecin-2,5,11,13 (3H,6H,12H)-tetrone (I-19) (scheme 11, formula Ik)

100 mg (112 μmol) XII-19 were dissolved in 5 ml methanol and stirred for 3 days at room temperature under argon. The solvent was removed under reduced pressure. The crude product was purified by flash chromatography on silica gel (CH$_2$Cl$_2$:MeOH:NH$_3$ 95:5:0.01) to give 44 mg (50%) of I-19 as a single diastereoisomer. MS (ISP): 792.2 (MH$^+$). $^1$H-NMR (CDCl$_3$), diagnostic signals only: 0.87 (t, 3H), 1.11 (d, 3H), 1.14 (d, 3H), 1.23 (s, 3H), 1.26 (d, 3H), 1.31 (d, 3H), 1.34 (d, 3H), 1.64–1.80 (m, 3H), 1.87–1.99 (m) 1H), 2.27 (s, 6H), 2.41–2.50 (m, 1H), 2.55 (s, 3H), 2.56 (d, 1H), 2.57–2.65 (m, 1H), 2.91–3.01 (m, 1H), 3.03–3.12 (m, 2H), 3.17 (dd, 1H), 3.30–3.37 (m, 1H), 3.51–3.61 (m, 1H), 3.63–3.74 (m, 1H), 3.84 (q 1H), 4.10–4.19 (m, 1H), 4.23 (d, 1H), 4.28–4.33 (m, 2H), 5.31 (dd, 1H), 7.30–7.35 (m, 1H), 7.65–7.73 (s, br, 1H), 8.19–8.26 (m, 1H), 8.66–8.72 (m, 1H), 9.14–9.18 (m, 1H).

EXAMPLE 20

Preparation of I-20, compound of formula I, where R$^1$ is [2-[(2,1,3-benzoxadiazol-5-ylcarbonyl)amino]ethyl]thio, R$^2$ is hydrogen, R$^3$ is methyl and Z is oxygen.

The title compound was prepared following the procedure described in example 19 steps I–K starting from XLV-19 and 2,1,3-benzoxadiazole-5-carbonyl chloride. MS (ISP): (MH$^+$). $^1$H-NMR (CDCl$_3$), diagnostic signals only: 0.87 (t, 3H), 1.07 (s, 3H) 1,12 (d, 3H), 1.14 (d, 3H), 1.25 (d, 3H), 1.29 (d, 3H), 1.34 (d, 3H), 1.51 (d, 3H), 1.51 (s, 3H), 1.63–1.81 (m, 3H), 1.88–1.97 (m, 1H), 2.26 (s, 6H), 2.39–2.48 (m, 1H), 2.51 (s, 3H), 2.54–2.64 (m, 1H), 2.89–3.11 (m, 3H), 3.15 (dd, 1H), 3.33–3.57 m, 3H), 3.64–3.76 (m, 1H), 3.82 (q, 1H), 4.13–4.22 (m, 2H), 4.24–4.30 (m, 2H), 5.29 (dd, 1H), 7.83–7.91 (m, 2H), 7.94–7.99 (m, 1H), 8.50–8.52 (m, 1H).

EXAMPLE 21

Preparation of I-21, compound of formula I, where R$^1$ is [2-[[[5-(2-pyridinyl)thien-2-yl]sulfonyl]amino]ethyl]thio, R$^2$ is hydrogen, R$^3$ is methyl and Z is oxygen.

The title compound was prepared following the procedures described in example 19 steps I–K starting from XLV-19 and 5-(2-pyridinyl)-2-thiophensulfonyl chloride.

MS (ISP): (MH⁺). ¹H-NMR (CDCl₃), diagnostic signals only: 0.86 (t, 3H), 1.05 (d, 3H), 1.10 (d, 3H), 1.21 (d, 3H), 1.25(d, 3H), 1.31 (d, 3H), 1.34 (s, 3H), 1.37 (d, 3H), 1.47 (s, 3H), 2.27 (s, 6H), 2.41–2.51 (m, 1H), 2.55–2.64 (m, 1H), 2.76 (s, 3H), 2.78–2.87 (m, 1H), 2.98–3.25 (m, 4H), 3.45–3.61 (m, 4H), 3.83 (q, 1H), 4.15 (s, 1H), 4.26 (d, 1H), 4.32 (d, 1H), 5.21 (dd, 1H), 6.00–6.06 (m, br, 1H), 7.46–7.49 (m, 1H), 7.59–7.62 (m, 1H), 7.64–7.68 (m, 1H), 7.70–7.75 (m, 1H), 8.55–8.59 (m, 1H).

EXAMPLE 22

Preparation of I-22, compound of formula I, where $R^1$ is [2-[[(2,1,3-benzoxadiazol-4-yl)sulfonyl]amino]ethyl]thio, $R^2$ is hydrogen, $R^3$ is methyl and Z is oxygen.

The title compound was prepared following the procedures described in example 19 steps I-K starting from XLV-19 and 2,1,3-benzoxadiazole-5-sulfonyl chloride. MS (ISP): 867.3 (MH⁺). ¹H-NMR (CDCl₃), diagnostic signals only: 0.87 (t, 3H), 1.02 (d, 3H), 1.09 (d, 3H), 1.26 (d, 3H), 1.31 (d, 3H), 1.34 (s, 3H), 1.37 (d, 3H), 1.47 (s, 3H), 1.84–1.94 (m, 1H), 2.27 (s, 6H), 2.75 (s, 3H), 2.79–2.89 (m, 1H), 2.95–3.22 (m, 4H); 3.53–3.63 (m, 3H), 3.83 (q, 1H), 4.14 (s, 1H), 4.27 (d, 1H), 4.33 (d, 1H), 5.20 (dd, 1H), 6.13 (s, br, 1H), 7.49–7.57 (m, 1H), 8.03–8.10 (m, 2H).

EXAMPLE 23

Preparation of I-23 compound of formula I, where $R^1$ is [3-(4-cyanophenyl)prop-2-ynyl]thio, $R^2$ is hydrogen, $R^3$ is methyl and Z is oxygen.

A] (3R or S, 3aR, 4R or S, 6R, 8R, 9R, 10S, 11S, 12R, 15R, 15aS) -9-[[2-O-Acetyl-3,4,6-tri-deoxy-3-(dimethylamino)-β-D-xylo-hexopyranosyl]oxy]-15-ethyldecahydro-8-methoxy-4,6,8,10,12,15a-hexamethyl-3-[propyn-2-yl]thio-2H-furo [2,3-c] oxacyclotetradecin-2,5,11,13 (3H,6H,12H)-tetrone (XVII-23, X =CH₂C≡C, Q=H)

Compound XVII-23 was obtained according to example 4 starting from XV-3 and propargylbromide, but without deprotection with methanol. MS (ISP): 724.4 (MH⁺).

B] (3R or S, 3aR, 4R or S, 6R, 8R, 9R, 10S, 11S, 12R, 15R, 15aS) -9-[[2-O-Acetyl-3,4,6-tri-deoxy-3-(dimethylamino)-β-D-xylo-hexopyranosyl]oxy]-3-[(4-cyanophenyl)prop-2-ynyl-]thio-15-ethyldecahydro-8-methoxy-4,6,8,10,12,15a-hexamethyl-2H-furo [2,3-c] oxacyclotetradecin-2,5,11,13 (3H,6H,12H)-tetrone (XVIII-23)

A solution of 50 mg (69 μmol) XVII-23, in 1.5 ml acetonitrile and 0.04 ml triethylamine was treated with 1 mg copper (I) iodide, 3.0 mg bis(triphenylphosphine) palladium (II) dichloride and 16 mg 4-iodobenzonitrile for 24 h at room temperature under argon. The reaction mixture was diluted with 20 ml dichloromethane, washed with 20 ml 5% aqueous NaHCO3, 20 ml brine and evaporated. 55 mg (96%) of crude XVIII-23 were obtained and used directly for the next step. MS (ISP): 825.2 (MH⁺).

Deprotection of XVIII-23 was performed as described in example 1G to give product I-23 as a colourless solid as a single diasteomer. MS (ISP): 783.3 (MH⁺). ¹H-NMR (CDCl₃) diagnostic signals only: 0.87 (t, 3H), 1.14 (d, 3H), 1.16 (d, 3H), 1.22 (s, 3H), 1.31 (d, 3H), 1.38 (d, 3H), 1.52 (s, 3H), 1.55–1.80 (m, 4H), 1.95 (m, 1H), 2.58 (s broad, 6H), 2.65 (s, 1H), 2.78 (s, 3H), 3.00–3.25 (m, 2H), 3.45 (m, 1H), 3.66 (d, 1H), 3.84 (q, 1H), 4.03 (d, 1H), 4.12–4.20 (m, 2H), 4.26 (d, 1H), 4.39 (d, 1H), 4.59 (s, 1H), 5.45 (dd, 1H), 7.09 (d, 2H), 7.13 (d, 2H).

EXAMPLE 24

Preparation of I-24 compound of formula I, where $R^1$ is [2-[[(phenylmethyl) amino]sulfonyl]ethyl]thio, $R^2$ is hydrogen, $R^3$ is methyl and Z is oxygen.

The title compound was prepared according to example 4 starting from XV-3 and N-(phenylmethyl)-ethenesulfonamide. MS (ISP): 841.3 (MH⁺). ¹H-NMR (CDCl₃) diagnostic signals only: 0.86(t, 3H), 1.12 (d, 3H), 1.16 (d, 3H), 1.25 (s, 3H), 1.28 (d, 3H), 1.31 (d, 3H), 1.36 (d, 3H), 1.50 (s, 3H), 1.60–1.80 (m, 3H), 1.92 (m, 1H), 2.26 (s, 6H), 2.58 (s, 1H), 2.70 (s, 3H), 2.90–3.25 (m, 6H), 3.35–3.60 (m, 4H), 3.82 (q, 1H), 4.20–4.35 (m, 4H), 5.38 (dd, 1H), 7.20–7.40 (m, 5H).

EXAMPLE 25

Preparation of I-25 compound of formula I, where $R^1$ is [2-(8-quinolinylamino)-2-oxoethyl]thio, $R^2$ is fluoro, $R^3$ is methyl and Z is oxygen.

A] (3R or S, 3aR, 4R or S, 6R, 8R, 9R, 10R, 12S, 15R, 15aS)-9-[[2-O-Acetyl-3,4,6-trideoxy-3-(dimethylamino)-β-D-xylo-hexopyranosyl]oxy]-15-ethyl-12-fluoroctahydro-8-methoxy-4,6,8,10,12,15a-hexamethyl-3-[(3-nitro-2-pyridinyl)dithiol -2H-furo [2,3-c] oxacyclo-tetradecin-2,5,11,13 (3H,6H,12H)-tetrone; mixture of diastereomers (XV-25).

Compound XV-25 was prepared according to example 3, step A by treating compound XIV-1 with 3-nitro-2-pyridine-sulfenylchloride. MS (ISP): 858.1 (MH⁺). ¹H-NMR (CDCl₃) diagnostic signals only: 1.01 (t, 3H), 1.03 (d, 3H), 1.16 (d, 3H), 1.34 (s, 3H), 1.38 (d, 3H), 1.54 (s, 3H), 1.55–1.75 (m, 2H), 1.78 (d, 3H), 2.27 (s broad, 6H), 2.59 (s, 1H), 2.77 (s, 3H), 3.05–3.15 (m, 2H), 3.52 (m, 2H), 4.38 (d, 1H), 4.78 (m, 1H), 5.82 (dd, 0.6H), 5.92 (dd, 0.4H), 7.33 (dd, 1H), 8.52 (d, 1H), 8.85 (d, 1H).

The title compound was prepared according to example 4 starting from XV-25 and 2-bromo-N-8-quinolyl-acetamide. MS (ISP): 847.6 (MH⁺). ¹H-NMR (CDCl₃) diagnostic signals only: 0.93(t, 3H), 1.12 (d, 3H), 1.14 (d, 3H), 1.23 (s, 3H), 1.26 (d, 3H), 1.31 (d, 3H), 1.55 (s, 3H), 1.60–1.80 (m, 3H), 1.78 (d, 3H), 1.94 (m, 1H), 2.28 (s, 6H), 2.50 (s, 1H), 2.72 (s, 3H), 3.01 (q, 1H), 3.18 (m, 1H), 3.44–3.62 (m, 2H), 3.72 (d, 1H), 4.08 (d, 1H), 4.30 (d, 1H), 4.38 (s, 1H), 5.46 (dd, 1H), 7.40 (dd, 1H), 7.45–7.55 (m, 2H), 8.16 (dd, 1H), 8.75–8.85 (m, 2H), 10.56 (s. broad, 1H).

EXAMPLE 26

Preparation of compound of formula I-26, where $R^1$ is [2-(5-quinolinylamino)-2-oxoethyl]thio, $R^2$ is hydrogen, $R^3$ is methyl and Z is oxygen.

The title compound was prepared according to example 4 starting from XV-3 and 2-chloro-N-(quinolin-5-yl)acetamide. MS (ISP): 828.5 (MH⁺). ¹H-NMR (CDCl₃) diagnostic signals only: 0.91 (t, 3H), 1.05 (2d, 6H), 1.26 (s, 3H), 1.32 (d, 3H), 1.40 (d, 3H), 1.56(s, 3H), 1.50–1.80 (m, 3H), 1.96 (m, 1H), 2.26 (s, 6H), 2.61 (s, 1H), 2.81 (s, 3H), 3.00–3.20 (m, 3H), 3.58 (m, 1H), 3.63 (d, 1H), 3.84 (q, 1H), 4.09 (d, 1H), 4.12– 4.36 (m, 2H), 1H), 4.44 (s, 1H), 5.40 (dd, 1H), 7.40–7.50 (m, 1H), 7.71 (m, 1H), 7.90–8.10 (m, 2H), 8.42 (m, 1H), 8.95 (m, 1H), 9.50 (s, broad, 1H).

EXAMPLE 27

Preparation of (3R or S, 3aR, 4R or S, 6R, 8R, 9R, 10R, 12R, 15R, 15aS)-15-Ethyloctahydro-8-methoxy-4,6,8,10,12,15a- hexamethyl-3-[[2-[(3-quinolinylcarbonyl)amino]ethyl]thio]-9-[[3,4,6-trideoxy-3-(dimethylamino)-β-D-xylo-hexopyranosyl]oxy]-2H-furo [2,3-c] oxacyclotetradecin-2,5,11,13 (3H,6H,12H)-tetrone (I-27) compound of formula I, where $R^1$ is [2-[(3-quinolinylcarbonyl)amino]ethyl]thio, $R^2$ is hydrogen, $R^3$ is methyl and Z is oxygen.

A] (3R or S, 3aR, 4R or S, 6R, 8R, 9R, 10R, 12R, 15R, 15aS)-9-[[2-O-Benzoyl-3,4,6-trideoxy-3-(dimethylamino)-β-D-xylo-hexopyranosyl]oxy]-15-ethyloctahydro-8-methoxy-4,6,8,10,12,15a-hexamethyl-3-[[2-[(3-quinolinylcarbonyl)amino]ethyl]thio]-2H-furo [2,3-c] oxacyclotetradecin-2,5,11,13 (3H,6H,12H)-tetrone (XII-27) (scheme 11, formula XII)

To a solution of 21.9 mg (0.126 mmol) 3-quinolinecarboxylic acid, 69.1 mg (0.133 mmol) benzotriazol-1-yloxytripyrrolidinophosphonium hexafluorophosphate and 65 μl N-ethyldiisopropylamine in 5 ml dichloromethane were added after 10 minutes 100 mg (0.126 mmol) crude XLV-19. The reaction mixture was stirred under an atmosphere of argon at room temperature until no starting material remained (~6 hours). The organic layer was washed with 10 ml saturated aqueous $NaHCO_3$, dried over $Na_2SO_4$ and evaporated. The crude product was purified by flash chromatography on silica gel ($CH_2Cl_2$:MeOH:$NH_3$ 98:2:0.01) to give 97 mg (81%) of XII-27 as a foam.

B] (3R or S, 3aR, 4R or S, 6R, 8R, 9R, 10R, 12R, 15R, 15aS)-15-Ethyloctahydro-8-methoxy-4,6,8,10,12,15a-hexamethyl-3-[[2-[(3-quinolinylcarbonyl)amino]ethyl]thio]-9-[[3,4,6-trideoxy-3-(dimethylamino)-β-D-xylo-hexopyranosyl]oxy]-2H-furo [2,3-c] oxacyclo-tetradecin-2,5,11,13 (3H, 6H, 12H)-tetrone (I-27) (scheme 11, formula Ik)

97 mg (103 μmol) XII-27 were dissolved in 5 ml methanol and stirred for 3 days at room temperature under argon. The solvent was removed under reduced pressure. The crude product was purified by flash chromatography on silica gel ($CH_2Cl_2$:MeOH:$NH_3$ 98:2:0.01) to give 23 mg (27%) of I-27 as a single diastereoisomer. MS (ISP): 842.4 ($MH^+$). $^1$H-NMR ($CDCl_3$), diagnostic signals only: 0.86 (t, 3H), 1.03 (s, 3H), 1.09 (d, 3H), 1.12 (d, 3H), 1.22 (d, 3H), 1.27 (d, 3H), 1.32 (d, 3H), 1.49 (s, 3H), 2.32 (s, 6H), 2.40 (s, 3H), 2.45–2.61 (m, 3H), 2.98–3.10 (m, 2H), 3.12–3.21 (m, 2H), 3.32–3.40 (m, 1H), 3.48–3.58 (m, 1H), 3.68–3.85 (m, 3H), 4.12 (d, 1H), 4.13–4.22 (m, 1H), 4.26 (d, 1H), 4.31 (s, 1H), 5.31 (dd, 1H), 7.55–7.61 (m, 1H), 7.72–7.80 (m, 1H), 7.80–7.86 (m, br, 1H), 7.89–7.93 (m, 1H), 8.09–8.14 (m, 1H), 8.72 (m, 1H), 9.42 (m, 1H).

EXAMPLE 28

Preparation of I-28, compound of formula I, where $R^1$ is [2-[[[5-(dimethylamino)-1-naphthalenyl]sulfonyl]amino]ethyl]thio, $R^2$ is hydrogen, $R^3$ is methyl and Z is oxygen.

The title compound was prepared following the procedures described in example 19 steps I–K starting from XLV-19 and 5-(dimethylamino)-1-naphthalenylsulfonyl chloride. MS (ISP): 918.1 ($M-H^+$). $^1$H-NMR ($CDCl_3$), diagnostic signals only: 0.86 (t, 3H), 1.04 (d, 3H), 1.12 (d, 3H), 1.26 (d, 3H), 1.31 (d, 3H), 1.33 (s, 3H), 1.37 (d, 3H), 1.48 (s, 3H), 2.28 (s, 6H), 2.42–2.62 (m, 3H), 2.66–2.75 (m, 1H), 2.75 (s, 3H), 2.88 (s, 6H), 2.98–2.12 (m, 3H), 3.19 (dd, 1H), 3.31–3.39 (m, 1H), 3.82 (q, 1H), 4.29 (d, 1H), 4.27 (d, 1H), 4.33 (d, 1H), 5.21 (dd, 1H), 6.03 (br, 1H), 7.16 (d, 1H), 7.47–7.55 (m, 2H), 8.27 (d, 1H), 8.39 (d, 1H), 8.52 (d, 1H).

EXAMPLE 29

Preparation of I-29, compound of formula I, where $R^1$ is [2-[[(8-quinolinyl)sulfonyl]amino]ethyl]thio, $R^2$ is hydrogen, $R^3$ is methyl and Z is oxygen.

The title compound was prepared following the procedures described in example 19 steps I–K starting from XLV-19 and 8-quinolinesulfonyl chloride. MS (ISP): 876.3 ($M-H^+$). $^1$H-NMR ($CDCl_3$), diagnostic signals only: 0.85 (t, 3H), 1.00 (d, 3H), 1.09 (d, 3H), 1.26 (d, 3H), 1.29 (s, 3H), 1.31 (d, 3H), 1.37 (d, 3H), 1.45 (s, 3H), 1.62–1.78 (m, 3H), 1.79–1.90 (m, 1H), 2.26 (s, 6H), 2.41–2.57 (m, 3H), 2.70 (s, 3H), 2.73–2.89 (m, 1H), 2.90–3.01 (m, 2H), 3.04–3.13 (m,1H), 3.13–3.21 (m, 1H), 3.29–3.37 (m, 2H), 3.47 (s, br, 1H), 3.513.61 (m, 1H), 3.83 (q, 1H), 4.10 (s, 1H), 4.26 (d, 1H), 4.33 (d, 1H), 5.27 (dd, 1H), 6.71 (dd, br, 1H), 7.51–7.58 (m, 1H), 7.60–7.68 (m, 1H), 8.00–8.07 (m, 1H), 8.22–8.28 (m, 1H), 8.41–8.47 (m, 1H), 9.05–9.11 (m, 1H).

EXAMPLE 30

Preparation of I-30, compound of formula I, where $R^1$ is [2-[[(1,3-benzodioxol-5-yl)methyl]amino]-2-oxoethyl]thio, $R^2$ is hydrogen, $R^3$ is methyl and Z is oxygen.

The title compound was prepared following the procedure described in example 4 starting from XV-3 and N-(1,3-benzodioxol-5-ylmethyl-2-chloro-acetamide. MS (ISP): 835.32 ($MH^+$).

EXAMPLE 31

Preparation of I-31, compound of formula I, where $R^1$ is [2-[(2-furanylmethyl)amino]-2-oxoethyl]thio, $R^2$ is hydrogen, $R^3$ is methyl and Z is oxygen.

The title compound was prepared following the procedure described in example 4 starting from XV-3 and 2-chloro-N-(2-furanylmethyl)-acetamide. MS (ISP): 781.3 ($MH^+$).

EXAMPLE 32

Preparation of I-32, compound of formula I, where $R^1$ is [2-[(2-pyridinylmethyl)amino]-2-oxoethyl]thio, $R^2$ is hydrogen, $R^3$ is methyl and Z is oxygen.

The title compound was prepared following the procedure described in example 4 starting from XV-3 and 2-chloro-N-(2-pyridinylmethyl)-acetamide. MS (ISP): 882.36 ($MH^+$).

EXAMPLE 33

Preparation of I-33, compound of formula I, where $R^1$ is [2-[(5-methyl-3-isoxazolyl)amino]-2-oxoethyl]thio, $R^2$ is hydrogen, $R^3$ is methyl and Z is oxygen.

The title compound was prepared following the procedure described in example 4 starting from XV-3 and 2-chloro-N-(5-methyl-3-isoxazolyl)-acetamide. MS (ISP): 782.3 ($MH^+$).

EXAMPLE 34

Preparation of I-34, compound of formula I, where $R^1$ is [2-[(2-benzothiazolylmethyl)amino]-2-oxoethyl]thio, $R^2$ is hydrogen, $R^3$ is methyl and Z is oxygen.

The title compound was prepared following the procedure described in example 4 starting from XV-3 and N-(2-benzothiazolylmethyl)-2-chloro-acetamide. MS (ISP): 848.3 ($MH^+$).

EXAMPLE 35

Preparation of I-35, compound of formula I, where $R^1$ is [2-[(1H-imidazol-2-ylmethyl)amino]-2-oxoethyl]thio, $R^2$ is hydrogen, $R^3$ is methyl and Z is oxygen.

The title compound was prepared following the procedure described in example 4 starting from XV-3 and 2-chloro-N-(1H-imidazol-2-ylmethyl)-acetamide. MS (ISP): 781.3 (MH$^+$).

EXAMPLE 36

Preparation of compound of formula I-36, where $R^1$ is [3-(5-quinolinylamino)-3-oxopropyl]thio, $R^2$ is hydrogen, $R^3$ is methyl and Z is oxygen.

The title compound was prepared according to example 4 starting from XV-3 and N-5-quinolinyl-2-propenamide. MS (ISP): 842.2 (MH$^+$). $^1$H-NMR (CDCl$_3$) diagnostic signals only: 0.84 (t, 3H), 1.10 (1d, 3H), 1.19 (s, 3H), 1.21 (s, 3H), 1.26 (d, 3H), 1.31 (d, 3H), 1.51 (s, 3H), 1.96 (m, 1H), 2.23 (s, 6H), 2.27 (s, 3H), 2.58 (s, 1H), 2.90–3.25 (m, 7H), 3.40–3.60 (m, 3H), 3.79 (q, 1H), 4.02 (d, 1H), 4.22 (d, 1H), 1H), 4.35(s, 1H), 5.27 (dd, 1H), 7.42 (dd, 1H), 7.69 (t, 1H), 7.90 (d, 1H), 8.05 (d, 1H), 8.53 (d, 1H), 8.90 (s broad, 1H).

EXAMPLE 37

Preparation of I-37 compound of formula I, where $R^1$ is [2-(2-quinolinylamino)-2-oxoethyl]thio, $R^2$ is hydrogen, $R^3$ is methyl and Z is oxygen.

The title compound was prepared according to example 4 starting from XV-3 and 2-chloro-N-2-quinolinyl-acetamide. MS (ISP): 828.4 (MH$^+$). $^1$H-NMR (CDCl$_3$) diagnostic signals only: 0.95 (t, 3H), 1.11 (d, 3H), 1.27 (d, 3H), 1.35 (d, 3H), 1.41 (s, 3H), 1.43 (s, 3H), 1.53 (s, 3H), 1.50–1.80 (m, 3H), 1.94 (m, 1H), 2.27 (s, 6H), 2.40–2.60 (m, 2H), 2.71 (s, 1H), 2.92 (s, 3H), 3.00–3.25 (m, 4H), 3.50–3.60 (m, 2H), 3.62 (d, 1H), 3.85 (q, 1H), 4.02 (d, 1H), 4.28 (d, 1H), 4.34 (d, 1H), 4.43 (s, 1H), 5.43 (dd, 1H), 7.41 (t, 1H), 7.61 (t, 1H), 7.76 (d, 1H), 7.82 (d, 1H), 8.16 (d, 1H), 8.45 (d, 1H), 9.41 (s broad, 1H).

EXAMPLE 38

Preparation of I-38 compound of formula I, where $R^1$ is [2-(6-quinolinylamino)-2-oxoethyl]thio, $R^2$ is hydrogen, $R^3$ is methyl and Z is oxygen.

The title compound was prepared according to example 4 starting from XV-3 and 2-chloro-N-6-quinolinyl-acetamide. MS (ISP): 828.4 (MH$^+$). $^1$H-NMR (CDCl$_3$) diagnostic signals only: 0.89 (t, 3H), 1.12 (d, 3H), 1.17 (d, 3H), 1.31 (d, 3H), 1.35 (s, 3H), 1.52 (s, 3H), 1.50–1.80 (m),33H), 1.96 (m, 1H), 2.26 (s, 6H), 2.40–2.70 (m, 2H), 2.62 (s, 1H), 2.83 (s, 3H), 3.05–3.25 (m, 4H), 3.50–3.60 (m, 2H), 3.58 (d, 1H), 3.87 (q, 1H), 4.14 (d, 1H), 4.15 (d, 1H), 4.29 (d, 1H), 4.30–4.40 (m, 2H), 5.33 (dd, 1H), 7.38 (dd, 1H), 7.99 (dd, 1H), 8.05 (d, 1H), 8.13 (d, 1H), 8.61 (m, 1H), 8.83 (m, 1H), 9.54 (s broad, 1H).

EXAMPLE 39

Preparation of I-39 compound of formula I, where $R^1$ is [2-(3-quinolinylamino)-2-oxoethyl]thio, $R^2$ is hydrogen, $R^3$ is methyl and Z is oxygen.

The title compound was prepared according to example 4 starting from XV-3 and 2-chloro-N-3-quinolinyl-acetamide. MS (ISP): 828.4 (MH$^+$). $^1$H-NMR (CDCl$_3$) diagnostic signals only: 0.92 (t, 3H), 1.12 (d, 3H), 1.16 (d, 3H), 1.28 (d, 3H), 1.34 (d, 3H), 1.42 (s, 3H), 1.53 (s, 1H), 1.50–1.80 (m, 3H), 1.95 (m, 1H), 2.26 (s, 6H), 2.40–2.50 (m, 1H), 2.58 (s, 1H), 2.65–2.75 (m, 1H), 2.85 (s, 3H), 3.05–3.25 (m, 3H), 3.50–3.60 (m, 1H), 3.54 (d, 1H), 3.86 (q, 1H), 4.26 (d, 1H), 4.30–4.45 (m, 3H), 5.30 (dd, 1H), 7.52 (m, 1H), 7.62(m, 1H), 7.82 (d, 1H), 8.05 (d, 1H), 9.01 (m, 1H), 9.18 (m, 1H), 9.69 (s broad, 1H).

EXAMPLE 40

Preparation of I-40 compound of formula I, where $R^1$ is [2-(5-isoquinolinylamino)-2-oxoethyl]thio, $R^2$ is hydrogen, $R^3$ is methyl and Z is oxygen.

The title compound was prepared according to example 4 starting from XV-3 and 2-chloro-N-5-isoquinolinyl-acetamide. MS (ISP): 828.4 (MH$^+$). $^1$H-NMR (CDCl$_3$) diagnostic signals only: 0.91 (t, 3H), 1.10 (d, 3H), 1.12 (d, 3H), 1.28 (d, 3H), 1.31 (s, 3H), 1.41 (s, 3H), 1.53 (s, 1H), 1.50–1.80 (m, 3H), 1.94 (m, 1H), 2.26 (s, 6H), 2.40–2.50 (m, 2H), 2.62 (s, 1H), 2.83 (s, 3H), 3.05–3.20 (m, 3H), 3.45–3.60 (m, 1H), 3.63 (d, 1H), 3.87 (q, 1H), 4.20 (d, 1H), 4.28 (d, 1H), 4.31 (d, 1H), 4.46 (s, 1H), 5.42 (dd, 1H), 7.63 (t, 1H), 7.82(d, 1H), 7.90 (d, 1H), 8.32 (d, 1H), 8.55 (d, 1H), 9.26 (s, 1H), 9.54 (s broad, 1H).

EXAMPLE 41

Preparation of I-41 compound of formula I, where $R^1$ is [3-(6-quinolinylamino)-3-oxopropyl]thio, $R^2$ is hydrogen, $R^3$ is methyl and Z is oxygen.

The title compound was prepared according to example 4 starting from XV-3 and N-6-quinolinyl-2-propenamide. MS (ISP): 842.3 (MH$^+$). $^1$H-NMR (CDCl$_3$) diagnostic signals only: 0.85 (t, 3H), 1.01 (s, 3H), 1.18 (d, 3H), 1.21 (d, 3H), 1.31 (s, 3H), 1.51 (s, 3H), 1.50–1.80 (m, 3H), 1.91 (m, 1H), 2.24 (s, 6H), 2.39 (s, 3H), 2.40–2.50 (m, 2H), 2.62 (s, 1H), 2.90–3.20 (m, 6H), 3.40–3.55 (m, 3H), 3.82 (q, 1H), 4.12 (d, 1H), 4.26 (d, 1H), 4.35 (s, 1H), 5.32 (dd, 1H), 7.33 (dd, 1H), 7.72(dd, 1H), 8.00 (d, 1H), 8.11 (d, 1H), 8.51 (m, 1H), 8.77 (s broad, 1H), 9.54 (m, 1H).

EXAMPLE 42

Preparation of I-42 compound of formula I, where $R^1$ is [3-(3-quinolinylamino)-3-oxopropyl]thio, $R^2$ is hydrogen, $R^3$ is methyl and Z is oxygen.

A] N-3-quinolinyl-2-propenamide 0.39g (3.81 mmol) triethylamine were added to a suspension of 0.5 g (3.47 mmol) 3-aminoquinoline in 5 ml acetone. 0.35 g (3.81 mmol) acrylic acid chloride were added dropwise to the suspension at 0° C. The yellow suspension was stirred at 0° C. for 1 h. The reaction mixture was diluted with 25 ml 3% NaHCO$_3$ and extracted twice with 25 ml ethyl acetate. The combined organic phases were washed with 25 ml water, 25 ml brine, dried over MgSO4 and the solvent was removed under reduced pressure. The crystalline material was triturated with 10 ml ethylacetate. 0.354 g (51.5%) of a beige product were isolated by filtration and dried at room temperature in vacuo. MS (ISP): 199.3 (MH$^+$). $^1$H-NMR (CDCl$_3$): 5.85 (dd, 1H), 6.34 (dd, 1H), 6.55 (dd, 1H), 7.56–7.70 (m, 2H), 7.90 (m, 2H), 8.79 (m, 1H), 8.95 (m, 1H).

B] The title compound was prepared according to example 4 starting from XV-3 and N-3-quinolinyl-2-propenamide. MS (ISP): 842.3 (MH$^+$). $^1$H-NMR (CDCl$_3$) diagnostic signals only: 0.85 (t, 3H), 0.90 (s, 3H), 1.14 (d, 3H), 1.21 (d, 3H), 1.25 (d, 3H), 1.29 (d, 3H), 1.31 (d, 3H), 1.55 (s, 3H), 1.50–1.80 (m, 3H), 1.92 (m, 1H), 2.24 (s, 6H), 2.33 (s, 3H), 2.62 (s, 1H), 2.85–3.20 (m, 6H), 3.40–3.55 (m, 3H), 3.81 (q, 1H), 4.09 (d, 1H), 4.23 (d, 1H), 4.38 (s, 1H), 5.32 (dd, 1H), 7.48 (dd, 1H), 7.57(dd, 1H), 7.78 (d, 1H), 7.98 (d, 1H), 8.88 (m, 1H), 8.91 (s broad, 1H).

EXAMPLE 43

Preparation of (3R or S, 3aR, 4R or S, 6R, 8R, 9R, 10R, 12R, 15R, 15aS) -15-Ethyloctahydro-8-methoxy-4,6,8,10,12,15a-hexamethyl-3-[[2-[(3-pyridinylcarbonyl)amino]ethyl] sulfonyl]-9-[[-3,4,6-trideoxy-3-(dimethylamino)-β-D-xylo-hexopyranosyl]oxy]-2H-furo [2,3-c] oxacyclotetradecin-2,5,11,13 (3H,6H,12H)-tetrone (I-43) compound of formula I, where R$^1$ is [2-[(3-pyridinylcarbonyl)amino]ethyl]sulfonyl, R$^2$ is hydrogen, R$^3$ is methyl and Z is oxygen.

A] (3R or S, 3aR, 4R or S, 6R, 8R, 9R; 10R, 12R, 15R, 15aS)-9-[[2-O-Benzoyl-3,4,6-trideoxy-3-(dimethylamino)-β-D-xylo-hexopyranosyl]oxy]-15-ethyldecahydro-8-methoxy-4,6,8,10,12,15a-hexamethyl -3-[[2-[[(1,1-dimethylethoxy) carbonyl]amino]ethyl]sulfonyl]-2H-furo [2,3-c] oxacyclotetradecin-2,5,13 (3H,6H, 12H)-tetrone; mixture of diastereomers; (XLIV-43), (scheme 11, formula XLIV).

To a solution of 150 mg (0.168 mmol) XLIII-19 in 5 ml dichloromethane at 0° C. were added 247 mg (2.94 mmol) sodium bicarbonate and 363 mg (1.47 mmol) m-chloroperbenzoic acid. The mixture was allowed to warm to room temperature and stirred for 4 days. 5 ml of an aqueous sodium pyrosulfite solution were added and the mixture was stirred vigorously for 1 hour. The pH of the solution was adjusted to pH 9 with saturated aqueous sodium carbonate and extracted twice with 10 ml dichloromethane. The combined organic layers were washed with 10 ml aqueous NaHCO$_3$ 3%, 10 ml brine, dried over Na$_2$SO$_4$ and evaporated to give 148 mg of a light yellow solid. MS (ISP): 923.3 (MH$^+$).

B] (3R or S, 3aR, 4R or S, 6R, 8R, 9R, 10R, 12R, 15R, 15aS)-3-[(2-aminoethyl)sulfonyl]-9-[[2-O-Benzoyl-3,4,6-trideoxy-3-(dimethylamino)-β-D-xylo-hexopyranosyl]oxy]-15-ethyloctahydro-8-methoxy-4,6,8,10,12,15a-hexamethyl-2H-furo [2,3-c] oxacyclo-tetradecin-2,5,11,13 (3H,6H, 12H)-tetrone (XLV-43) (scheme 11, formula XLV, p=2)

This compound was prepared following the procedure described in example 19 step H starting from XLIV-43. MS (ISP): 823.2 (MH$^+$) 412.5 ([MH$_2$]$^{++}$).

C] (3R or S, 3aR, 4R or S, 6R, 8R, 9R, 10R, 12R, 15R, 15aS)-9-[[2-O-Benzoyl-3,4,6-trideoxy-3-(dimethylamino)-β-D-xylo-hexopyranosyl]oxy]-15-ethyloctahydro-8-methoxy-4,6,8,10,12,15a-hexamethyl-3-[[2-[(3-pyridinylcarbonyl)amino]ethyl]sulfonyl]-2H-furo [2,3-c] oxacyclotetradecin-2,5,11,13 (3H,6H,12H)-tetrone (XII-43) (scheme 11, formula XII)

This compound was prepared following the procedure described in example 19 step I starting from XLV-43 and 3-pyridinecarbonyl chloride. MS (ISP): 928.3 (MH$^+$).

D] (3R or S, 3aR, 4R or S, 6R, 8R, 9R, 10R, 12R, 15R, 15aS)-15-Ethyloctahydro-8-methoxy-4,6,8,10,12,15a-hexamethyl-3-[[2-[(3-pyridinylcarbonyl)amino]ethyl]sulfonyl]-9-[[-3,4,6-trideoxy-3-(dimethylamino)-β-D-xylo-hexopyranosyl]oxy]-2H-furo [2,3-c] oxacyclotetradecin-2,5,11,13 (3H,6H, 12H)-tetrone (I-43) (scheme 11, formula Ik).

This compound was prepared following the procedure described in example 19 step K. MS (ISP): 824.5 (MH$^+$). $^1$H-NMR (CDCl$_3$), diagnostic signals only: 0.87 (t, 3H), 0.92 (d, 3H), 1.08 (d, 3H), 2.30 (s, 6H), 2.80 (s, 3H), 3.29 (s, 1H), 3.87 (q, 1H), 4.36 (d, 1H), 4.37 (d, 1H), 4.93 (s, 1H), 5.62 (dd, 1H), 7.30–7.37 (m, 1H), 7.65 (dd, br, 1H), 8.11–8.18 (m, 1H), 8.68–8.73 (m, 1H), 9.00–9.06 (m, 1H)

EXAMPLE 44

Preparation of I-44, compound of formula I, where R$^1$ is [2-[(2,1,3-benzoxadiazol-5-ylcarbonyl)amino]ethyl]sulfonyl, R$^2$ is hydrogen, R$^3$ is methyl and Z is oxygen.

The title compound was prepared following the procedure described in example 43 steps B–D starting from XLV-43 and 2,1,3-benzoxadiazole-5-carbonyl chloride. MS (ISP): 865.5 (MH$^+$). $^1$H-NMR (CDCl$_3$), diagnostic signals only: 0.88 (t, 3H), 0.99 (d, 3H), 1.07 (d, 3H), 1.27 (d, 3H), 1.30 (s, 3H), 1.34 (d, 3H), 1.37 (d, 3H), 1.60 (s, 3H), 2.27 (s, 6H), 2.81 (s, 3H), 3.87 (q, 1H), 4.35 (d, 1H), 4.37 (d, 1H), 4.97 (s, 1H), 5.62 (dd, 1H), 7.80 (dd, br, 1H), 7.84–7.94 (m, 2H), 8.36 (s, 1H).

EXAMPLE 45

Preparation of I-45, compound of formula I, where R$^1$ is [2-[2,4-dimethoxyphenyl]-2-oxoethyl]thio, R$^2$ is hydrogen, R$^3$ is methyl and Z is oxygen.

The title compound was prepared following the procedure described in example 4 starting from XV-3 and 2-bromo-1-(2,4-dimethoxyphenyl)-ethanone. MS (ISP): 822.38 (MH$^+$).

EXAMPLE 46

Preparation of (3R or S, 3aR, 4R or S, 6R, 8R, 9R, 10R, 12R, 15R, 15aS) -3-[[2-[(5-Cyanopyridin-2-yl)amino]ethyl]thio]-15-ethyloctahydro-8-methoxy-4,6,8,10,12,15a-hexamethyl-9-[[-3,4,6-trideoxy-3-(dimethylamino)-β-D-xylo-hexopyranosyl]oxy]-2H-furo [2,3-c] oxacyclotetradecin-2,5,11,13 (3H,6H,12H)-tetrone (I-46) compound of formula I, where R$^1$ is [2-[(5-cyanopyridin-2-yl)amino]ethyl]thio, R$^2$ is hydrogen, R$^3$ is methyl and Z is oxygen.

A] (3R or S, 3aR, 4R or S, 6R, 8R, 9R, 10R, 12R, 15R, 15aS)-9-[[2-O-Benzoyl-3,4,6-trideoxy-3-(dimethylamino)-β-D-xylo-hexopyranosyl]oxy]-3-[[2-[(5-Cyanopyridin-2-yl)amino]ethyl]thio]-15-ethyloctahydro-8-methoxy-4,6,8,10,12,15a-hexamethyl 2H-furo [2,3-c] oxacyclotetradecin-2,5,11,13 (3H,6H,12H)-tetrone (XII-46).

To a solution of 130mg (~0.16 mmol) crude XLV-19 and 75 μl (0.54 mmol) triethylamine in 20 ml acetonitrile were added 33.8 mg (0.25 mmol) 6-chloro-3-pyridinecarbonitrile. The reaction mixture was heated to reflux during 36 hours. 50 ml ethyl acetate were added and the organic layer was washed with 10 ml saturated aqueous NaHCO$_3$, dried over Na$_2$SO$_4$ and evaporated. The crude product was purified by flash chromatography on silica gel (CH$_2$Cl$_2$:MeOH:NH$_3$ 98:2:0.01) to give 81 mg (55%) of XII-46 as a foam. $^1$H-NMR (CDCl$_3$), diagnostic signals only: 0.83 (t, 3H), 2.26 (s, 6H), 2.72 (s, 3H), 3.71 (q, 1H), 4.56 (d, 1H), 5.04 (dd, 1H), 5.29 (dd, 1H), 6.20 (s, br, 1H), 6.50 (d, 1H), 7.39–7.61 (m, 4H), 7.99–8.07 (m, 2H), 8.35 (d, 1H).

B] (3R or S, 3aR, 4R or S, 6R, 8R, 9R, 10R, 12R, 15R, 15aS)-3-[[2-[(5-Cyanopyridin-2-yl)amino]ethyl]thio]-15- ethyloctahydro-8-methoxy-4,6,8,10,12,15a-hexamethyl-9-[[-3,4,6-trideoxy-3-(dimethylamino)-β-D-xylo-hexopyranosyl]oxy]-2H-furo [2,3-c] oxacyclotetradecin-2,5,11,13 (3H, 6H,12H)-tetrone (I-46).

The product of step A (23 mg, 0.027 mmol) was dissolved in 5 ml methanol and stirred for 4 days at room temperature. The solvent was removed under reduced pressure and the product was purified by flash chromatography on silica gel ($CH_2Cl_2$:MeOH:$NH_3$ 98:2:0.01) to give 44 mg (62%) of I-46 as a single diastereoisomer. MS (ISP): 789.5 (MH$^+$). $^1$H-NMR (CDCl$_3$), diagnostic signals only: 0.87 (t, 3H), 1.10 (d, 3H), 1.15 (d, 3H), 1.26 (d, 3H), 1.32 (d, 3H), 1.33 (s, 3H), 1.36 (d, 3H), 1.50 (s, 3H), 1.64–1.84 (m, 3H), 1.86–1.98 (m, 1H), 2.26 (s, 6H), 2.41–2.51 (m, 1H), 2.54–2.64 (m, 2H), 2.74 (s, 3H), 2.92–3.02 (m, 1H), 3.02–3.13 (m, 2H), 3.18 (dd, 1H), 3.22–3.31 (m, 1H), 3.48 (s, br, 1H), 3.52–3.61 (m, 2H), 3.47–3.91 (m, 3H), 4.24–4.30 (m, 2H), 4.33 (d, 1H), 5.31 (dd, 1H), 6.22 (s, br, 1H), 6.51 (d, 1H), 7.50 (dd, 1H), 8.36 (d, 1H).

EXAMPLE 47

Preparation of I-47, compound of formula I, where R$^1$ is [2-[(6-quinolinylcarbonyl)amino]ethyl]thio, R$^2$ is hydrogen, R$^3$ is methyl and Z is oxygen.

The title compound was prepared following the procedures described in example 27 steps A–B starting from XLV-19 and 6-quinolinecarboxylic acid. MS (ISP): 842.5 (MH$^+$). $^1$H-NMR (CDCl$_3$), diagnostic signals only: 0.86 (t, 3H), 2.35 (s, 6H), 2.49 (s, 3H), 2.50–2.60 (m, 2H), 2.54 (s, 1H), 3.82 (q, 1H), 4.12–4.22 (m, 2H), 4.28 (d, 1H), 4.33 (s, 1H), 5.33 (dd, 1H), 7.41–7.48 (m, 1H), 7.69 (dd, br, 1H), 8.09–8.29 (m, 3H), 8.45 (s, 1H), 8.93–8.99 (m, 1H).

EXAMPLE 48

Preparation of I-48, compound of formula I, where R$^1$ is [2-[[[6-(1H-imidazol-1-yl)-3-pyridinyl]carbonyl]amino]ethyl]thio, R$^2$ is hydrogen, R$^3$ is methyl and Z is oxygen.

The title compound was prepared following the procedures described in example 27 steps A–B starting from XLV-19 and 6-(1H-imidazol-1-yl)-3-pyridinecarboxylic acid. MS (ISP): 858.6 (MH$^+$).

EXAMPLE 49

Preparation of I-49, compound of formula I, where R$^1$ is [2-[(8-quinolinylcarbonyl)amino]ethyl]thio, R$^2$ is hydrogen, R$^3$ is methyl and Z is oxygen.

The title compound was prepared following the procedures described in example 27 steps A–B starting from XLV-19 and 8-quinolinecarboxylic acid. MS (ISP): 842.5 (MH$^+$). $^1$H-NMR (CDCl$_3$), diagnostic signals only: 0.86 (t, 3H), 2.27 (s, 6H), 2.41–2.51 (m, 1H), 2.51–2.61 (m, 1H), 2.66 (s, 1H), 2.68 (s, 3H), 3.00–3.21 (m, 4H), 3.27–3.36 (m, 1H), 3.50–3.60 (m, 1H), 3.84 (q, 1H), 3.89–4.06 (m, 2H), 4.23 (d, 1H), 4.32 (d, 1H), 4.37 (s, 1H), 5.49 (dd, 1H), 7.43–7.50 (m, 1H), 7.62–7.70 (m, 1H), 7.93 (d, 1H), 8.25 (dd, 1H), 8.84 (dd, 1H), 9.02 (dd, 1H), 11.51 (dd, br, 1H).

EXAMPLE 50

Preparation of I-50, compound of formula I, where R$^1$ is [2-[[[6-(1H-pyrazol-1-yl)-3-pyridinyl]carbonyl]amino]ethyl]thio, R$^2$ is hydrogen, R$^3$ is methyl and Z is oxygen.

The title compound was prepared following the procedures described in example 27 steps A–B starting from XLV-19 and 6-(1H-pyrazol-1-yl)-3-pyridinecarboxylic acid. MS (ISP): 858.6 (MH$^+$). $^1$H-NMR (CDCl$_3$), diagnostic signals only: 0.88 (t, 3H), 2.29 (s, 6H), 2.44–2.54 (m, 1H), 2.55 (s, 1H), 2.56 (s, 3H), 2.60–2.69 (m, 1H), 2.88–2.98 (m, 1H), 3.04–3.13 (m, 2H), 3.19 (dd, 1H), 3.33–3.39 (m, 1H), 3.49–3.58 (m, 1H), 3.59–3.70 (m, 1H), 3.84 (q, 1H), 4.16–4.27 (m, 2H), 4.28–4.34 (m, 2H), 5.32 (dd, 1H), 6.44 (s, 1H), 7.73 (s, 1H), 7.77 (s, br, 1H), 8.02 (d, 1H), 8.38 (dd, 1H), 8.57 (d, 1H), 9.03 (d, 1H).

EXAMPLE 51

Preparation of I-51, compound of formula I, where R$^1$ is [2-[(1H-purin-6-yl)amino]ethyl]thio, R$^2$ is hydrogen, R$^3$ is methyl and Z is oxygen.

The title compound was prepared following the procedures described in example 46 steps A–B starting from XLV-19 and 6-chloro-1H-purine. MS (ISP): 805.6 (MH$^+$). $^1$H-NMR (CDCl$_3$), diagnostic signals only: 0.87 (t, 3H), 2.27 (s, 6H), 2.42–2.52 (m, 1H), 2.59–2.69 (m, 2H), 2.77 (s, br, 3H), 3.02–3.16 (m, 3H), 3.19 (dd, 1H), 3.31–3.41 (m, 1H), 3.51–3.62 (m, 1H), 3.84 (q, 1H), 3.90–4.04 (m, br, 1H), 4.15–4.26 (m, br, 1H), 4.27 (d, 1H), 4.33 (d, 1H), 4.39 (s, br, 1H), 5.37 (dd, 1H), 6.67 (s, br, 1H), 7.89 (s, br, 1H), 8.40 (s, br, 1H).

EXAMPLE 52

Preparation of I-52, compound of formula I, where R$^1$ is [2-[(6-bromo-2-methyl-quinazolin-4-yl)amino]ethyl]thio, R$^2$ is hydrogen, R$^3$ is methyl and Z is oxygen.

The title compound was prepared following the procedures described in example 46 steps A–B starting from XLV-19 and 7-bromo-4-chloro-2-methyl-quinazoline (WO0220488) with the only difference that the reaction was run at room temperature. MS (ISP): 909.5 (MH$^+$). $^1$H-NMR (CDCl$_3$), diagnostic signals only: 0.86 (t, 3H), 2.26 (s, 6H), 2.41–2.50 (m, 1H), 2.58 (s, 3H), 2.59 (s, 3H), 2.61–2.68 (m, 1H), 3.05–3.15 (m, 2H), 3.19 (dd, 1H)3.34–3.42 (m, 1H), 3.44–3.52 (s, br, 1H), 3.52–3.62 (m, 1H), 3.78–3.89 (m, 2H), 4.25 (d, 1H), 4.33 (d, 1H), 4.34–4.44 (m, 2H), 5.33 (dd, 1H), 7.11 (dd, br, 1H), 7.38–7.44 (m, 1H), 7.88–7.96 (m, 2H).

EXAMPLE 53

Preparation of I-53, compound of formula I, where R$^1$ is [2-[[2'-methoxy-(1,1'-biphenyl)-2-yl]amino]-2-oxoethyl]thio, R$^2$ is hydrogen, R$^3$ is methyl and Z is oxygen.

The title compound was prepared following the procedure described in example 4 starting from XV-3 and N-[2'-methoxy-(1,1'-biphenyl)-2-yl]-2-chloro-acetamide. MS (ISP): 883.7 (MH$^+$).

EXAMPLE 54

Preparation of I-54, compound of formula I, where R$^1$ is [2-benzo[b]thien-3-yl-2-oxoethyl]thio, R$^2$ is hydrogen, R$^3$ is methyl and Z is oxygen.

The title compound was prepared following the procedure described in example 4 starting from XV-3 and 1-benzo[b]thien-3-yl-2-bromoethanone. MS (ISP): 818.6 (MH$^+$).

EXAMPLE 55

Preparation of I-55, compound of formula I, where $R^1$ is [2-(3,4-dimethylphenylamino)-2-oxoethyl]thio, $R^2$ is hydrogen, $R^3$ is methyl and Z is oxygen.

The title compound was prepared following the procedure described in example 4 starting from XV-3 and N-(3,4-dimethylphenyl)-2-chloro-acetamide. MS (ISP): 805.69 (MH$^+$).

EXAMPLE 56

Preparation of I-56 compound of formula I, where $R^1$ is [2-[6-amino-9H-purine-9-yl]ethyl]thio, $R^2$ is fluoro, $R^3$ is methyl and Z is oxygen.

A] 9-(2-Iodoethyl)-6-amino-9H-purine

A suspension of 1 g (5 mmol) 9-(2-chlorooethyl)-6-amino-9H-purine (Journal of Heterocyclic Chemistry 1994, 31(2), 375–376) and 0.84 g potassium iodide in 40 ml n-butanol was refluxed for 27 hours under argon. N-Butanol was removed in vacuo and the solid residue was suspended in 40 ml water and the resulting slurry was stirred for 15 minutes. The product was isolated by filtration, washed with 40 ml water and dried at room temperature in vacuo. Yield: 0.67 g (45.8%). MS (ISP): 290.0 (MH$^+$). $^1$H-NMR (DMSO-d6): 3.69 (t, 2H), 4.50 (t, 2H), 7.25 (s broad, 2 H), 8.15 (s, 1H), 8.17 (s, 1H).

B] (3R or S, 3aR, 4R or S, 6R, 8R, 9R, 10R, 12S, 15R, 15aS)-9-[[2-O-Acetyl-3,4,6-trideoxy-3-(dimethylamino)-β-D-xylo-hexopyranosyl]oxy]-15-ethyl-12-fluoroctahydro-8-methoxy-3-methyldithio-4,6,8,10,12,15a-hexamethyl-2H-furo [2,3-c] oxacyclotetradecin-2,5,11,13 (3H,6H,12H)-tetrone; (XV-56).

To a solution of compound XIV-1 (0.225 g, 0.273 mmol) in 5 ml dichloromethane at room temperature was added dimethyl(methylthio)sulfonium tetrafluoroborate (0.107 g, 0.546 mmol). The reaction mixture was stirred at room temperature for 30 min. Thioglycolic acid (0.075 g, 0.82 mmol) was added to the deeply brown colored mixture and the reaction mixture was stirred for 15 min. The reaction mixture was taken up with 20 ml dichloromethane and washed twice with 25 ml aqueous 5% Na$_2$CO$_3$, once with 25 ml water, 25 ml brine and dried over sodium sulfate. Evaporation of the solvent under reduced pressure gave 0.19 g (94%) of the title compound as a light yellow foam. MS (ISP): 750.3 (MH$^+$). $^1$H-NMR (CDCl$_3$) diagnostic signals only: 0.90 (t, 3H), 1.09 (d, 3H), 1.16 (d, 3H), 1.30 (s, 3H), 1.35 (d, 3H), 1.49 (s, 3H), 1.55–1.75 (m, 2H),1.78 (d, 3H), 2.06 (s, 3H), 2.26 (s, 6H), 2.59 (s, 1H), 2.61 (s, 1H), 2.65 (s, 3H), 2.98–3.15 (m,3H), 3.53 (m, 2H), 4.06 (d, 1H), 4.31 (s, 1H), 4.38 (d, 1H), 4.74 (dd, 1H), 5.21(dd, 1H).

The title compound was obtained from 9-(2-iodoethyl)-6-amino-9H-purine and XV-56 according to example 4. MS (ISP): 823.2 (MH$^+$). $^1$H-NMR (CDCl$_3$) diagnostic signals only: 0.89 (t, 3H), 1.18 (d, 3H), 1.27.(d, 3H), 1.31 (d, 3H), 1.37 (s, 3H), 1.54 (s, 3H), 1.77 (d, 3H), 1.86–2.00 (m, 2H), 2.28 (s, 6H), 2.38 (s, 1H), 2.45 (m, 1H), 2.54 (s, 3H), 2.65 (m, 1H), 3.00–3.25 (m, 3H), 3.45–3.65 (m, 3H), 4.09 (d, 1H), 4.23 (s, 1H), 4.32 (d, 1H), 4.46 (m, 1H), 4.67 (m, 1H), 5.29 (dd, 1H), 5.53 (s broad, 2H), 8.28 (s, 1H),8.34 (s, 1H).

EXAMPLE 57

Preparation of I-57 compound of formula I, where $R^1$ is [3-[6-amino-9H-purine-9-yl]propyl]sulfinyl, $R^2$ is fluoro, $R^3$ is methyl and Z is oxygen.

A] Preparation of (3R or S, 3aR, 4R or S, 6R, 8R, 9R, 10R, 12S, 15R, 15aS) -3-[[2-[6-acetamido-9H-purine-9-yl]propyl]thio-9-[[2-O-acetyl-3,4,6-trideoxy-3-(dimethylamino)-β-D-xylo-hexopyranosyl]oxy]-15-ethyl-12-fluorooctahydro-8-methoxy-4,6,8,10,12,15a-hexamethyl-2H-furo [2,3-c] oxacyclotetradecin-2,5,11,13 (3H,6H,12H)-tetrone (XVIII-57)

100 mg (0.12 mmol) sulfide XII-13 were dissolved in 5 ml dichloromethane and treated with 50 µl (0.48 mmol) acetic acid anhydride and 70 µl (0.48 mmol) triethylamine. The reaction mixture was stirred for 115 hours at room temperature. After dilution with 25 ml dichloromethane, the mixture was washed twice with 25 ml 5% NaHCO$_3$, once with 25 ml water and with 25 ml brine. Evaporation gave 108 mg (98%) of XVIII-57 as a light yellow foam. MS (ISP): 903.3 (MH$^+$).

B] Preparation of (3R or S, 3aR, 4R or S, 6R, 8R, 9R, 10R, 12S, 15R, 15aS) -9-[[2-O-acetyl-3,4,6-trideoxy-3-(dimethylamino)-β-D-xylo-hexopyranosyl]oxy]-3-[[2-[6-acetamido-9H-purine-9-yl]propyl]sulfinyl-15-Ethyl-12-fluorooctahydro-8-methoxy-4,6,8,10,12,15a-hexamethyl-2H-furo [2,3-c] oxacyclotetradecin-2,5,11,13 (3H,6H,12H)-tetrone (XXXVIII-57)

55 mg (0.06 mmol) of compound XVIII-57 acetamide dissolved in 5 ml dichloromethane were treated with 51 mg (0.21 mmol) m-chloroperbenzoic acid and 35 mg sodium hydrogencarbonate at 0° C. for 1 hour. 5 ml of an 10 % aqueous sodium pyrosulfate solution were added and the two-phase system was stirred at room temperature for 1 hour. The pH of the solution was adjusted to pH 9 with saturated sodium carbonate solution and extracted twice with 25 ml dichloromethane. The combined organic extracts were washed with 25 ml 3% NaHCO$_3$, 25 ml brine, dried over Na2SO4 and evaporated to give 54 mg (96%) of XXXVIII-57 as a light yellow foam. MS (ISP): 937.4 (MH$^+$).

The title compound was prepared by treatment of 54 mg of crude XXXVIII-57 with a 5% ammonia solution in methanol at room temperature for 48 h. Evaporation of the solvent and chromatography of the residue with dichloromethane/methanol/ammonia 90:10:1 yielded 28 mg (55%) of I-59 as a colorless solid. MS (ISP): 853.4 (MH$^+$). $^1$H-NMR (CDCl$_3$) diagnostic signals only: 0.91 (t, 3H), 1.16 (d, 3H), 1.21 (d, 3H), 1.27 (d, 3H), 1.32 (s, 3H), 1.58 (s, 3H), 1.76 (d, 3H), 1.86–2.00 (m, 2H), 2.28 (s, 6H), 2.40–2.60 (m, 3H), 2.66 (s, 3H), 2.67 (s, 1H), 2.89 (m, 1H), 2.95–3.25 (m, 3H), 3.48–3.70 (m, 3H), 4.05 (d, 1H), 4.13 (d, 1H), 4.32 (d, 1H), 4.43 (t, 1H), 5.46 (dd, 1H), 5.56 (s broad, 2H), 7.92 (s, 1H), 8.36 (s, 1H).

EXAMPLE 58

Preparation of I-58 compound of formula I, where $R^1$ is [3-[6-amino-9H-purine-9-yl]propyl]sulfonyl, $R^2$ is fluoro, $R^3$ is methyl and Z is oxygen.

The title compound was prepared starting from compound XVIII-57 according to example 59, steps A and B with the only difference that the oxidation step was performed with 10 equivalents of m-chloroperbenzoic acid. MS (ISP): 869.3 (MH$^+$). $^1$H-NMR (CDCl$_3$) diagnostic signals only: 0.94 (t, 3H), 1.11 (d, 3H), 1.18 (d, 3H), 1.26 (d, 3H), 1.29 (d, 3H), 1.62 (s, 3H), 1.77 (d, 3H), 1.86–2.00 (m, 2H), 2.29 (s, 6H), 2.40–2.70 (m, 3H), 2.65 (s, 1H), 2.66(s, 3H), 3.11 (m, 1H), 3.15–3.25 (m, 3H), 3.35–3.70 (m, 3H), 4.09 (d, 1H), 4.31 (d, 1H), 4.40–4.55 (m, 2H), 4.70 (m, 1H), 5.50 (dd, 1H), 5.51 (s broad, 2H), 7.93 (s, 1H), 8.35(s, 1H).

EXAMPLE 59

Preparation of (3R or S, 3aS, 4R or S, 6R, 8R, 9R, 10R, 12R, 15R, 15aS)-15-Ethylhexadecahydro-8-methoxy-4,6,8,10,12,15a-hexamethyl-2,5,11,13-tetraoxo-9-[[-3,4,6-trideoxy-3-(dimethylamino)-β-D-xylo-hexopyranosyl]oxy]-N-[2-(2-pyridinyl)ethyl]-2H-furo [2,3-c] oxacyclotetradecin-3-carboxamide (I-59) compound of formula I, where $R^1$ is [[2-(2-pyridinyl)ethyl]amino]carbonyl, $R^2$ is hydrogen, $R^3$ is methyl and Z is oxygen.

A] 3-Oxo-3-[[2-(2-pyridinyl)ethyl]amino]-propanoic acid phenylmethyl ester

To an ice cold solution of 2.0 g (10.3 mmol) monobenzyl malonate in 20ml dichloromethane kept under argon were added 2.37 g (12.36 mmol) EDC*HCl and 3.7 g DMAP followed by 1.27 g (10.4 mmol) 2-pyridineethaneamine. The reaction mixture was allowed to warm to room temperature and was stirred over night at room temperature. The solvent was evaporated and the residue was dissolved in 50 ml ethyl acetate. The organic layer was washed twice with 20 ml aqueous $NaHCO_3$ 5% and twice with 20 ml brine, dried over $Na_2SO_4$ and evaporated. The crude product was purified by flash chromatography on silica gel ($CH_2Cl_2$:MeOH:$NH_3$ 98:2:0.01) to give 1.9 g (62%) of the desired compound as a white solid. MS (ISP): 299.2 ($MH^+$). $^1$H-NMR ($CDCl_3$): 2.97–3.03 (m, 2H), 3.33 (s, 2H), 3.60–3.75 (m, 2H), 5.15 (s, 2H), 7.11–7.17 (m, 2H), 7.29–7.39 (m, 5H), 7.52 (s, br, 1H), 7.55–7.63 (m, 1H), 8.50–8.56 (m, 1H).

B] 3-Oxo-3-[[2-(2-pyridinyl)ethyl]amino]-propanoic acid 900 mg (3.03 mmol) 3-oxo-3-[[2-(2-pyridinyl)ethyl]amino]-propanoic acid phenylmethyl ester were dissolved in 25 ml THF and 15 mg palladium on charcoal (10%) were added. The reaction was kept under an atmosphere of hydrogen using a balloon for 10 hours. The mixture was filtered through dicalite. The solids were washed with THF and methanol. The combined filtrate was evaporated and dried under high vacuum. The crude product (300 mg) was used without further purification for the next reaction. $^1$H-NMR ($CDCl_3$): 2.82–2.90 (m, 2H), 3.08 (s, 2H), 3.38–3.47 (m, 2H), 7.19–7.28 (m, 2H), 7.65–7.74 (m, 1H), 8.16–8.24 (m, br, 1H), 8.47–8.51 (m, H).

C] (10E)-10,11-Didehydro-11-deoxy-6-O-methyl-erythromycin 2',4"-dibenzoate 12-[[[[2-(2-pyridinyl)ethyl]amino]carbonyl]acetate] (VIII-59)

300 mg (1.44 mmol) 3-oxo-3-[[2-(2-pyridinyl)ethyl]amino]-propanoic acid, 450 mg (0.48 mmol) of compound VI-19 and 18 mg (0.15 mmol) DMAP were suspended in 10 ml dichloromethane. A solution of 300 mg (1.45 mmol) DCC in 5 ml dichloromethane were added dropwise over a period of 4 hours. The reaction was stirred for another 4 hours at room temperature and 10 ml saturated aqueous $NaHCO_3$ were added. The mixture was extracted twice with 10 ml dichloromethane. The combined organic layers were dried over $Na_2SO_4$ and evaporated. The crude product was purified by flash chromatography on silica gel ($CH_2Cl_2$:MeOH:$NH_3$ 98:2:0.01) to give 449 mg (83%) of the desired compound. MS (ISP): 1128.6 (MHz), 565.4 ($[MH_2]^{++}$).

D] (3R or S, 3aS, 4R or S, 6R, 8R, 9R, 10S, 11S, 12R, 15aS)-9-[[2-O-Benzoyl-3,4,6-trideoxy3-(dimethylamino)-β-D-xylo-hexopyranosyl]oxy]-11-[[4-O-benzoyl-2,6-dideoxy-3-C-methyl-3-O-methyl-α-L-ribo-hexopyranosyl]oxy] -15-ethylhexadecahydro-8-methoxy-4,6,8,10,12,15a-hexamethyl-2,5,13-trioxo-N-[2-(2-pyridinyl)ethyl]-2H-furo [2,3-c] oxacyclotetradecin-3-carboxamide (IX-59)

To an ice cold solution of 250 mg (0.22 mmol) compound VIII-59 in 5 ml dry THF kept under argon were added 0.28 ml (0.28 mmol) of a solution of KO$^t$Bu in THF (1M). The reaction was stirred at 0° C. during two hours. The mixture was diluted with 50 ml dichloromethane. The organic layer was washed twice with 10 ml aqueous $NaHCO_3$, 10 ml brine, dried over $Na_2SO_4$ and evaporated. The crude product was purified by flash chromatography on silica gel ($CH_2Cl_2$:MeOH:$NH_3$ 98:2:0.01) to give 160 mg (64%) of the desired compound. MS (ISP): 1128.6 ($MH^+$), 565.3 ($[MH_2]^{++}$).

E] (3R or S, 3aS, 4R or S, 6R, 8R, 9R, 10S, 11S, 12R, 15R, 15aS)-9-[[2-O-Benzoyl-3,4,6-trideoxy-3-(dimethylamino)-β-D-xylo-hexopyranosyl]oxy]-15-ethylhexadecahydro-11-hydroxy-8-methoxy-4,6,8,10,12,15a-hexamethyl-2,5,13-trioxo-N-[2-(2-pyridinyl)ethyl]-2H-furo [2,3-c] oxacyclotetradecin-3-carboxamide (XI-59)

To a solution of 165 mg (0.146 mmol) of compound IX-59 in 5 ml ethanol were added 1.54 ml HCl 2N. The reaction mixture was heated to 45° C. during 24 hours. Now 1.54 ml NaOH 2N were added followed by 20 ml water and the solution was extracted twice with 50 ml ethyl acetate. The combined organic layers were dried over $Na_2SO_4$ and evaporated. The crude product was purified by flash chromatography on silica gel ($CH_2Cl_2$:MeOH:$NH_3$ 98:2:0.01) to give 66 mg (52%) of the desired compound. MS (ISP): 866.6 ($MH^+$). $^1$H-NMR ($CDCl_3$): 0.71 (d, 3H), 0.82 (t, 3H), 0.95 (d, 3H), 1.00 (s, 3H), 1.08 (d, 3H), 1.13 (d, 3H), 1.29 (s, 3H), 2.25 (s, 6H), 2.46–2.55 (m, 1H), 2.74–2.88 (m, 2H), 2.90–3.06 (m, 4H), 3.18 (s, 3H), 3.19–3.26 (mn, 1H), 3.50–3.63 (m, 2H), 3.64–3.81 (m, 3H), 3.87 (d, 1H), 4.66 (d, br, 1H), 4.78 (d, 1H), 4.92 (dd, 1H), 4.99 (dd, 1H), 6.83 (dd, br, 1H), 7.10–7.20 (m, 2H), 7.40–7.47 (m, 2H), 7.51–7.64 (m, 2H), 8.02–8.09 (m, 2H), 8.50–8.56 (m, 1H).

F] (3R or S, 3aS, 4R or S, 6R, 8R, 9R, 10R, 11 S, 12R, 15R, 15aS)-9-[[2-O-Benzoyl-3,4,6-trideoxy-3-(dimethylamino)-β-D-xylo-hexopyranosyl]oxy]-15-ethylhexadecahydro-8-methoxy-4,6,8,10,12,15a-hexamethyl-2,5,11,13-tetraoxo-N-[2-(2-pyridinyl)ethyl]-2H-furo [2,3-c] oxacyclotetradecin-3-carboxamide (XII-59)

This compound was prepared from 30 mg (0.035 mmol) of XI-59 according to the procedure described in example 1 step E. The crude product was purified by flash chromatography on silica gel ($CH_2Cl_2$:MeOH:$NH_3$ 98:2:0.01) to give 23 mg (78%) of XII-59 as a mixture of isomers. MS (ISP): 864.5 ($MH^+$).

G] (3R or S, 3aS, 4R or S, 6R, 8R, 9R, 10R, 12R, 15R, 15aS)-15-Ethylhexadecahydro-8-methoxy-4,6,8,10,12,15a-hexamethyl-2,5,11,13-tetraoxo-9-[[-3,4,6-trideoxy-3-(dimethylamino)-β-D-xylo-hexopyranosyl]oxy]-N-[2-(2-pyridinyl)ethyl]-2H-furo [2,3-c] oxacyclotetradecin-3-carboxamide (I-59)

The product of step F (23 mg, 0.027 mmol) was dissolved in 5 ml methanol and stirred for 5 days at room temperature. The solvent was removed under reduced pressure and the product was purified by HPLC RP-C18 with a gradient of 10 to 50% acetonitrile in water/formic acid 99.9:0.1. MS (ISP): 760.5 ($MH^+$).

EXAMPLE 60

Preparation of I-60, compound of formula I, where $R^1$ [[2-(3-pyridinyl)ethyl]amino]carbonyl, $R^2$ is hydrogen, $R^3$ is methyl and Z is oxygen.

The title compound was prepared following the procedures described in example 59 steps A–G starting from monobenyzl malonate, 3-pyridineethaneamine and VI-19. MS (ISP): 760.5 (MH$^+$).

EXAMPLE A

Tablets of the following composition are manufactured in the usual manner:

|  | mg/tablet |
|---|---|
| Active substance | 500–1000 |
| Lactose |  |
| Corn starch |  |
| Microcrystalline cellulose |  |
| Magnesium stearate |  |
| Tablet weight | 1000–1500 |

EXAMPLE B

Capsules of the following composition are manufactured:

|  | mg/capsule |
|---|---|
| Active substance | 500–1000 |
| Lactose |  |
| Corn starch |  |
| Talc |  |
| Capsule fill weight | 1000–1500 |

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

EXAMPLE C

Suppositories of the following composition are manufactured:

|  | mg/supp. |
|---|---|
| Active substance | 500 |
| Suppository mass |  |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The invention claimed is:

1. A compound of the formula

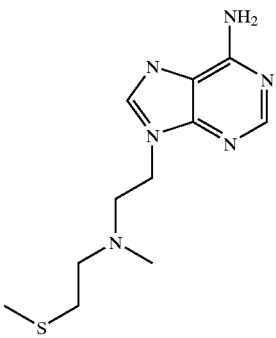

wherein
$R^1$ is —Y—X—Q;
Y is S, SO, SO$_2$, H$_3$, CH$_2$O, or CO;
X is a bond or a linear group with up to 9 atoms selected from the group consisting of C, N, O and S, of which up to 2 atoms can be N, one atom can be O or S, one carbon atom can appear as a CO group, one sulfur atom can appear as an SO$_2$ group and two adjacent C atoms can be present as —CH=CH— or —C≡C—;
Q is hydrogen, alkyl, heterocyclyl or aryl, which heterocyclyl and aryl groups may be further substituted;
$R^2$ is hydrogen or fluorine;
$R^3$ is methyl, —(CH$_2$)$_3$—R$^5$, —CH$_2$CH=CH—R$^5$ or —CH$_2$C≡C—R$^5$;
$R^5$ is heterocyclyl or aryl, which heterocyclyl and aryl groups may be further substituted;
Z is O or NOR$^4$;
$R^4$ is hydrogen, alkyl, heterocyclyl, aryl, heterocyclyl alkyl or aralkyl;
* indicates a chiral centre which is in the (R) or (S) form,
and/or pharmaceutically acceptable acid addition salts or in vivo cleavable esters thereof, provided that not simultaneously $R^2$ is hydrogen, $R^3$ is methyl and Z is O when simultaneously
$R^1$ is —S(L)$_m$R$^6$, —S(O)(L)$_m$R$^6$, or —S(O)$_2$(L)$_m$R$^6$;
L represents —(CH$_2$)$_{n'}$— or —(CH$_2$)nZ$^1$(CH$_2$)$_{n'}$—;
m is 0 or 1;
n is 1, 2, 3, or 4;
N' is 0, 1, 2, 3, or 4;
$Z^1$ is O, S or NH; and
$R^6$ is hydrogen, alkyl, heterocyclyl or aryl; which heterocyclyl and aryl groups may be further substituted.

2. The compound according to claim 1, wherein $R^3$ is methyl.

3. The compound according to claim 1, wherein $R^3$ is

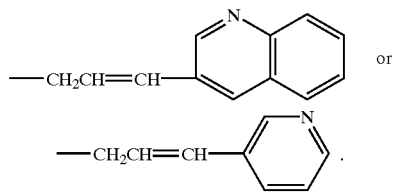

4. The compound according to claim 1, wherein Q is

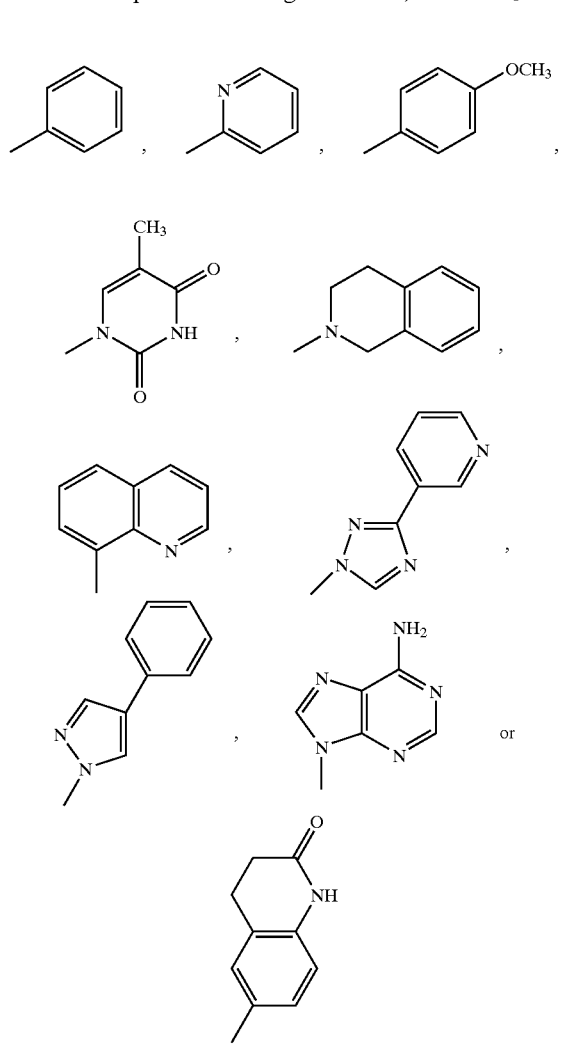

5. The compound according to claim 1, wherein X is a linear group with 2 to 5 atoms.

6. The compound according to claim 5 wherein X is $(CH_2)_n$, $(CH_2)_m OCH_2$, $(CH_2)_2 NCH_3 (CH_2)_2$ or $(CH_2)_p COW$; where n and p are 1–3, m is 0–3 and W is absent or O or NH.

7. The compound according to claim 1, wherein Y is S, $SO_2$ or CO.

8. The compound according to claim 7, wherein Y is S.

9. The compound according to claim 1, wherein Y is $CH_2O$.

10. The compound according to claim 1, wherein $R^1$ is a radical selected from the group consisting of:

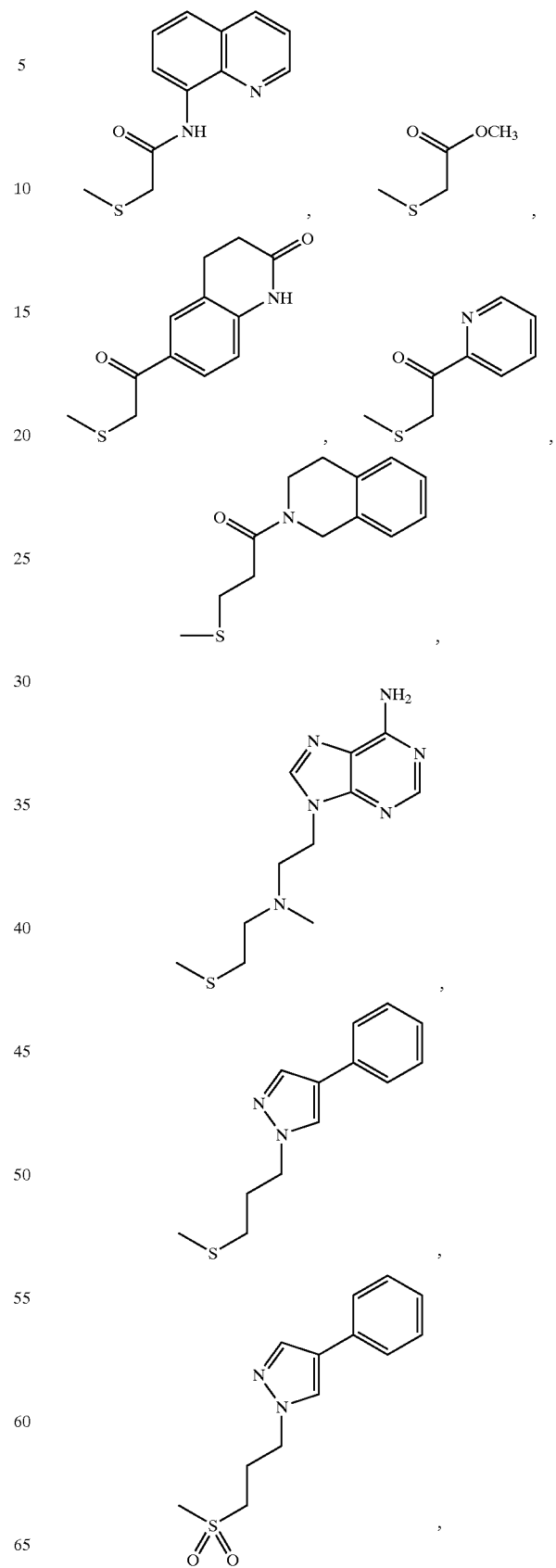

-continued

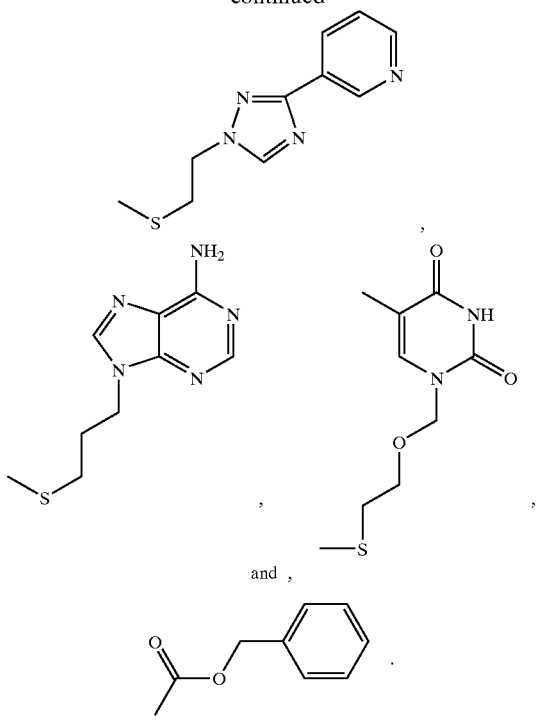

and ,

11. The compound according to formula I in claim 1, wherein
  $R^1$ is [(4-methoxyphenyl) methyl]thio, $R^2$ is fluoro, $R^3$ is methyl and Z is oxygen;
  $R^1$ is [(4-methoxyphenyl)methyl]sulfonyl, $R^2$ is fluoro, $R^3$ is methyl and Z is oxygen;
  $R^1$ is [2-(2-amino-quinolin-8-yl) 2-oxo-ethyl]thio, $R^2$ is hydrogen, $R^3$ is methyl and Z is oxygen;
  $R^1$ is [2-methoxy-2-oxoethyl]-thio, $R^2$ is hydrogen, $R^3$ is methyl and Z is oxygen
  $R^1$ is [2-(3,4-dihydro-1H-2-oxo-quinolin-6-yl)-2-oxoethyl]thio, $R^2$ is hydrogen, $R^3$ is methyl and Z is oxygen;
  $R^1$ is [2-oxo-2-(pyridin-2-yl)ethyl]-thio, $R^2$ is hydrogen, $R^3$ is methyl and Z is oxygen;
  $R^1$ is 3-[3-oxo-3-(1,2,3,4-tetrahydro-isoquinolin-2-yl) propyl]thio, $R^2$ is hydrogen, $R^3$ is methyl and Z is oxygen;
  $R^1$ is 3-[[[2-(6-amino-9H-purin-9-yl)ethyl]methylamino]-ethyl]thio, $R^2$ is hydrogen, $R^3$ is methyl and Z is oxygen;
  $R^1$ is [3-(4-phenyl-1H-pyrazol-1-yl)-propyl]thio, $R^2$ is fluoro, $R^3$ is methyl and Z is oxygen;
  $R^1$ is [3-(4-phenyl-1H-pyrazol-1-yl)-propyl]sulfonyl, $R^2$ is fluoro $R^3$ is methyl and Z is oxygen;
  $R^1$ is [2-[[5-methyl-2,4-(1H,3H)-pyrimidinedione-1-yl]methoxy]ethyl]thio, $R^2$ is fluoro, $R^3$ is methyl and Z is oxygen; or
  $R^1$ is (phenylmethoxy)carbonyl, $R^2$ is hydrogen, $R^3$ is methyl and Z is oxygen;
or a pharmaceutically acceptable acid addition salt thereof.

12. The compound according to formula I in claim 1, wherein
  $R^1$ is selected from the group consisting of
    [2-[4-(dimethylamino)phenyl]-2-oxoethyl]thio,
    [2-(1H-2,3-dihydroindol-1-yl)-2-oxoethyl]thio,
    [2-[(3-pyridinylcarbonyl)amino]ethyl]thio,
    [2-[(2,1,3-benzoxadiazol-5-ylcarbonyl)amino]ethyl]thio,
    [2-[[[5-(2-pyridinyl)thien-2-yl]sulfonyl]amino]ethyl]thio,
    [2-[[(2,1,3-benzoxadiazol-4-yl)sulfonyl]amino]ethyl]thio,
    [3-(4-cyanophenyl)prop-2-ynyl]thio,
    [2-[[(phenylmethyl)amino]sulfonyl]ethyl]thio,
    [2-(8-quinolinylamino)-2-oxoethyl]thio,
    [2-(5-quinolinylamino)-2-oxoethyl]thio,
    [2-[(3-quinolinylcarbonyl)amino]ethyl]thio,
    [2-[[[5-(dimethylamino)-1-naphthalenyl]sulfonyl]amino]ethyl]thio,
    [2-[[(8-quinolinyl)sulfonyl]amino]ethyl]thio,
    [2-[[(1,3-benzodioxol-5-yl)methyl]amino]-2-oxoethyl]thio,
    [2-[(2-furanylmethyl)amino]-2-oxoethyl]thio,
    [2-[(2-pyridinylmethyl)amino]-2-oxoethyl]thio,
    [2-[(5-methyl-3-isoxazolyl)amino]-2-oxoethyl]thio,
    [2-[(2-benzothiazolylmethyl)amino]-2-oxoethyl]thio,
    [2-[(1H-imidazol-2-ylmethyl)amino]-2-oxoethyl]thio,
    [3-(5-quinolinylamino)-3-oxopropyl]thio,
    [2-(2-quinolinylamino)-2-oxoethyl]thio,
    [2-(6-quinolinylamino)-2-oxoethyl]thio,
    [2-(3-quinolinylamino)-2-oxoethyl]thio,
    [2-(5-isoquinolinylamino)-2-oxoethyl]thio,
    [3-(6-quinolinylamino)-3-oxopropyl]thio,
    [3-(3-quinolinylamino)-3-oxopropyl]thio,
    [2-[(3-pyridinylcarbonyl)amino]ethyl]sulfonyl,
    [2-[(2,1,3-benzoxadiazol-5-ylcarbonyl)amino]ethyl]sulfonyl,
    [2-[2,4-dimethoxyphenyl]-2-oxoethyl]thio,
    [2-[(5-cyanopyridin-2-yl)amino]ethyl]thio,
    [2-[(6-quinolinylcarbonyl)amino]ethyl]thio,
    [2-[[[6-(1H-imidazol-1-yl)-3-pyridinyl]carbonyl]amino]ethyl]thio,
    [2-[(8-quinolinylcarbonyl)amino]ethyl]thio,
    [2-[[[6-(1H-pyrazol-1-yl)-3-pyridinyl]carbonyl]amino]ethyl]thio,
    [2-[(1H-purin-6-yl)amino]ethyl]thio,
    [2-[(6-bromo-2-methyl-quinazolin-4-yl)amino]ethyl]thio,
    [2-[[2'-methoxy(1,1'-biphenyl)-2-yl]amino]-2-oxoethyl]thio,
    [2-benzo[b]thien-3-yl-2-oxoethyl]thio,
    [2-(3,4-dimethylphenylamino)-2-oxoethyl]thio,
    [2-[6-amino-9H-purine-9-yl]ethyl]thio,
    [3-[6-amino-9H-purine-9-yl]propyl]sulfinyl,
    [3-[6-amino-9H-purine-9-yl]propyl]sulfonyl,
    [[2-(2-pyridinyl)ethyl]amino]carbonyl, and
    [[2-(3-pyridinyl)ethyl]amino]carbonyl;
or a pharmaceutically acceptable acid addition salt thereof.

13. The compound according to formula I in claim 1, wherein $R^1$ is [2-[3-(3-pyridinyl)-1H-1,2,4-triazol-1-yl]ethyl]thio, $R^2$ is fluoro, $R^3$ is methyl and Z is oxygen, said compound being named (3R or S, 3aR, 4R or S, 6R, 8R, 9R, 10 R, 12S, 15R, 15aS)-15-Ethyl-12-fluorooctahydro-8-methoxy-4,6,8,10,12,15a-hexamethyl-3-[[2-[3-(3-pyridinyl)-1H-1,2,4-triazol-1-yl]ethyl]thio]-9-[[3,4,6-trideoxy-3-(dimethylamino)-β-D-xylo-hexopyranosyl]oxy]-2H-furo[2,3-c] oxacyclotetradecin-2,5,11,13 (3H,6H,12H)-tetrone or a pharmaceutically acceptable acid addition salt thereof.

14. The compound according to formula I in claim 1, wherein R$^1$ is [3-[6-Amino-9H-purine-9-yl]propyl]thio, R$^2$ is fluoro, R$^3$ is methyl and Z is oxygen, said compound being named (3R or S, 3aR, 4R or S, 6R, 8R, 9R, 10R, 12S, 15R, 15aS)-3-[[3-[6-Amino-9H-purine-9-yl]propyl]thio]-15-ethyl-12-fluorooctahydro-8-methoxy-4,6,8,10,12,15a-hexamethyl-3-9-[[3,4,6-trideoxy-3-(dimethylamino)-β-D-xylo-hexopyranosyl]oxy]-2H-furo [2,3-c] oxacyclotetradecin-2,5,11,13 (3H,6H,12H)-tetrone
or a pharmaceutically acceptable acid addition salt thereof.

15. A compound of the formula

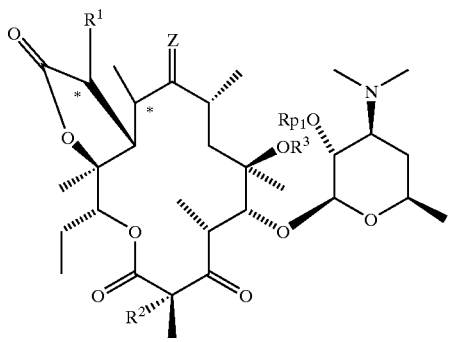

A wherein
R$^1$ is —Y—X—Q;
Y is S, SO, SO$_2$, CH$_2$O, or CO;
X is a bond or a linear group with up to 9 atoms selected from the group consisting of C, N, O and S, of which up to 2 atoms can be N, one atom can be O or S, one carbon atom can appear as a CO group, one sulfur atom can appear as an SO$_2$ group and two adjacent C atoms can be present as —CH=CH— or —C≡C—;
Q is hydrogen, alkyl, heterocyclyl or aryl, which heterocyclyl and aryl groups may be further substituted;
R$^2$ is hydrogen or fluorine;
R$^3$ is methyl, —(CH$_2$)$_3$—R$^5$, —CH$_2$CH=CH—R$^5$ or —CH$_2$C≡C—R$^5$;
R$^5$ is heterocyclyl or aryl, which heterocyclyl and aryl groups may be further substituted;
Z is O or NOR$^4$;
R$^4$ is hydrogen, alkyl, heterocyclyl, aryl, heterocyclyl alkyl or aralkyl;
* indicates a chiral centre which is in the (R) or (S) form; and
Rp$_1$ is acetyl or benzoyl,
or a pharmaceutically acceptable acid addition salt or in vivo cleavable esters thereof, provided that not simultaneously R$^2$ is hydrogen, R$^3$ is methyl and Z is o when simultaneously
R$^1$ is —S(L)$_m$R$^6$, —S(O)(L)$_m$R$^6$, or —S(O)$_2$(L)$_m$R$^6$;
L represents —(CH$_2$)$_n$— or —(CH$_2$)nZ$^1$(CH$_2$)$_{n'}$—;
m is 0 or 1;
n is 1, 2, 3, or 4;
n' is 0, 1, 2, 3, or 4;
Z$^1$ is O, S or NH; and
R$^6$ is hydrogen, alkyl, heterocyclyl or aryl; which heterocyclyl and aryl groups may be further substituted.

16. A process for making the compound of claim 1, comprising deacylating a compound of the formula

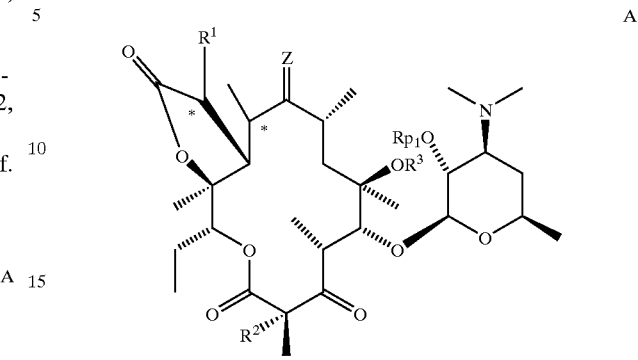

A wherein
R$^1$ is —Y—X—Q;
Y is S, SO, SO$_2$, CH$_2$O, or CO;
X is a bond or a linear group with up to 9 atoms selected from the group consisting of C, N, O and S, of which up to 2 atoms can be N, one atom can be O or S, one carbon atom can appear as a CO group, one sulfur atom can appear as an SO$_2$ group and two adjacent C atoms can be present as —CH=CH— or —C≡C—;
Q is hydrogen, alkyl, heterocyclyl or aryl, which heterocyclyl and aryl groups may be further substituted;
R$^2$ is hydrogen or fluorine;
R$^3$ is methyl, —(CH$_2$)$_3$—R$^5$, —CH$_2$CH=CH—R$^5$ or —CH$_2$C≡C—R$^5$;
R$^5$ is heterocyclyl or aryl, which heterocyclyl and aryl groups may be further substituted;
Z is O or NOR$^4$;
R$^4$ is hydrogen, alkyl, heterocyclyl, aryl, heterocyclyl alkyl or aralkyl;
* indicates a chiral centre which is in the (R) or (S) form; and
Rp$_1$ is acetyl or benzoyl,
or a pharmaceutically acceptable acid addition salt or in vivo cleavable esters thereof, provided that not simultaneously R$^2$ is hydrogen, R$^3$ is methyl and Z is o when simultaneously
R$^1$ is —S(L)$_m$R$^6$, —S(O)(L)$_m$R$^6$, or —S(O)$_2$(L)$_m$R$^6$;
L represents —(CH$_2$)$_n$— or —(CH$_2$)nZ$^1$(CH$_2$)$_{n'}$—;
m is 0 or 1:
n is 1, 2, 3, or 4;
n' is 0, 1, 2, 3, or 4;
Z$^1$ is O, S or NH; and
R$^6$ is hydrogen, alkyl, heterocyclyl or aryl; which heterocyclyl and aryl groups may be further substituted.

17. A method of treating bacterial infections comprising administering to a patient in need thereof, an effective amount of a compound according to claim 1.

18. A pharmaceutical composition comprising a compound according to claim 1 and a pharmaceutically acceptable carrier or excipient.

19. A compound of the formula

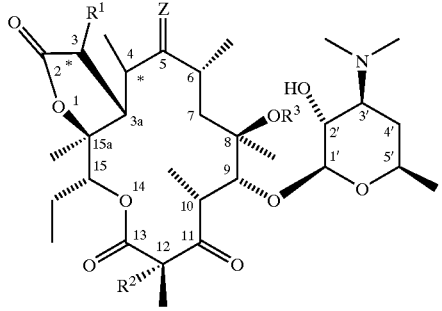

I wherein

R¹ is —Y—X—Q;

Y is S, SO, SO₂, or CO;

X is a bond or a linear group with up to 9 atoms selected from the group consisting of C, N, O and S, of which up to 2 atoms can be N, one atom can be O or S, one carbon atom can appear as a CO group, one sulfur atom can appear as an SO₂ group and two adjacent C atoms can be present as —CH=CH— or —C≡C—;

Q is selected from the group consisting of

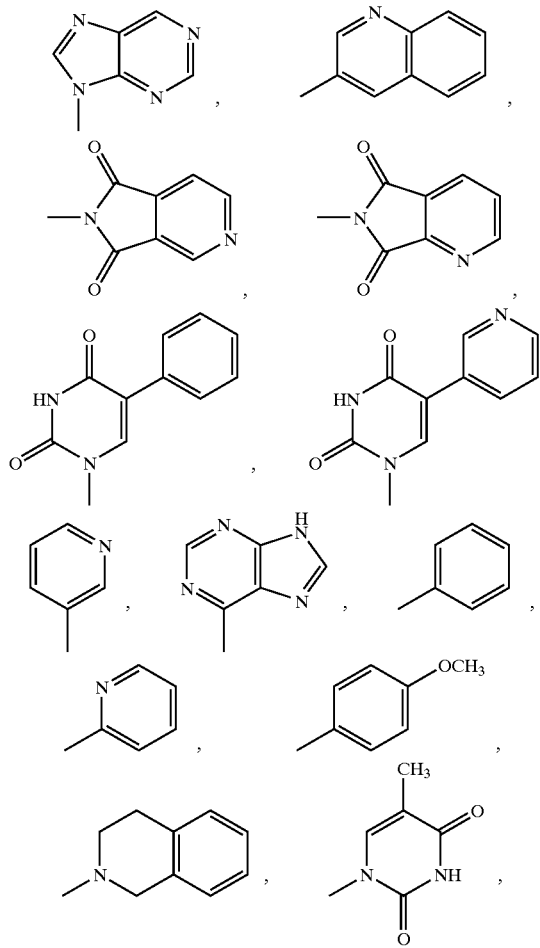

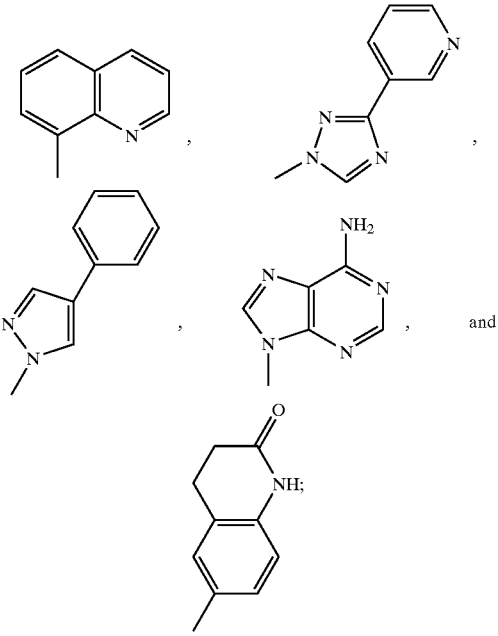

R² is hydrogen or fluorine;

R³ is methyl;

R⁵ is heterocyclyl or aryl, which heterocyclyl and aryl groups may be further substituted;

Z is O;

R⁴ is hydrogen, alkyl, heterocyclyl, aryl, heterocyclyl alkyl or aralkyl;

* indicates a chiral centre which is in the (R) or (S) form, or a pharmaceutically acceptable acid addition salt or in vivo cleavable esters thereof, provided that not simultaneously R² is hydrogen, R³ is methyl and Z is o when simultaneously R¹ is —S(L)$_m$R⁶, —S(O)(L)$_m$R⁶, or —S(O)₂(L)$_m$R⁶;

L represents —(CH₂)$_n$— or —(CH₂)nZ¹(CH₂)$_{n'}$—;

m is 0 or 1;

n is 1, 2, 3, or 4;

n' is 0, 1, 2, 3, or 4;

Z¹ is O, S or NH; and

R⁶ is hydrogen, alkyl, heterocyclyl or aryl; which heterocyclyl and aryl groups may be further substituted.

20. The compounds of claim 1 wherein

R¹ is a group of formula

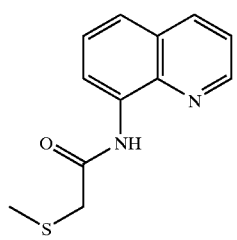

and R² is hydrogen, R³ is methyl and Z is O.

21. The compounds of claim 1 wherein
R¹ is a group of formula

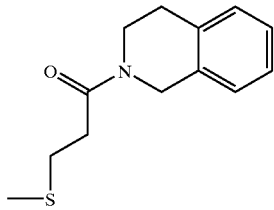

and R² is hydrogen, R³ is methyl and Z is O.

22. The compound of claim 1 wherein
R¹ is a group of formula

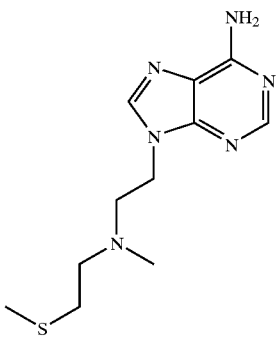

and R² is hydrogen, R³ is methyl and Z is O.

23. The compound of claim 1 wherein
R¹ is a group of formula

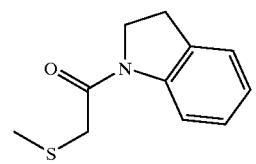

and R² is hydrogen, R³ is methyl and Z is O.

24. The compound of claim 1 wherein
R¹ is a group of formula

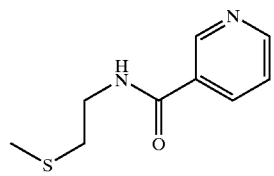

and R² is hydrogen, R³ is methyl and Z is O.

25. The compound of claim 1 wherein
R¹ is a group of formula

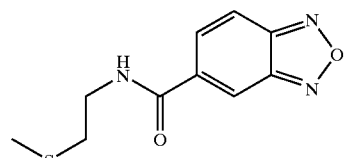

and R² is hydrogen, R³ is methyl and Z is O.

26. The compound of claim 1 wherein
R¹ is a group of formula

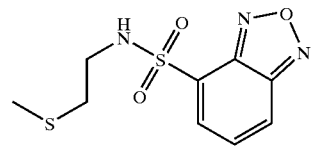

and R² is hydrogen, R³ is methyl and Z is O.

27. The compound of claim 1 wherein
R¹ is a group of formula

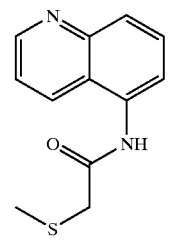
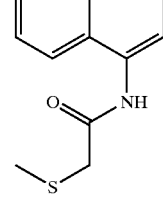

and R² is hydrogen, R³ is methyl and Z is O.

28. The compound of claim 1 wherein
R¹ is a group of formula

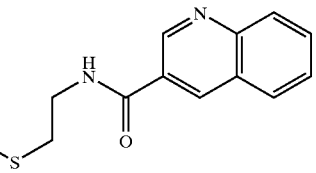

and R² is hydrogen, R³ is methyl and Z is O.

29. The compound of claim 1 wherein

R¹ is a group of formula

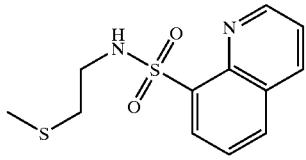

and R² is hydrogen, R³ is methyl and Z is O.

30. The compound of claim 1 wherein

R¹ is a group of formula

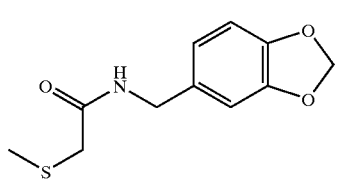

and R² is hydrogen, R³ is methyl and Z is O.

31. The compound of claim 1 wherein

R¹ is a group of formula

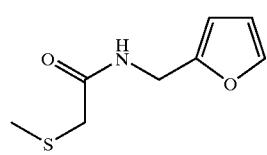

and R² is hydrogen, R³ is methyl and Z is O.

32. The compound of claim 1 wherein

R¹ is a group of formula

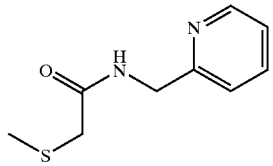

and R² is hydrogen, R³ is methyl and Z is O.

33. The compound of claim 1 wherein

R¹ is a group of formula

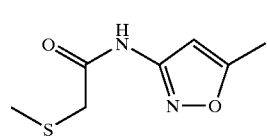

and R² is hydrogen, R³ is methyl and Z is O.

34. The compound of claim 1 wherein

R¹ is a group of formula

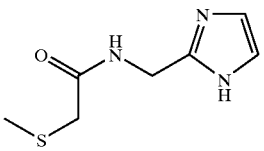

and R² is hydrogen, R³ is methyl and Z is O.

35. The compound of claim 1 wherein

R¹ is a group of formula

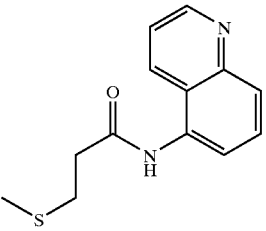

and R² is hydrogen, R³ is methyl and Z is O.

36. The compound of claim 1 wherein

R¹ is a group of formula

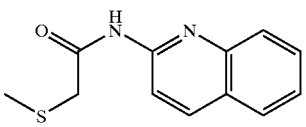

and R² is hydrogen, R³ is methyl and Z is O.

37. The compound of claim 1 wherein

R¹ is a group of formula

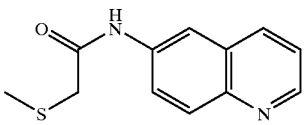

and R² is hydrogen, R³ is methyl and Z is O.

38. The compound of claim 1 wherein

R¹ is a group of formula

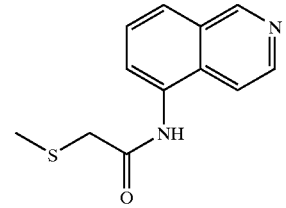

and R² is hydrogen, R³ is methyl and Z is O.

39. The compound of claim 1 wherein

R¹ is a group of formula

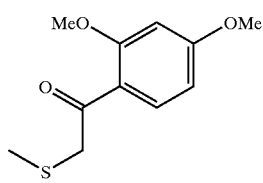

and R² is hydrogen, R³ is methyl and Z is O.

40. The compound of claim 1 wherein

R¹ is a group of formula

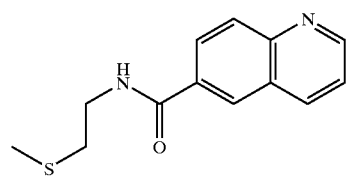

and R² is hydrogen, R³ is methyl and Z is O.

41. The compound of claim 1 wherein

R¹ is a group of formula

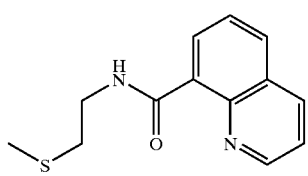

and R² is hydrogen, R³ is methyl and Z is O.

42. The compound of claim 1 wherein

R¹ is a group of formula

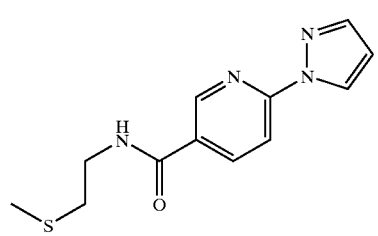

and R² is hydrogen, R³ is methyl and Z is O.

43. The compound of claim 1 wherein

R¹ is a group of formula

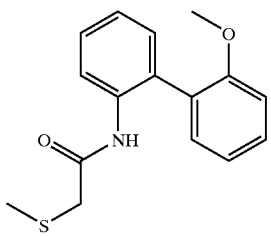

and R² is hydrogen, R³ is methyl and Z is O.

44. The compound of claim 1 wherein

R¹ is a group of formula

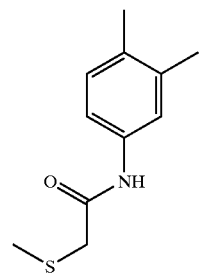

and R² is hydrogen, R³ is methyl and Z is O.

45. The compound of claim 1 wherein

R¹ is a group of formula

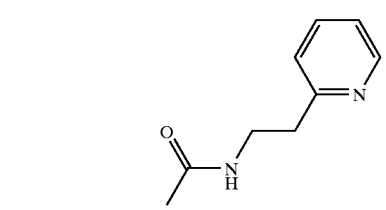

and R² is hydrogen, R³ is methyl and Z is O.

46. The compound of claim 1 wherein

R¹ is a group of formula

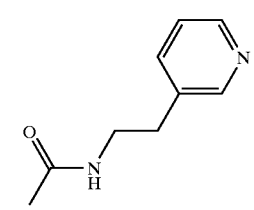

and R² is hydrogen, R³ is methyl and Z is O.

47. The compound of claim 1
wherein
R¹ is a group of formula

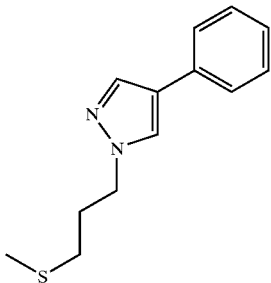

and R² is fluoro, R³ is methyl and Z is O.
48. The compound of claim 1
wherein
R¹ is a group of formula

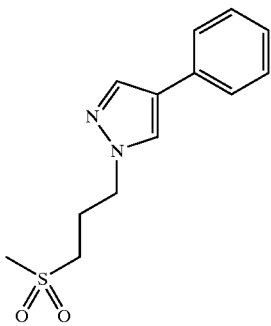

and R² is fluoro, R³ is methyl and Z is O.
49. The compound of claim 1
wherein
R¹ is a group of formula

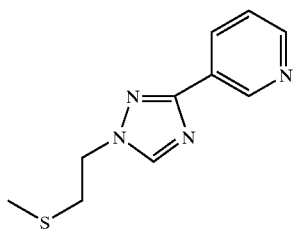

and R² is fluoro, R³ is methyl and Z is O.
50. The compound of claim 1
wherein
R¹ is a group of formula

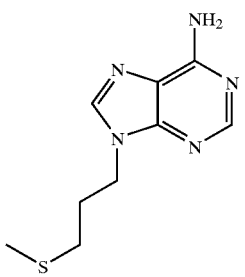

and R² is fluoro, R³ is methyl and Z is O.

51. The compound of claim 1
wherein
R¹ is a group of formula

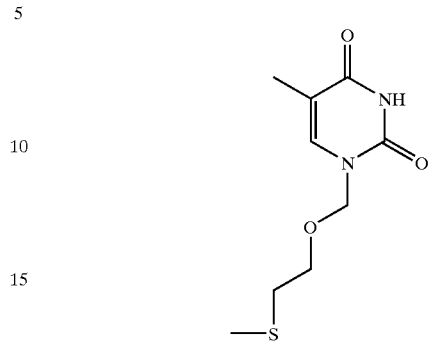

and R² is fluoro, R³ is methyl and Z is O.
52. The compound of claim 1
wherein
R¹ is a group of formula

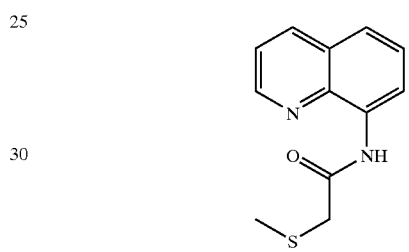

and R² is fluoro, R³ is methyl and Z is O.
53. The compound of claim 1
wherein
R¹ is a group of formula

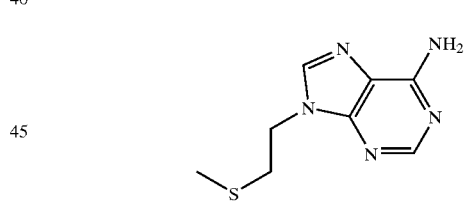

and R² is fluoro, R³ is methyl and Z is O.
54. The compound of claim 1
wherein
R¹ is a group of formula

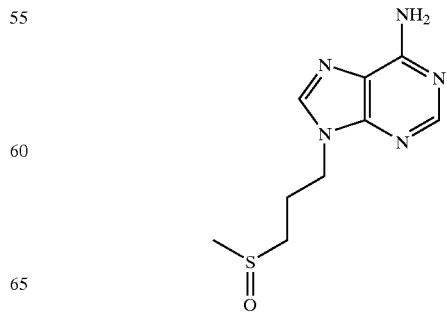

and R² is fluoro, R³ is methyl and Z is O.

55. The compound of claim 1 wherein
R$^1$ is a group of formula
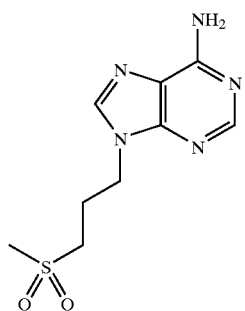
and R$^2$ is fluoro, R$^3$ is methyl and Z is O.
56. The compound of claim 1 wherein
R$^2$ is hydrogen, R$^3$ is methyl and Z is O; and
R$^1$ is selected from the group consisting of radicals of the formulae
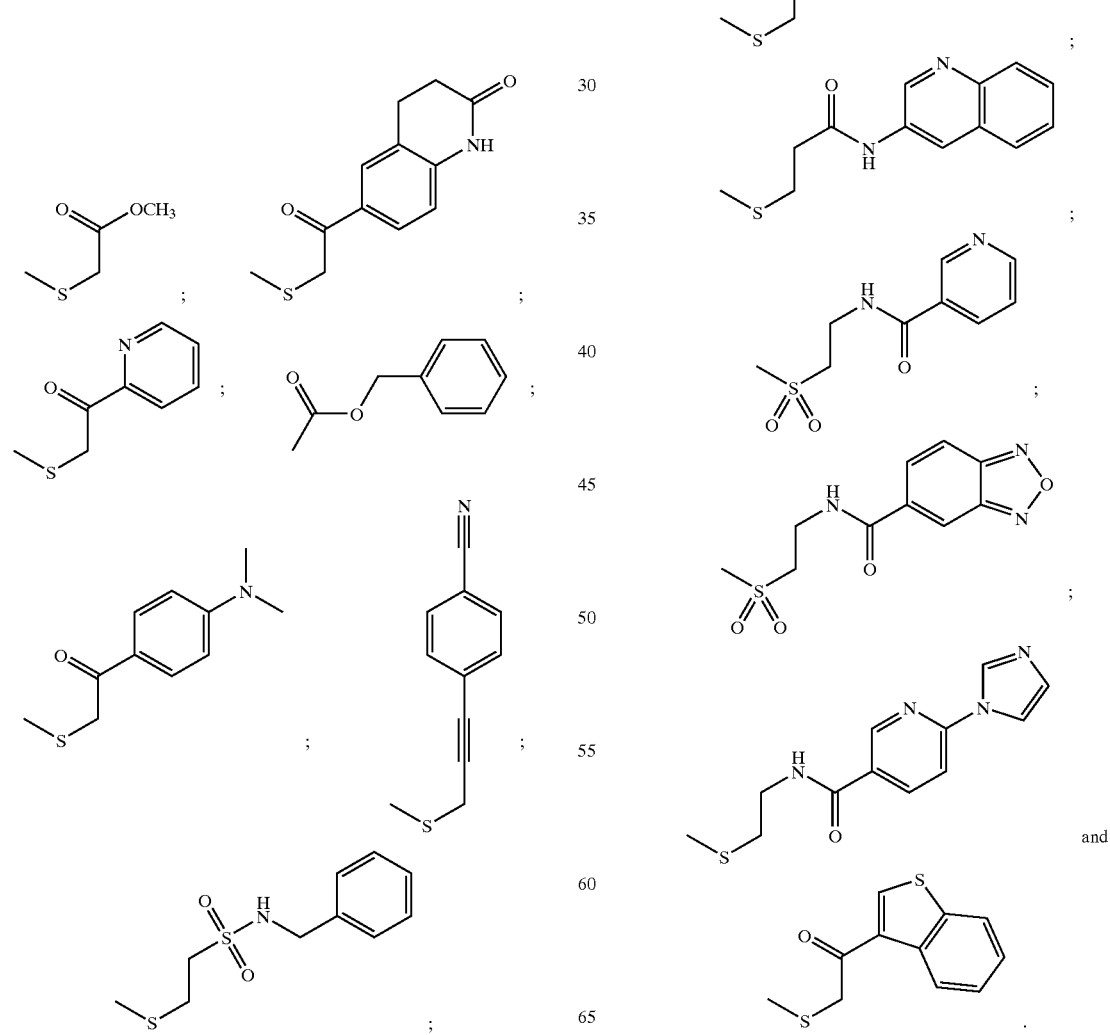

57. The compound of claim 1 wherein
R³ is methyl and Z is O; and
and R¹ is selected from the group consisting of radicals of the formulae
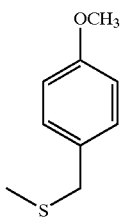 and 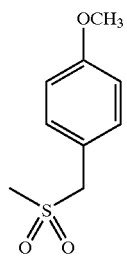 ; and
R² is fluoro or
R² is hydrogen and
R¹ is
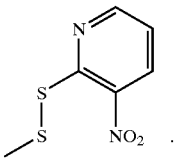 .
* * * * *

UNITED STATES PATENT AND TRADEMARK OFFICE
CERTIFICATE OF CORRECTION

PATENT NO. : 6,995,143 B2
APPLICATION NO. : 10/371108
DATED : February 7, 2006
INVENTOR(S) : Guerry et al.

It is certified that error appears in the above-identified patent and that said Letters Patent is hereby corrected as shown below:

Please correct Claim 1, Column 98, between lines 2 and 19, by substituting the correct general chemical compound as shown in amended Claim 1 on page 2 of Applicant's June 24, 2005 Amendment (see Exhibit A) as Allowed by the Office on July 18, 2005 (see Exhibit B).

Please correct the Abstract, by substituting the correct general chemical compound as shown in amended Claim 1 on page 2 of Applicant's June 24, 2005 Amendment (see Exhibit A) as Allowed by the Office on July 18, 2005 (see Exhibit B).

Please replace the general formula in the Summary Of The Invention, Column 2, between lines 57 and 67, by substituting the correct general chemical compound as shown in amended Claim 1 on page 2 of Applicant's June 24, 2005 Amendment (see Exhibit A) as Allowed by the Office on July 18, 2005 (see Exhibit B).

Please replace the general formula in the Detailed Description Of The Invention, Column 3, between lines 16 and 25, by substituting the correct general chemical compound as shown in amended Claim 1 on page 2 of Applicant's June 24, 2005 Amendment (see Exhibit A) as Allowed by the Office on July 18, 2005 (see Exhibit B).

Please correct Claim 1, Column 98, line 21, to read:

Y is S, SO, $SO_2$, $CH_2O$, or CO;

Please correct Claim 1, Column 98, line 50, to read:

n' is 0, 1, 2, 3, or 4;

Please correct Claim 15, Column 103, line 58, to read:

taneously $R^2$ is hydrogen, $R^3$ is methyl and Z is O when

Please correct Claim 16, Column 104, line 50, to read:

taneously $R^2$ is hydrogen, $R^3$ is methyl and Z is O when

UNITED STATES PATENT AND TRADEMARK OFFICE
CERTIFICATE OF CORRECTION

PATENT NO. : 6,995,143 B2
APPLICATION NO. : 10/371108
DATED : February 7, 2006
INVENTOR(S) : Guerry et al.

It is certified that error appears in the above-identified patent and that said Letters Patent is hereby corrected as shown below:

Please correct Claim 19, Column 106, line 49, to read:

taneously $R^2$ is hydrogen, $R^3$ is methyl and Z is O when

Signed and Sealed this

Fourteenth Day of July, 2009

JOHN DOLL
*Acting Director of the United States Patent and Trademark Office*